US009309560B2

(12) United States Patent
Smith et al.

(10) Patent No.: US 9,309,560 B2
(45) Date of Patent: Apr. 12, 2016

(54) METHODS FOR PRODUCING A PAIRED TAG FROM A NUCLEIC ACID SEQUENCE AND METHODS OF USE THEREOF

(75) Inventors: Douglas R. Smith, Gloucester, MA (US); Joel A. Malek, Beverly, MA (US); Kevin J. McKernan, Marblehead, MA (US)

(73) Assignee: Applied Biosystems, LLC, Carlsbad, CA (US)

( * ) Notice: Subject to any disclaimer, the term of this patent is extended or adjusted under 35 U.S.C. 154(b) by 785 days.

(21) Appl. No.: 12/468,818

(22) Filed: May 19, 2009

(65) Prior Publication Data

US 2010/0028888 A1 Feb. 4, 2010

Related U.S. Application Data

(62) Division of application No. 10/978,224, filed on Oct. 29, 2004, now abandoned.

(60) Provisional application No. 60/516,080, filed on Oct. 31, 2003.

(51) Int. Cl.
  *C12Q 1/68* (2006.01)
  *C12P 19/34* (2006.01)

(52) U.S. Cl.
  CPC .............. *C12Q 1/6816* (2013.01); *C12P 19/34* (2013.01); *C12Q 1/6806* (2013.01)

(58) Field of Classification Search
  None
  See application file for complete search history.

(56) References Cited

U.S. PATENT DOCUMENTS

| 5,229,273 A | 7/1993 | Gottesman et al. |
| 5,434,066 A | 7/1995 | Bebee et al. |
| 5,468,614 A | 11/1995 | Fields et al. |

(Continued)

FOREIGN PATENT DOCUMENTS

| WO | WO 0058522 A1 * | 10/2000 |
| WO | WO 01/79553 A1 | 10/2001 |

(Continued)

OTHER PUBLICATIONS

GenBank GI:208958 [online] Mar. 26, 1992 [retrieved on May 17, 2010] retrieved from: http://www.ncbi.nlm.nih.gov/sviewer/viewer.fcgi?val=208958&sat=OLDID&satkey=146275.*

(Continued)

*Primary Examiner* — Samuel Woolwine

(57) ABSTRACT

Methods for producing a paired tag from a nucleic acid sequence are provided in which the paired tag comprises the 5' end tag and 3' end tag of the nucleic acid sequence. In one embodiment, the nucleic acid sequence comprises two restriction endonuclease recognition sites specific for a restriction endonuclease that cleaves the nucleic acid sequence distally to the restriction endonuclease recognition sites. In another embodiment, the nucleic acid sequence further comprises restriction endonuclease recognition sites specific for a rare cutting restriction endonuclease. Methods of using paired tags are also provided. In one embodiment, paired tags are used to characterize a nucleic acid sequence. In a particular embodiment, the nucleic acid sequence is a genome. In one embodiment, the characterization of a nucleic acid sequence is karyotyping. Alternatively, in another embodiment, the characterization of a nucleic acid sequence is mapping of the sequence. In a further embodiment, a method is provided for identifying nucleic acid sequences that encode at least two interacting proteins.

17 Claims, 15 Drawing Sheets

(56) References Cited

U.S. PATENT DOCUMENTS

| | | | |
|---|---|---|---|
| 5,658,736 | A | 8/1997 | Wong |
| 5,695,937 | A | 12/1997 | Kinzler et al. |
| 5,866,330 | A | 2/1999 | Kinzler et al. |
| 5,925,523 | A | 7/1999 | Dove et al. |
| 5,968,784 | A | 10/1999 | Spinella et al. |
| 5,981,190 | A | 11/1999 | Israel |
| 6,054,276 | A | 4/2000 | Macevicz |
| 6,114,600 | A | 9/2000 | Ow et al. |
| 6,136,537 | A | 10/2000 | Macevicz |
| 6,200,759 | B1 | 3/2001 | Dove et al. |
| 6,235,472 | B1 * | 5/2001 | Landegren et al. ............... 435/6 |
| 6,383,743 | B1 | 5/2002 | Kinzler et al. |
| 6,465,254 | B1 | 10/2002 | Saito et al. |
| 6,498,013 | B1 | 12/2002 | Velculescu et al. |
| 6,551,828 | B1 | 4/2003 | Clark |
| 6,720,179 | B1 | 4/2004 | Macevicz |
| 7,425,431 | B2 | 9/2008 | Church et al. |
| 7,601,499 | B2 | 10/2009 | Berka et al. |
| 7,754,429 | B2 | 7/2010 | Rigatti et al. |
| 7,851,158 | B2 | 12/2010 | McKernan |
| 8,071,296 | B2 | 12/2011 | Ruan et al. |
| 8,192,930 | B2 | 6/2012 | Vermaas et al. |
| 8,846,347 | B2 | 9/2014 | Shendure et al. |
| 2002/0106646 | A1 * | 8/2002 | Remacle et al. ................. 435/6 |
| 2003/0008290 | A1 | 1/2003 | Velculescu et al. |
| 2003/0036069 | A1 | 2/2003 | Su |
| 2003/0049653 | A1 | 3/2003 | Kinzler et al. |
| 2004/0002090 | A1 | 1/2004 | Mayer |
| 2004/0082001 | A1 | 4/2004 | Macevicz |
| 2005/0164214 | A1 | 7/2005 | Pruitt |
| 2006/0024681 | A1 | 2/2006 | Smith et al. |
| 2008/0213771 | A1 | 9/2008 | Drmanac et al. |
| 2009/0093378 | A1 | 4/2009 | Bignell et al. |
| 2009/0156431 | A1 | 6/2009 | Lok |
| 2009/0181861 | A1 | 7/2009 | Li et al. |
| 2009/0233291 | A1 | 9/2009 | Chen et al. |
| 2009/0239764 | A1 | 9/2009 | Sparks et al. |
| 2009/0264299 | A1 | 10/2009 | Drmanac et al. |
| 2009/0325239 | A1 | 12/2009 | Lok |
| 2010/0120034 | A1 | 5/2010 | McKernan et al. |

FOREIGN PATENT DOCUMENTS

| | | |
|---|---|---|
| WO | WO 03/074734 A2 | 9/2003 |
| WO | WO 03/106678 | 12/2003 |
| WO | WO-2005/042781 | 5/2005 |
| WO | WO 2005/042781 | 5/2005 |
| WO | WO-2005/082098 | 9/2005 |
| WO | WO-2007/044245 | 4/2007 |
| WO | WO-2007/091077 | 8/2007 |
| WO | WO-2007/145612 | 12/2007 |
| WO | WO-2009/089384 | 7/2009 |
| WO | WO-2010/003153 | 1/2010 |

OTHER PUBLICATIONS

New England Biolabs Catalog, 1993/94 (cover and pp. 20, 30, 42, 43, 150 and 151).*
GenBank GI:287325315 [online] May 23, 2010 [retrieved on Oct 30, 2010] retrieved from: http://www.ncbi.nlm.nih.gov/nuccore/287325315 (4 pages total).*
Harmon et al. Biochemical characterization of the DNA helicase activity of the *Escherichia coli* RecQ helicase. J. Biol. Chem. 276(1):232-243, Jan. 5, 2001.*
GenBank GI:6691170 [online] Jan. 12, 2000 [retrieved on Oct. 31, 2010] retrieved from http://www.ncbi.nlm.nih.gov/nuccore/6691170?sat=NCBI&satkey=1779208.*
New England Biolabs information on BdaI restriction endonuclease [online] [retrieved on Oct. 30, 2010] retrieved from: http://www.neb.com/nebecomm/EnzymeFinderSearchByName.asp.*
GenBank GI:451770431 [online] Dec. 15, 2013 [retrieved on Dec. 22, 2013] retrieved from: http://www.ncbi.nlm.nih.gov/NG_016465.*
GenBank GI:160358355 [online] Dec. 11, 2013 [retrieved on Dec. 22, 2013] retrieved from http://www.ncbi.nlm.nih.gov/nuccore/NG_007075.1.*
GenBank GI:451770431 [online] Dec. 15, 2013 [retrieved on Dec. 23, 2013] retrieved from: http://www.ncbi.nlm.nih.gov/nuccore/451770431?report=fasta&to=2600.*
International Bureau of WIPO, International Searching Authority/European Patent Office, *Written Opinion and International Search Report* for PCT/US2004/036141 (Sep. 5, 2005), 6 pages.
International Bureau of WIPO, International Searching Authority/European Patent Office, *International Preliminary Report on Patentability* for PCT/US2004/036141 (Mar. 29, 2006), 6 pages.
Malek, J. A., et al., "Protein Interaction Mapping on a Functional Shotgun Sequence of Rickettsia sibirica," *Nucleic Acids Research*, Oxford University Press, 32(3):1059-1064 (2004).
Dunn, J.J., et al., "Genomic Signature Tags (GSTs); A System for Profiling Genomic DNA," *Genome Research*, 12:1756-1765 (2002).
Dove, S. L. and Hochschild, A., "Bacterial Two-Hybrid Analysis of Interactions Between Region 4 of the $\sigma^{70}$ Subunit of RNA Polymerase and the Transcriptional Regulators Rsd from *Escherichia coli* and AlgQ from Pseudomonas aeruginosa," *Journal of Bacteriology*, 183(21): 6413-6421 (2001).
Dove, S. L. and Hochschild, A., "Conversion of the ω Subunit of *Escherichia coli* RNA Polymerase Into a Transcriptional Activator or an Activation Target," *Genes & Development, Journal of Cellular and Molecular Biology*, pp. 745-754 (1998).
Zhang, Z. and Lutz, B., "Cre Recombinase-Mediated Inversion Using lox66 and lox 71: Method to Introduce Conditional Point Mutations Into the CREB-binding Protein," *Nucleic Acids Research*, 30(17):e90 (2002).
Albert, H, et al., "Site-Specific Integration of DNA Into Wild-Type and Mutant Lox Sites Placed in the Plant Genome," *The Plant Journal*, 7(4):649-659 (1995).
Velculescu, V.E., et al., "Serial Analysis of Gene Expression," *Science*, 270: 484-487 (1995).
Fields, S. and Song, O., "A Novel Genetic System to Detect Protein-Protein Interactions,", *Nature*, 340: 245-246 (1989).
Phizicky, E, et al., "Protein Analysis on a Proteomic Scale," *Nature*, 422:208-215 (2003).
Wang, T, et al., "Digital Karyotyping," *PNAS*, 99(25):16156-16161 (2002).
Belfort, M. and Roberts, R.J., "Homing Endonucleases: Keeping the House in Order," *Nucleic Acids Research*, 25(17):3379-3388 (1997).
Malek, J.A., et al., "Annotation of Novel Proteins Utilizing a Functional Genome Shotgun Coupled with High-throughput Protein Interaction Mapping," *Cold Spring Harbor Symposia on Quantitative Biology*, vol. LXVIII:331-334, Cold Spring Harbor Laboratory Press, (2003).
Briggs, Adrian et al., "Patterns of damage in genomic DNA sequences from a Neandertal", *PNAS*, vol. 104, No. 37, 2007, 14616-14621.
CN200980108336.7, First Search Report mailed Oct. 9, 2012 (Translation).
Fullwood, M. J. et al., "Next-generation DNA sequencing of paired-end tags (PET) for transcriptome and genome analyses", *Genome Research*, vol. 19, No. 4, 2009, 521-532.
Hall, Neil, "Advanced sequencing technologies and their wider impact in microbiology", *The Journal of Experimental Biology*, 209, 2007, 1518-1525.
Heiter, Daniel et al., "Site-Specific DNA-nicking Mutants of the Heterodimeric Restriction Endonuclease R.BbvCI", *J. Mol. Biol.*, 348, 2005, 631-640.
Kent, W et al., "Assembly of the Working Draft of the Human Genome with GigAssembler", *Genome Research*, vol. 11, 2001, pp. 1541-1548.
Korbel, Jan et al., "Paired-End Mapping Reveals Extensive Structural Variation in the Human Genome", *Science*, vol. 318, 2007, 420-426.
Mullikin, J et al., "The Phusion Assembler", *Genome Research*, vol. 13, 2003, pp. 81-90.
Ng, et al., "Multiplex sequencing of paired-end ditags (MS-PET): a strategy for the ultra-high-throughput analysis of transcriptomes and genomes", *Nucleic Acids Research*, vol. 34, No. 12, 2006, e84.

(56) References Cited

OTHER PUBLICATIONS

Ng, Patrick et al., "Gene identification signature (GIS) analysis for transcriptome characterization and genome annotation", *Nature Methods*, vol. 2, No. 2, 2005, 105-111.

PCT/US09/30490, International Preliminary Report on Patentability mailed Jul. 22, 2010.

PCT/US2009/030490, International Search Report mailed Jun. 5, 2009.

PCT/US2011/054053, International Search Report and Written Opinion mailed Mar. 5, 2012, 1-11.

Porreca, Gregory et al., "Polony DNA Sequencing", *Current Protocols in Molecular Biology*, 2006, 7.8.1-7.8.22.

Rigby, Peter et al., "Labeling Deoxyribonucleic Acid to High Specific Activity in Vitro by Nick Translation with DNA Polymerase I", *J. Mol. Biol.*, vol. 113, 1977, pp. 237-251.

Roach, Jared et al., "Pairwise End Sequencing: A Unified Approach to Genomic Mapping and Sequencing", *Genomics*, 26, 1995, 345-353.

Samuelson, James et al., "The isolation of strand-specific nicking endonucleases from a randomized SapI expression library", *Nucleic Acids Research*, vol. 32, No. 12, 2004, 3661-3671.

Shendure, J et al., "Accurate Multiplex Polony Sequencing of an Evolved Bacterial Genome", *Science*, vol. 309, 2005, 1728-1732.

Shuman, "Recombination mediated by vaccinia virus DNA topoisomerase I in *Escherichia coli* is sequence specific", *Proceedings of the National Academy of Sciences (PNAS)*, vol. 88, No. 22, Nov. 1991, 10104-10108.

Siegel, Andrew et al., "Modeling the Feasibility of Whole Genome Shotgun Sequencing Using a Pairwise End Strategy", *Genomics*, 68, 2000, 237-246.

Zhu, Zhenyu et al., "Engineering Strand-specific DNA Nicking Enzymes from the Type IIS Restriction Endonucleases BsaI, BsmBI, and BsmAI", *J. Mol. Biol.*, 337, 2004, 573-583.

\* cited by examiner

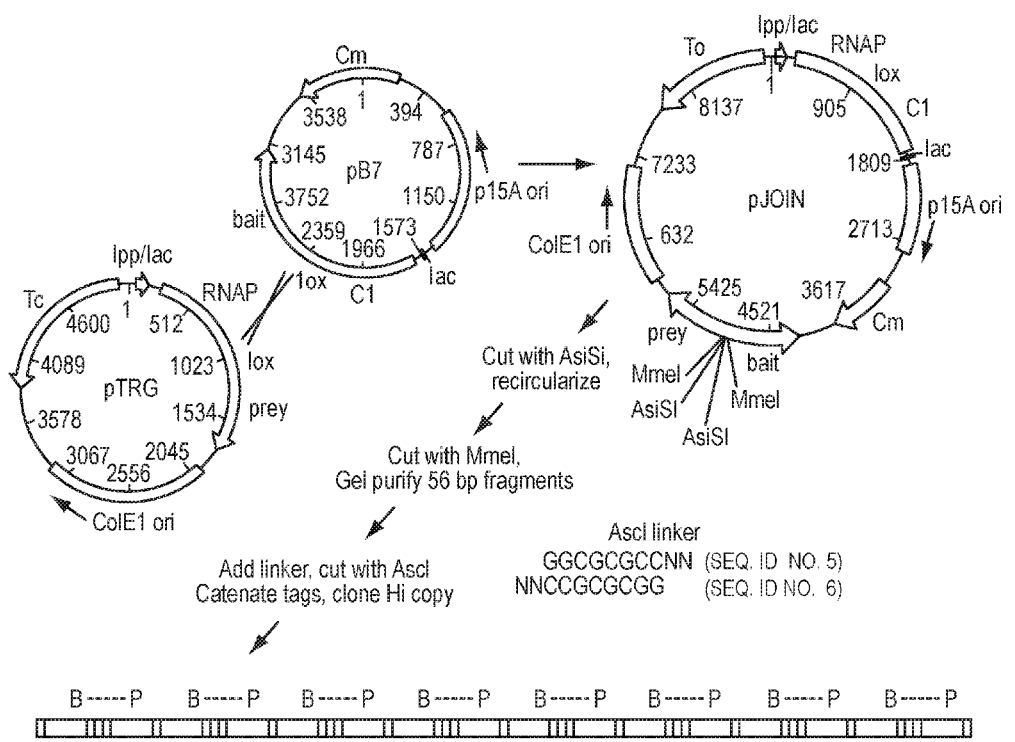

AsiSI site is 8 bp. MmeI is 5 bp. Tags are 20 bp. AscI linker is 8bp. Total of each di-tag is 68 bases (9 per read)

pBT Lox linker:------------------------Lox71------------------------AsiSI-----MmeI-----bait
C1 or RNAP - ATA ACT TCG TAT AAT GTA TGC TAT ACG AAC GGT AGC GAT CGC TCC AAC-N20 (SEQ ID NO. 7)
          Ile Thr Ser Tyr Asn Val Cys Tyr Thr Asn Gly Ser Asp Arg Ser Asn (SEQ ID NO. 8)
          (reading frame 1 is OK; frames 2 & 3 have stop codons)

pTRG Lox linker:------------------------Lox66------------------------AsiSI-----MmeI-----bait
C1 or RNAP - ATA ACT TCG TAT AGC ATA CAT TAT ACG AAC GGT AGC GAT CGC TCC AAC-N20 (SEQ ID NO. 9)
         Tyr Arg Ser Tyr Ser Ile His Tyr Thr Asn Gly Ser Asp Arg Ser Asn (SEQ ID NO. 10)
         (reading frame 1 is OK; frames 2 & 3 have stop codons)

FIG. 5

PAIRED GST
AaiSI GCGATCGC (SEQ ID NO: 17), NotI GCGGCCGC (SEQ ID NO: 18), PacI TTAATTAA (SEQ ID NO: 19)

NotI/MmeI linker
AAAAAATTAGCGGCCGCTCCGAC (SEQ ID NO: 20)
CH3-TTAATCGCCGGCGAGGCTG-PO4 (SEQ ID NO: 21)

PacI/MmeI linker (option)
AAAAAATGATTAATTAATCCGAC (SEQ ID NO: 22)
CH3-TTACTAATTAATTAGGCTG-PO4 (SEQ ID NO: 23)

AAAAAATTAGCGGCCGCTCCGAC-10kbFragment-GTCGGAGCGGCCGCTAATT-CH3 (SEQ ID NO: 24)
CH3-TTAATCGCCGGCGAGGCTG-10kbFragment-CAGCCTCGCCGGCGATTAAAAAA(SEQ ID NO: 25)
SIZE SELECT TO REMOVE LINKER DIMERS
CUT WITH NotI GGCCGCTCCGAC-10kbFragment-GTCGGAGC (SEQ ID NO: 26)
       CGAGGCTG-10kbFragment-CAGCCTCGCCGG (SEQ ID NO: 27)

SELF-CIRCULARIZE (LOW CONC) AND SIZE SELECT TO REMOVE >10kb CONCATEMERS
DIGEST WITH MmeI

Tag-GTCGGAGC GGCCGCTCCGAC-Tag (SEQ ID NO: 28)
Tag-CAGCCTCGCCGG CGAGGCTG-Tag (SEQ ID NO: 33)

CONCATENATE

FIG. 6D

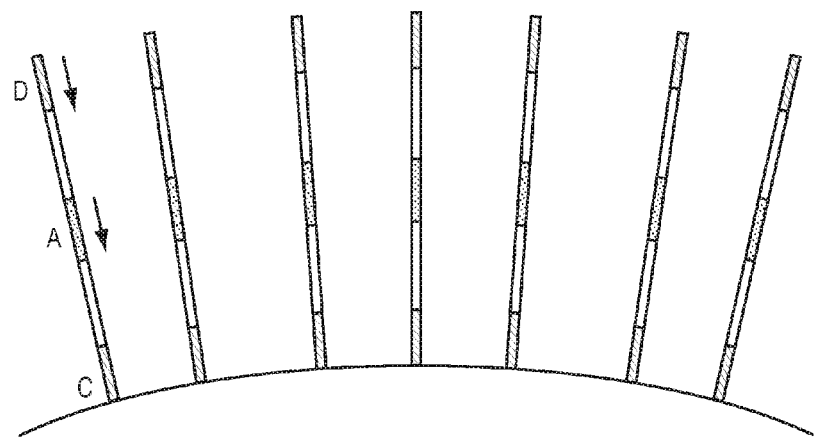
*I. CLONAL AMPLIFICATION ON BEAD IN ONE ORIENTATION*
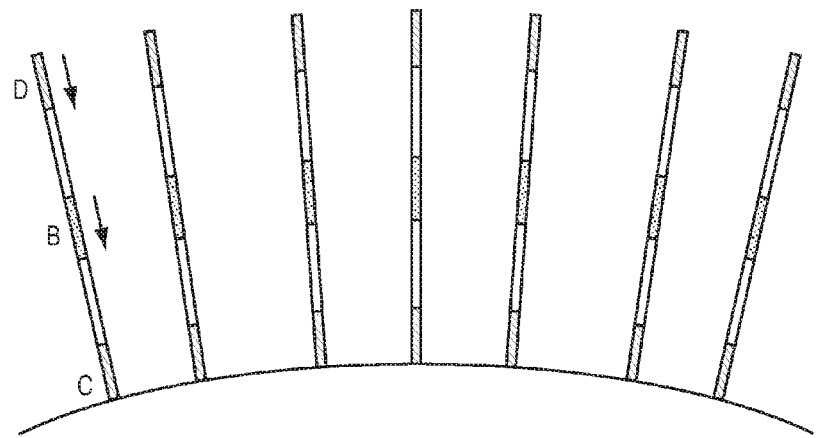
*II. CLONAL AMPLIFICATION ON BEAD IN ONE ORIENTATION*
FIG. 12

# METHODS FOR PRODUCING A PAIRED TAG FROM A NUCLEIC ACID SEQUENCE AND METHODS OF USE THEREOF

RELATED APPLICATION

This application is a continuation of application Ser. No. 10/978,224, filed Oct. 29, 2004, which is incorporated herein by reference.

This application claims a priority benefit under 35 U.S.C. §119(e) from U.S. Patent Application No. 60/516,080, filed Oct. 31, 2003, which is incorporated herein by reference.

BACKGROUND OF THE INVENTION

Whole genome shotgun sequencing, assembly and finishing is typically the strategy of choice for microbial and fungal genome sequencing. The cost-advantages and simplicity of the whole genome approach relative to a BAC based or hybrid sequencing strategy argue strongly for its continued development and application in future sequencing projects. However, a major problem with the BAC-based approaches is the high cost and operational burden associated with the production of 15,000-25,000 individual BAC subclone libraries, the 15-20% waste associated with re-sequencing the vector, as well as the unavoidable *E. coli* contamination, the need to deal with transposon and bacteriophage insertions, and the 20-50% waste in redundant sequencing of BAC overlaps. Although these costs can be reduced by sequencing the BACs at low coverage (using a hybrid BAC/WGS strategy, for example) or by using a pooling strategy, they cannot be eliminated. The need to generate a physical map by using restriction digest fingerprinting or by complex pooling and sequence based mapping strategies adds additional cost and operational overhead.

Thus, a need exists for more cost-efficient sequencing methods and for better methods of generating a reliable sequence-derived scaffold that can support the accurate selection of clones to finish any desired region of the genome with reduced operational burden, increased efficiency, elimination of problems associated with transposon and bacteriophage insertions and reduction in wasted time, effort and expense spent in redundant sequencing. Additionally, a need exists to provide a reliable and efficient method that facilitates whole genome assembly and/or karyotyping of a genome, and which enables the reliable and efficient detection of sequence inversion in a genome.

Current bacterial and yeast two-hybrid screening methods are useful to discover the identity of two interacting proteins. However, these methods suffer from the need for large numbers of transformations to be performed: one for each bait to be analyzed against one or more prey molecule. Although some methods have been developed to permit pools of ten to one hundred baits to be screened in parallel, these methods require additional handling steps to deconvolute the identities of the individual baits. Therefore, these methods only incrementally increase the efficiency of conventional two-hybrid systems.

Thus, a need exists for a method to increase the efficiency of two-hybrid systems for the identification of two interacting proteins.

SUMMARY OF THE INVENTION

The present invention provides a method for producing a paired tag from a nucleic acid sequence (also referred to herein as a nucleotide sequence), wherein at least one restriction endonuclease recognition site is present at the 5' and 3' end of the nucleic acid sequence and upon cleavage results in production a paired tag. In one embodiment the present invention provides a method for producing a paired tag from a nucleic acid sequence, wherein two restriction endonuclease recognition sites specific for a restriction endonuclease that cleaves the nucleic acid sequence fragment distally to the restriction endonuclease recognition site are present at the 5' and 3' ends of the nucleic acid sequence, thereby producing a 5' tag and a 3' tag (a paired tag) from the nucleic acid sequence upon cleavage by the restriction endonuclease.

In another embodiment the present invention provides a method for producing a paired tag from a nucleic acid sequence, wherein the nucleic acid sequence comprises one restriction endonuclease recognition site specific for a restriction endonuclease that cleaves the nucleic acid sequence on both sides of the recognition site.

In addition, the present invention provides a method for producing a paired tag from a nucleic acid sequence, wherein the nucleic acid sequence comprises two restriction endonuclease recognition sites specific for a restriction endonuclease that cleaves the nucleic acid sequence between the two recognition sites.

The present invention also provides a method for producing a paired tag from a nucleic acid sequence, wherein the nucleic acid sequence comprises at least one linker, the at least one linker is joined to the 5' and 3' ends of the nucleic acid sequence, wherein producing a fragment on either or both sides of the linker produces a paired tag from the nucleic acid sequence.

The present invention also provides a method for producing a paired tag from a nucleic acid sequence, wherein the nucleic acid sequence comprises at least one recombination site, wherein a recombination event at this recombination site in the nucleic acid sequence produces a paired tag from the nucleic acid sequence.

Furthermore, the present invention provides methods of using a paired tag to characterize a sequence and identify nucleic acid sequences that encode at least two interacting proteins.

In one embodiment, the invention is directed to a method for producing a paired tag from a nucleic acid sequence, wherein the nucleic acid sequence comprises two restriction endonuclease recognition sites specific for a restriction endonuclease that cleaves the nucleic acid sequence distally to the restriction endonuclease recognition site, comprising the steps of cleaving the restriction endonuclease recognition sites using the restriction endonuclease that is specific for the restriction endonuclease recognition sites, thereby producing a 5' end tag and a 3' end tag from the nucleic acid sequence and joining the 5' end tag with the 3' end tag from the nucleic acid sequence, thereby producing a paired tag from the nucleic acid sequence. In a particular embodiment, the nucleic acid sequence further comprises at least two restriction endonuclease recognition sites specific for a rare cutting restriction endonuclease.

In another embodiment of the invention, a method is provided for characterizing a nucleic acid sequence comprising the steps of a) fragmenting a nucleic acid sequence thereby producing a plurality of nucleic acid sequence fragments having a 5' end and a 3' end, b) introducing into the 5' end and into the 3' end of each nucleic acid sequence fragment, (i) a restriction endonuclease recognition site specific for a restriction endonuclease that cleaves the nucleic acid sequence fragment distally to the restriction endonuclease recognition site, and (ii) a restriction endonuclease recognition site specific for a rare cutting restriction endonuclease, thereby producing modified nucleic acid sequence fragments, c) cleaving the restriction endonuclease recognition site specific for a rare cutting restriction endonuclease in each modified nucleic acid sequence fragment with the rare cutting restriction endonuclease, thereby producing a plurality of nucleic acid sequence fragments having compatible ends, d) maintaining the fragments having compatible ends under conditions in which the compatible ends intramolecularly ligate, thereby producing a plurality of circularized nucleic acid sequences comprising two restriction endonuclease recognition sites specific for restriction endonucleases that cleave the nucleic acid sequence fragment distally to the restriction endonuclease recognition sites, e) cleaving the circularized nucleic acid sequences at the restriction endonuclease recognition sites with the restriction endonucleases specific for the restriction endonuclease recognition sites, thereby producing a plurality of paired tags comprising a 5' end tag and a 3' end tag of the nucleic acid sequence fragment, and f) characterizing the paired tags, thereby characterizing the nucleic acid sequence. In one embodiment, the nucleic acid sequence is a genome. In a further embodiment, the method karyotypes the genome.

The invention also provides in one embodiment, a method for characterizing a nucleic acid sequence comprising the steps of a) fragmenting a nucleic acid sequence thereby producing a plurality of nucleic acid sequence fragments having a 5' end and a 3' end, b) introducing into the 5' end and into the 3' end of each nucleic acid sequence fragment a restriction endonuclease recognition site specific for a restriction endonuclease that cleaves the nucleic acid sequence fragment distally to the restriction endonuclease recognition site, thereby producing a plurality of modified nucleic acid sequence fragments, c) cloning the modified nucleic acid sequence fragments, thereby producing cloned nucleic acid sequence fragments, d) cleaving the restriction endonuclease recognition sites at the 5' end and the 3' end of the cloned nucleic acid sequence fragments using the restriction endonuclease that is specific for the restriction endonuclease recognition sites, thereby producing a 5' end tag and a 3' end tag of each cloned nucleic acid sequence fragment, e) joining the 5' end tag to the 3' end tag of each cloned nucleic acid sequence fragment thereby producing a plurality of paired tags; and f) characterizing the paired tags, thereby characterizing the nucleic acid sequence.

In another aspect of the invention, provided herein is a method for characterizing a nucleic acid sequence comprising the steps of a) fragmenting a nucleic acid sequence thereby producing a plurality of nucleic acid sequence fragments having a 5' end and a 3' end, b) cloning each nucleic acid sequence fragment, wherein a restriction endonuclease recognition site specific for a restriction endonuclease that cleaves the nucleic acid sequence fragment distally to the restriction endonuclease recognition site is introduced into the 5' end and into the 3' end of each cloned nucleic acid sequence fragment, thereby producing a plurality of cloned nucleic acid sequence fragments, c) cleaving the restriction endonuclease recognition sites at the 5' end and the 3' end of each cloned nucleic acid sequence fragment using the restriction endonuclease that is specific for the restriction endonuclease recognition sites, thereby producing a 5' end tag and a 3' end tag of the cloned nucleic acid sequence fragments, d) joining the 5' end tag to the 3' end tag of each cloned nucleic acid sequence fragment thereby producing a plurality of paired tags, and e) characterizing the paired tags, thereby characterizing the nucleic acid sequence.

In one embodiment of the invention, provided herein is a method for producing a paired tag from a first nucleic acid sequence fragment, without cloning, comprising the steps of joining the 5' and 3' ends of a nucleic acid sequence fragment via a linker such that the linker is located between the 5' end and the 3' end of the first nucleic acid sequence fragment in a circular nucleic acid molecule, b) cleaving the circular nucleic acid molecule, thereby producing a paired tag wherein a 5'end tag of the first nucleic acid sequence fragment is joined to a 3' end tag of the first nucleic acid sequence fragment via the linker. In one embodiment, the linker comprises at least two restriction endonuclease recognition sites specific for a restriction endonuclease that cleaves the nucleic acid sequence fragment distally to the restriction endonuclease recognition site, and the circular nucleic acid molecule is cleaved with a restriction endonuclease that cleaves the nucleic acid sequence fragment distally to the restriction endonuclease recognition site to thereby producing the paired tag. In a further embodiment, the restriction endonuclease recognition sites are immediately adjacent to the ends of the first nucleic acid sequence fragment.

In a further embodiment of the invention, provided herein is a method for producing a paired tag from a first nucleic acid sequence fragment, without cloning, comprising the steps of a) joining the 5' and 3'ends of a first nucleic acid sequence fragment to at least one adapter, b) cleaving the adapter(s), thereby producing a second nucleic acid sequence fragment with compatible ends, c) circularizing the second nucleic acid sequence fragment such that a 5'end of the first nucleic acid sequence fragment is joined to a 3' end of the first nucleic acid sequence fragment via a linker derived from the adapter(s), thereby producing a circular nucleic acid molecule, and cleaving the circular nucleic acid molecule, thereby producing a paired tag wherein a 5'end tag of the first nucleic acid sequence fragment is joined to a 3' end tag of the first nucleic acid sequence fragment via the linker. In a particular embodiment, the adapter comprises at least two restriction endonuclease recognition sites specific for a restriction endonuclease that cleaves the nucleic acid sequence fragment distally to the restriction endonuclease recognition site, the adapter comprises a restriction endonuclease recognition site specific for a rare cutting restriction endonuclease, cleaving the adapter joined to the nucleic acid sequence fragment with a rare cutting restriction endonuclease to produce the compatible ends, and cleaving the circular nucleic acid molecule with a restriction endonuclease that cleaves distally to the restriction endonuclease recognition site. In a further embodiment, the restriction endonuclease recognition sites specific for a restriction endonuclease that cleaves the nucleic acid sequence fragment distally to the restriction endonuclease recognition site are immediately adjacent to the 5' and 3' ends of the nucleic acid sequence fragment.

In another embodiment, provided herein is a method for producing a paired tag from a first nucleic acid sequence fragment, without cloning, comprising the steps of a) joining the 5' and 3' ends of a first nucleic acid sequence fragment via a first linker such that the first linker is located between the 5' end and the 3' end of the first nucleic acid sequence fragment in a first circular nucleic acid molecule, b) cleaving the first circular nucleic acid molecule, thereby producing a second nucleic acid sequence fragment wherein a 5'end tag of the first nucleic acid sequence fragment is joined to a 3' end tag of the first nucleic acid sequence fragment via the first linker, c) joining a second linker to the 5' and 3' ends of the second nucleic acid sequence fragment, and d) amplifying the second nucleic acid fragment using an oligonucleotide complementary to a sequence present in the second linker.

In a further embodiment of the invention, provided herein is a method for producing a paired tag from a first nucleic acid sequence fragment, without cloning, comprising the steps of a) joining the 5' and 3' ends of a first nucleic acid sequence fragment via a first linker such that the first linker is located between the 5' end and the 3' end of the first nucleic acid sequence fragment in a first circular nucleic acid molecule, b) cleaving the first circular nucleic acid molecule, thereby producing a second nucleic acid sequence fragment wherein a 5'end tag of the first nucleic acid sequence fragment is joined to a 3' end tag of the first nucleic acid sequence fragment via the first linker, c) joining the 5' and 3' ends of a second nucleic acid sequence fragment via a second linker such that the second linker is located between the 5' end and the 3' end of the first nucleic acid sequence fragment in a second circular nucleic acid molecule, and d) amplifying a nucleic acid sequence fragment from the second circular nucleic acid molecule using two oligonucleotides complementary to sequences present in the second linker. In one embodiment, the second linker comprises a recognition site for a rare-cutting restriction endonuclease, and the second circular nucleic acid molecule is cleaved using a rare-cutting restriction endonuclease that recognizes the site in the second linker. In another embodiment, the first linker comprises at least two restriction endonuclease recognition sites specific for a restriction endonuclease that cleaves the nucleic acid sequence fragment distally to the restriction endonuclease recognition site, and the first circular nucleic acid molecule is cleaved with a restriction endonuclease that cleaves the nucleic acid sequence fragment distally to the restriction endonuclease recognition site. In a particular embodiment, the restriction endonuclease recognition sites specific for a restriction endonuclease that cleaves the nucleic acid sequence fragment distally to the restriction endonuclease recognition site are immediately adjacent to the ends of the first nucleic acid sequence fragment. Furthermore, in one embodiment, the second nucleic acid fragment is purified prior to amplification, for example by affinity capture using a reagent specific for the first linker prior to amplification. In one example, the first linker comprises a biotin moiety, a sequence capable of forming a triple helix, or a recognition site for a DNA binding protein.

In another embodiment of the invention, provided herein is a method for characterizing a nucleic acid sequence comprising the steps of a) fragmenting a nucleic acid sequence to produce a plurality of nucleic acid sequence fragments having a 5' end and a 3' end, b) joining one or more first adapters to the 5' and 3' ends, wherein the one or more first adapters are compatible for promoting intramolecular ligation, thereby producing a plurality of modified nucleic acid sequence fragments, intramolecularly ligating the modified nucleic acid sequence fragments thereby producing a plurality of circularized nucleic acid sequences, wherein the one or more first adapters forms a linker between the 5'end and the 3'end of the circularized nucleic acid sequence fragment, c) fragmenting the circularized nucleic acid sequences by random shearing or by other means thereby producing linear fragments comprising the linker and a paired tag comprising the 5' end and a 3' end of the nucleic acid sequence fragment, d) joining a second adapter to each of the 5' and 3' ends of the linear fragments to produce a plurality of linear fragments having the second adapter at each 5' and 3' end, e) amplifying the linear fragments using a primer that is complementary to the second adapter thereby amplifying the paired tags, and f) characterizing the paired tags, thereby characterizing the nucleic acid sequence.

In another aspect of the invention, provided herein is a method for characterizing a nucleic acid sequence comprising the steps of a) fragmenting a nucleic acid sequence to produce a plurality of nucleic acid sequence fragments each having a 5' end and a 3' end, b) joining one or more first adapters to the 5' and 3' ends, wherein the one or more first adapters are compatible for promoting intramolecular ligation, thereby producing a first plurality of modified nucleic acid sequence fragments, intramolecularly ligating the modified nucleic acid sequence fragments thereby producing a first plurality of circularized nucleic acid sequences, wherein the one or more first adapters forms a first linker between the 5'end and the 3'end of the circularized nucleic acid sequence fragment, c) fragmenting the circularized nucleic acid fragments by random shearing or by other means thereby producing linear fragments comprising the first linker and a paired tag comprising the 5' end and a 3' end of the nucleic acid sequence fragment, d) joining a second adapter to each of the 5' and 3' ends of the fragments to produce a second plurality of modified fragments having the second adapter at each 5' and 3' end, wherein the second adapter at the 5' and 3' ends are compatible for promoting intramolecular ligation, intramolecularly ligating the second plurality of modified nucleic acid sequence fragments thereby producing a second plurality of circularized nucleic acid sequences, wherein the second adapter at each 5' and 3' end form a second linker located between the 5' and 3' ends of the second plurality of circularized nucleic acid sequences, and wherein the second linker comprises two priming sites, f) amplifying the second plurality of circularized nucleic acid sequences using two different primers that are complementary to the priming sites in the second linker, thereby amplifying the paired tags, and g) characterizing the paired tags, thereby characterizing the nucleic acid sequence.

In an alternative aspect of the invention, provided herein is a method for characterizing a nucleic acid sequence comprising the steps of a) fragmenting a nucleic acid sequence to produce a plurality of nucleic acid sequence fragments having a 5' end and a 3' end, b) joining one or more first adapters to the 5' and 3' ends, wherein the one or more first adapters are compatible for promoting intramolecular ligation, thereby producing a first plurality of modified nucleic acid sequence fragments, intramolecularly ligating the first plurality of modified nucleic acid sequence fragments thereby producing a first plurality of circularized nucleic acid sequences, wherein the one or more first adapters forms a first linker between the 5'end and the 3'end of the circularized nucleic acid sequence fragment, c) fragmenting the first plurality of circularized nucleic acid sequences by random shearing or by other means, thereby producing first linear fragments comprising the first linker and a paired tag comprising the 5' end and a 3' end of the nucleic acid sequence fragment, d) joining one or more second adapters to the each of the 5' and 3' ends of the first linear fragments, wherein the one or more second adapters are compatible for promoting intramolecular ligation, thereby producing a second plurality of modified nucleic acid sequence fragments, and intramolecularly ligating the second plurality of modified nucleic acid sequence fragments to produce a second plurality of circularized nucleic acid sequences, wherein the on or more second adapters form a second linker between the 5'end and the 3'end of the second circularized nucleic acid sequence fragments, and wherein the second linker comprises two priming sites separated by a rare-cutting restriction endonuclease cleavage site, f) cleaving the second plurality of circularized nucleic acid sequences using a rare-cutting restriction endonuclease that recognizes the cleavage site in the second linker, thereby producing a second plurality of linear fragments g) amplifying the second plurality of linear fragments using two different primers that are complementary to the priming sites in the second linker, and h) characterizing the paired tags, thereby characterizing the nucleic acid sequence.

In another aspect of the invention, provided herein is a method for characterizing a nucleic acid sequence comprising the steps of a) fragmenting a nucleic acid sequence to produce a plurality of nucleic acid sequence fragments having a 5' end and a 3' end, b) joining one or more first adapters to the 5' and 3' ends, wherein the one or more first adapters are compatible for promoting intramolecular ligation, thereby producing a first plurality of modified nucleic acid sequence fragments, intramolecularly ligating the first plurality of modified nucleic acid sequence fragments thereby producing a first plurality of circularized nucleic acid sequences, wherein the one or more first adapters forms a first linker between the 5'end and the 3'end of the circularized nucleic acid sequence fragment, and wherein the first linker comprises a sequence or chemical moiety that enables isolation or separation (e.g., by affinity capture), c) fragmenting the first plurality of circularized nucleic acid sequences by random shearing or by other means, thereby producing linear fragments comprising the first linker and a paired tag comprising the 5' end and the 3' end of the nucleic acid sequence fragment, d) purifying the linear fragments by affinity capture, e) joining one or more second adapters to the each of the 5' and 3' ends of the first linear fragments, wherein the one or more second adapters are compatible for promoting intramolecular ligation, thereby producing a second plurality of modified nucleic acid sequence fragments, and intramolecularly ligating the second plurality of modified nucleic acid sequence fragments to produce a second plurality of circularized nucleic acid sequences, wherein the one or more second adapters form a second linker between the 5'end and the 3'end of the second circularized nucleic acid sequence fragments, and wherein the second linker comprises two priming sites, f) amplifying the nucleic acid sequence fragments using two different primers that are complementary to the priming sites in the second linker, and g) characterizing the paired tags, thereby characterizing the nucleic acid sequence.

In one embodiment, provided herein is a composition comprising nucleic acid sequence elements arranged in the following order: [0026] linker 1—5' end tag—linker 2—3' end tag—linker 3 wherein the 5'end tag and the 3'end tag comprise a paired tag derived from a single contiguous nucleic acid sequence fragment. In a particular embodiment, linker 2 comprises at least two restriction endonuclease recognition sites specific for a restriction endonuclease that cleaves the nucleic acid sequence fragment distally to the restriction endonuclease recognition site, and is oriented in such a way that one of the sites directs cleavage within the 5'end tag or at the junction of linker 1 and the 5'end tag, and the other site directs cleavage within the 3' end tag or at the junction of linker 3 and the 3'end tag. In another embodiment, the linker 2 comprises at least two restriction endonuclease recognition sites specific for a restriction endonuclease that cleaves the nucleic acid sequence fragment distally to the restriction endonuclease recognition site, and is oriented in such a way that one of the sites directs cleavage within the 5'end tag or at the junction of linker 1 and the 5'end tag, and the other site directs cleavage within the 3' end tag or at the junction of linker 3 and the 3'end tag, and at least one recognition site for a rare-cutting restriction endonuclease located between the two restriction endonuclease recognition sites specific for a restriction endonuclease that cleaves the nucleic acid sequence fragment distally to the restriction endonuclease recognition site. In one example, linker 1 and linker 3 are the same sequence in reverse orientation. In a further embodiment, oligonucleotides complementary to sequences present in linker 1 and linker 3 are used for amplification. In another example, linker 1 and linker 3 are derived by cleavage of a circular nucleic acid molecule with a rare-cutting restriction endonuclease comprising a recognition site between linker 1 and linker 3.

In a further embodiment of the invention, provided herein is a composition comprising a circular nucleic acid molecule, wherein sequence elements are arranged in the following circular order:

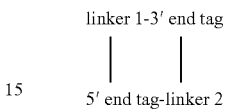

wherein the 5'end tag and the 3'end tag comprise a paired tag derived from a single contiguous nucleic acid sequence fragment. In one embodiment, linker 1 comprises at least two restriction endonuclease recognition sites specific for a restriction endonuclease that cleaves the nucleic acid sequence fragment distally to the restriction endonuclease recognition site, and are oriented in such a way that one of the sites directs cleavage within the 5'end tag or at the junction of the 5'end tag and linker 2, and the other site directs cleavage within the 3' end tag or at the junction of the 3'end tag and linker 2. In another embodiment, linker 2 comprises at least two restriction endonuclease recognition sites specific for a restriction endonuclease that cleaves the nucleic acid sequence fragment distally to the restriction endonuclease recognition site, and are oriented in such a way that one of the sites directs cleavage within the 5'end tag or at the junction of the 5'end tag and linker 2 and, and the other site directs cleavage within the 3' end tag or at the junction of the 3'end tag and linker 2, and at least one recognition site for a rare-cutting restriction endonuclease located between the two restriction endonuclease recognition sites specific for a restriction endonuclease that cleaves the nucleic acid sequence fragment distally to the restriction endonuclease recognition site. In one embodiment, linker 2 is palindromic. In another embodiment, linker 2 comprises a recognition site for a rare-cutting restriction endonuclease. In a further embodiment, oligonucleotide primers complementary to sequences in either linker 1 or linker 2, or in both linker 1 and linker 2 are used for isothermic amplification, for example, oligonucleotide primers complementary to sequences in either linker 1 or linker 2, and oriented in opposite directions such that a linear nucleic acid fragment is produced that preserves the orientation of the 5'end tag and the 3'end tag with respect to each other are used.

In a further aspect of the invention, provided herein is a method for characterizing a nucleic acid sequence comprising the steps of a) fragmenting a nucleic acid sequence to produce a plurality of nucleic acid sequence fragments having a 5' end and a 3' end, b) joining one or more first adapters to the 5' and 3' ends, wherein the one or more first adapters are compatible for promoting intramolecular ligation, thereby producing a first plurality of modified nucleic acid sequence fragments, intramolecularly ligating the first plurality of modified nucleic acid sequence fragments thereby producing a first plurality of circularized nucleic acid sequences, wherein the one or more first adapters forms a first linker between the 5'end and the 3'end of the circularized nucleic acid sequence fragment, and wherein the first linker comprises a sequence or chemical moiety that enables affinity capture, c) fragmenting the first plurality of circularized nucleic acid sequences by random shearing or by other means, thereby producing first linear fragments comprising the first linker and a paired tag comprising the 5' end and a 3' end of the nucleic acid sequence fragment, d) purifying the linear fragments by affinity capture, e) joining one or more second adapters to the each of the 5' and 3' ends of the first linear fragments, wherein the one or more second adapters are compatible for promoting intramolecular ligation, thereby producing a second plurality of modified nucleic acid sequence fragments, and intramolecularly ligating the second plurality of modified nucleic acid sequence fragments to produce a second plurality of circularized nucleic acid sequences, wherein the on or more second adapters form a second linker between the 5'end and the 3'end of the second circularized nucleic acid sequence fragments, and wherein the second linker comprises two priming sites separated by a rare-cutting restriction endonuclease cleavage site, f) cleaving the second plurality of circularized nucleic acid sequences using a rare-cutting restriction endonuclease that recognizes the cleavage site in the second adapter, thereby producing a second plurality of linear fragments, g) amplifying the second plurality of linear fragments using two different primers that are complementary to the priming sites in the second linker, h) characterizing the paired tags, thereby characterizing the nucleic acid sequence.

In a further aspect of the invention, a method for identifying nucleic acid sequences that encode at least two interacting proteins is provided, comprising the steps of a) combining (i) a first vector comprising (1) a nucleic acid sequence that encodes a first protein that interacts with a second protein, and (2) a first restriction endonuclease recognition site specific for a restriction endonuclease that cleaves the nucleic acid sequence fragment distally to the restriction endonuclease recognition site, and (ii) a second vector comprising (1) a nucleic acid sequence that encodes the second protein; and (2) a second restriction endonuclease recognition site specific for a restriction endonuclease that cleaves the nucleic acid sequence fragment distally to the restriction endonuclease recognition site, thereby producing a combination, b) optionally maintaining the combination under conditions in which the first protein and the second protein are expressed and interact, c) joining the first vector with the second vector, thereby forming a contiguous nucleic acid sequence that comprises (i) the nucleic acid sequence that encodes a first protein that interacts with a second protein, (ii) the first restriction endonuclease recognition site specific for a restriction endonuclease that cleaves the nucleic acid sequence fragment distally to the restriction endonuclease recognition site, (iii) the nucleic acid sequence that encodes the second protein, and (iv) the second restriction endonuclease recognition site specific for a restriction endonuclease that cleaves the nucleic acid sequence fragment distally to the restriction endonuclease recognition site, d) cleaving the first restriction endonuclease recognition site and the second restriction endonuclease recognition site in the contiguous nucleic acid sequence with restriction endonucleases that cleave the contiguous nucleic acid sequence distally to the restriction endonuclease recognition sites, thereby producing a 5' end tag and a 3' end tag of the contiguous nucleic acid sequence, e) joining the 5' end tag to the 3' end tag, thereby producing a paired tag, and f) sequencing the paired tag, thereby identifying nucleic acid sequences that encode at least two interacting proteins.

In an additional embodiment of the invention, provided is a method for identifying nucleic acid sequences that encode at least two interacting proteins comprising the steps of a) combining (i) a first vector comprising (1) a nucleic acid sequence that encodes a first protein that interacts with a second protein, and (2) a first restriction endonuclease recognition site specific for a restriction endonuclease that cleaves the nucleic acid sequence fragment distally to the restriction endonuclease recognition site, and (ii) a second vector comprising (1) a nucleic acid sequence that encodes the second protein, and (2) a second restriction endonuclease recognition site specific for a restriction endonuclease that cleaves the nucleic acid sequence fragment distally to the restriction endonuclease recognition site, thereby producing a combination, b) optionally maintaining the combination under conditions in which the first protein and the second protein are expressed and interact, c) joining the first vector with the second vector, thereby forming a contiguous nucleic acid sequence that comprises (i) the nucleic acid sequence that encodes a first protein that interacts with a second protein, (ii) the first restriction endonuclease recognition site specific for a restriction endonuclease that cleaves the nucleic acid sequence fragment distally to the restriction endonuclease recognition site, (iii) the nucleic acid sequence that encodes the second protein, and (iv) the second restriction endonuclease recognition site specific for a restriction endonuclease that cleaves the nucleic acid sequence fragment distally to the restriction endonuclease recognition site, d) sequencing the contiguous nucleic acid sequence, thereby identifying nucleic acid sequences that encode at least two interacting proteins.

In another embodiment of the invention, provided is a method for identifying nucleic acid sequences that encode at least two interacting proteins comprising the steps of a) combining, (i) a first vector comprising (1) a nucleic acid sequence that encodes a first protein that interacts with a second protein, and (2) a first restriction endonuclease recognition site specific for a restriction endonuclease that cleaves the nucleic acid sequence fragment distally to the restriction endonuclease recognition site, and (ii) second vector comprising (1) a nucleic acid sequence that encodes the second protein; and (2) a second restriction endonuclease recognition site specific for a restriction endonuclease that cleaves the nucleic acid sequence fragment distally to the restriction endonuclease recognition site, thereby producing a combination, b) optionally maintaining the combination under conditions in which the first protein and the second protein are expressed and interact, c) joining the first vector with the second vector, thereby forming a contiguous nucleic acid sequence that comprises (i) the nucleic acid sequence that encodes a first protein that interacts with a second protein, (ii) the first restriction endonuclease recognition site specific for a restriction endonuclease that cleaves the nucleic acid sequence fragment distally to the restriction endonuclease recognition site, (iii) the nucleic acid sequence that encodes the second protein, and (iv) the second restriction endonuclease recognition site specific for a restriction endonuclease that cleaves the nucleic acid sequence fragment distally to the restriction endonuclease recognition site, d) cleaving the first restriction endonuclease recognition site and the second restriction endonuclease recognition site in the contiguous nucleic acid sequence with restriction endonucleases that cleave the contiguous nucleic acid sequence distally to the restriction endonuclease recognition sites, thereby producing a paired tag comprising a 5' end tag and a 3' end tag of the contiguous nucleic acid sequence, e) sequencing the paired tag, thereby identifying nucleic acid sequences that encode at least two interacting proteins.

In a further embodiment of the invention, provided is a method for identifying a plurality of nucleic acid sequences that encode at least two interacting proteins comprising the steps of a) combining (i) a plurality of first vectors each comprising (1) a nucleic acid sequence that encodes a first protein that interact with a second protein; and (2) a first restriction endonuclease recognition site specific for a restriction endonuclease that cleaves the nucleic acid sequence fragment distally to the restriction endonuclease recognition site, and (ii) a plurality of second vectors each comprising (1) a nucleic acid sequence that encodes the second protein; and (2) a second restriction endonuclease recognition site specific for a restriction endonuclease that cleaves the nucleic acid sequence fragment distally to the restriction endonuclease recognition site, thereby producing a combination comprising a plurality of first vectors and a plurality of second vectors, b) optionally maintaining the combination under conditions in which the plurality of first vectors encoding a first protein and the plurality of second vectors encoding a second protein are expressed and the first protein and second protein interact, c) joining the first vectors with the second vectors, wherein the first vectors and second vectors encode interacting proteins, thereby forming a plurality of contiguous nucleic acid sequences that each comprise (i) the nucleic acid sequence that encodes a first protein that interacts with a second protein, (ii) the first restriction endonuclease recognition site specific for a restriction endonuclease that cleaves the nucleic acid sequence fragment distally to the restriction endonuclease recognition site, (iii) the nucleic acid sequence that encodes the second protein, and (iv) the second restriction endonuclease recognition site specific for a restriction endonuclease that cleaves the nucleic acid sequence fragment distally to the restriction endonuclease recognition site, d) cleaving the first restriction endonuclease recognition site and the second restriction endonuclease recognition site in each contiguous nucleic acid sequence with restriction endonucleases that cleave the contiguous nucleic acid sequence distally to the restriction endonuclease recognition sites, thereby producing a plurality of paired tags comprising a 5' end tag and a 3' end tag of the contiguous nucleic acid sequence, e) joining the paired tags; and f) sequencing the joined paired tags, thereby identifying a plurality of nucleic acid sequences that encode at least two interacting proteins.

In a further embodiment of the invention, a method for identifying nucleic acid sequences that encode at least two interacting proteins is provided, comprising the steps of a) combining (i) a first vector comprising (1) a nucleic acid sequence that encodes a first protein that interacts with a second protein, (2) a first restriction endonuclease recognition site specific for a restriction endonuclease that cleaves the nucleic acid sequence fragment distally to the restriction endonuclease recognition site; and (3) a second restriction endonuclease recognition site, and (ii) a second vector comprising (1) a nucleic acid sequence that encodes the second protein, (2) a third restriction endonuclease recognition site specific for a restriction endonuclease that cleaves the nucleic acid sequence fragment distally to the restriction endonuclease recognition site, and (3) a fourth restriction endonuclease recognition site, thereby producing a combination, b) optionally maintaining the combination under conditions in which the first protein and the second protein are expressed and interact, c) joining the first vector with the second vector, thereby forming a contiguous nucleic acid sequence that comprises (i) the nucleic acid sequence that encodes a first protein that interacts with a second protein, (ii) the first restriction endonuclease recognition site specific for a restriction endonuclease that cleaves the nucleic acid sequence fragment distally to the restriction endonuclease recognition site, (iii) the second restriction endonuclease recognition site, (iv) the nucleic acid sequence that encodes the second protein, (v) the third restriction endonuclease recognition site specific for a restriction endonuclease that cleaves the nucleic acid sequence fragment distally to the restriction endonuclease recognition site, and (vi) the fourth restriction endonuclease recognition site, d) cleaving the second restriction endonuclease recognition site and the fourth restriction endonuclease recognition site in the contiguous nucleic acid sequence with restriction endonucleases thereby producing compatible ends in the contiguous nucleic acid sequence, e) maintaining the contiguous nucleic acid sequence under conditions in which the compatible ends in the contiguous nucleic acid sequence intramolecularly ligate, thereby producing a circularized nucleic acid sequence, and f) sequencing the circularized nucleic acid sequence, thereby identifying nucleic acid sequences that encode at least two interacting proteins. In a particular embodiment, the cleaving of the second restriction endonuclease recognition site and the cleaving of the fourth restriction endonuclease recognition site in the contiguous nucleic acid sequence releases a fragment containing a recombined site-specific recombinase recognition site between the nucleic acid sequence that encodes a sequence from the first protein and a sequence from the second protein that interact with each other.

In another aspect of the invention, provided is a method for identifying nucleic acid sequences that encode at least two interacting proteins comprising the steps of a) combining (i) a first vector comprising (1) a nucleic acid sequence that encodes a first protein that interacts with a second protein, (2) a first restriction endonuclease recognition site specific for a restriction endonuclease that cleaves the nucleic acid sequence fragment distally to the restriction endonuclease recognition site, and (3) a second restriction endonuclease recognition site, and (ii) a second vector comprising, (1) a nucleic acid sequence that encodes the second protein, (2) a third restriction endonuclease recognition site specific for a restriction endonuclease that cleaves the nucleic acid sequence fragment distally to the restriction endonuclease recognition site, and (3) a fourth restriction endonuclease recognition site, thereby producing a combination, b) optionally maintaining the combination under conditions in which the first protein and the second protein are expressed and interact, c) joining the first vector with the second vector, thereby forming a contiguous nucleic acid sequence that comprises (i) the nucleic acid sequence that encodes a first protein that interacts with a second protein, (ii) the first restriction endonuclease recognition site specific for a restriction endonuclease that cleaves the nucleic acid sequence fragment distally to the restriction endonuclease recognition site, (iii) the second restriction endonuclease recognition site; (iv) the nucleic acid sequence that encodes the second protein, and (v) the third restriction endonuclease recognition site specific for a restriction endonuclease that cleaves the nucleic acid sequence fragment distally to the restriction endonuclease recognition site, (vi) a fourth restriction endonuclease recognition site, d) cleaving the second restriction endonuclease recognition site and the fourth restriction endonuclease recognition site in the contiguous nucleic acid sequence with restriction endonucleases, thereby producing compatible ends in the contiguous nucleic acid sequence, e) maintaining the contiguous nucleic acid sequence under conditions in which the compatible ends in the contiguous nucleic acid sequence intramolecularly ligate, thereby producing a circularized nucleic acid sequence, f) cleaving the first restriction endonuclease recognition site and the third restriction endonuclease recognition site in the circularized nucleic acid sequence with restriction endonucleases that cleave the circularized nucleic acid sequence distally to the restriction endonuclease recognition sites, thereby producing a paired tag comprising a 5' end tag and a 3' end tag of the circularized nucleic acid sequence, and g) sequencing the paired tag, thereby identifying nucleic acid sequences that encode at least two interacting proteins.

In a further embodiment of the invention, provided is a method for identifying a plurality of nucleic acid sequences that encode at least two interacting proteins comprising the steps of a) combining (i) a plurality of first vectors each comprising (1) a nucleic acid sequence that encodes a first protein that interacts with a second protein, (2) a first restriction endonuclease recognition site specific for a restriction endonuclease that cleaves the nucleic acid sequence fragment distally to the restriction endonuclease recognition site, and (3) a second restriction endonuclease recognition site, and (ii) a plurality of second vector each comprising (1) a nucleic acid sequence that encodes the second protein, (2) a third restriction endonuclease recognition site specific for a restriction endonuclease that cleaves the nucleic acid sequence fragment distally to the restriction endonuclease recognition site, and (3) a fourth restriction endonuclease recognition, thereby producing a combination comprising a plurality of first vectors and a plurality of second vectors, b) maintaining the combination under conditions in which the plurality of first vectors encoding a first protein and the plurality of second vectors encoding a second protein are expressed and the first protein and second protein interact c) selecting the combinations of a first vector that encodes a first protein and a second vector that encodes a second protein, wherein the first protein interacts with the second protein, d) joining the first vectors with the second vectors, wherein the first vectors and second vectors encode interacting proteins, thereby forming a plurality of contiguous nucleic acid sequences that each comprise (i) the nucleic acid sequence that encodes a first protein that interacts with a second protein, (ii) the first restriction endonuclease recognition site specific for a restriction endonuclease that cleaves the nucleic acid sequence fragment distally to the restriction endonuclease recognition site, (iii) the second restriction endonuclease recognition site adjacent to the first restriction endonuclease site, (iv) the nucleic acid sequence that encodes the second protein, (v) the third restriction endonuclease recognition site specific for a restriction endonuclease that cleaves the nucleic acid sequence fragment distally to the restriction endonuclease recognition site, and (vi) the fourth restriction endonuclease recognition site, d) cleaving the second restriction endonuclease recognition site and the fourth restriction endonuclease recognition site in the contiguous nucleic acid sequence with restriction endonucleases that leave compatible ends, e) maintaining the contiguous nucleic acid sequence under conditions in which the compatible ends intramolecularly ligate, thereby producing a circularized nucleic acid sequence that encodes a sequence from the first protein and a sequence from the second protein that interact with each other, f) cleaving the first restriction endonuclease recognition site and the third restriction endonuclease recognition site in each circularized nucleic acid sequence with restriction endonucleases that cleave each circularized nucleic acid sequence distally to the restriction endonuclease recognition sites, thereby producing a plurality of paired tags comprising a 5' end tag and a 3' end tag of the circularized nucleic acid sequence, g) joining the paired tags, and h) sequencing the joined paired tags, thereby identifying a plurality of nucleic acid sequences that encode at least two interacting proteins.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5 is an outline of the paired tag, two-hybrid method.

FIG. 6A-D are schematics outlining an example of a paired tag protocol. FIG. 6A is a schematic outlining the vector, and the steps of excising a stuffer fragment and preparation of inserts. FIG. 6B is a schematic outlining the steps of cloning of the inserts, optional exonuclease treatment, restriction endonuclease digestion with MmeI, and ligation to a degenerate linker. FIG. 6C is a schematic outlining the steps of PCR amplification, excising of paired tags, concatenation of paired tags and cloning of paired tags into a suitable vector, such as a sequencing vector. FIG. 6D is a list of particular nucleic acid sequences of the invention.

FIG. 12 is a schematic of one embodiment for generating paired genome sequence tags.

DETAILED DESCRIPTION OF THE INVENTION

Figure 1:
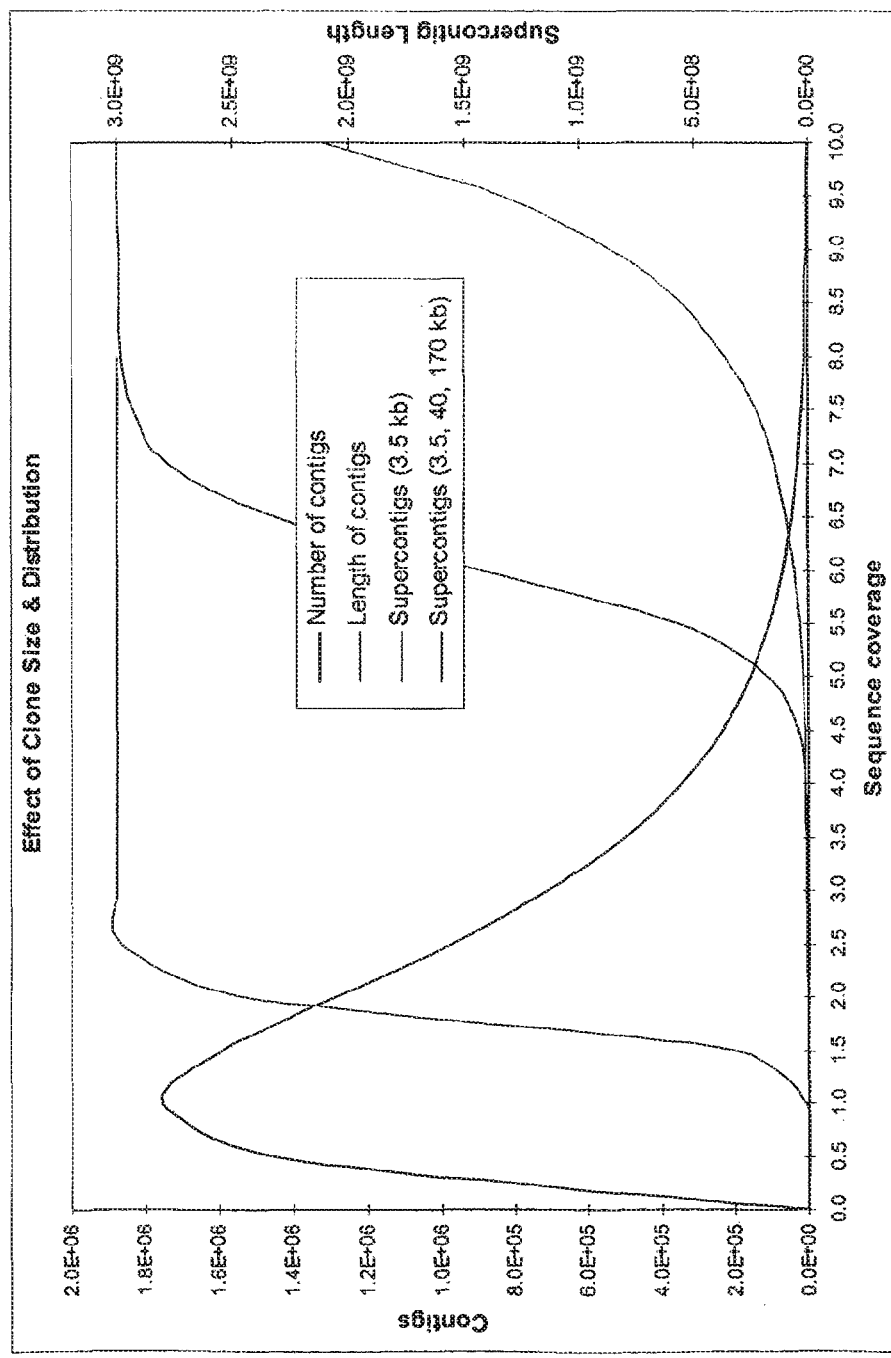
FIG. 1 is a graph depicting the effect of clone size and distribution.

The present invention provides a method for producing a paired tag from a nucleic acid sequence (also referred to herein as a nucleotide sequence). In one embodiment, the nucleic acid sequence (e.g. DNA, RNA) comprises at least two restriction endonuclease recognition sites specific for a restriction endonuclease that cleaves the nucleic acid sequence fragment distally to the restriction endonuclease recognition site. In another embodiment, the nucleic acid sequence comprises at least one restriction endonuclease recognition site specific for a restriction endonuclease that cleaves both upstream and downstream from the recognition site. The restriction endonuclease recognition sites present in the nucleic acid sequence can be the same or different. In addition, the restriction endonuclease recognition sites present in the nucleic acid sequence can be cleaved by the same or different restriction endonucleases.

The present invention also provides a method for producing a paired tag from a nucleic acid sequence, wherein the nucleic acid sequence comprises at least one recombination site, wherein a recombination event at this recombination site in the nucleic acid sequence produces a paired tag from the nucleic acid sequence.

As used herein, a "paired tag" is produced from a nucleic acid sequence and comprises a 5' end of a nucleic acid sequence (e.g., a contiguous nucleic acid sequence) paired or joined with the 3' end of the same nucleic acid sequence, wherein a portion of the internal sequence of the contiguous nucleic acid sequence is removed. In one embodiment, a paired tag can be represented as:

wherein "5'------" represents a 5' end tag, "------3'" represents a 3' end tag, and ".box-solid." represents a linker (or adapter) that links the 5' end tag to the 3' end tag. Alternatively, a paired tag can be represented as:

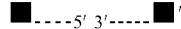

wherein "------5'" represents a 5' end tag, "3'------" represents a 3' end tag, and ".box-solid." represents an adapter (or linker). As will be recognized by the person of skill in the art, the orientation of the 5' end tag and 3' end tag can be reversed. As discussed below, the linker or adapter can comprise: at least one endonuclease recognition site, (e.g., for a restriction endonuclease enzyme such as a rare cutting enzyme, an enzyme that cleaves distally to its recognition sequence); an overhang that is compatible with joining to a complementary overhang from a restriction endonuclease digestion product; an attachment capture moiety, such as biotin; primer sites (for use in, e.g., amplification, RNA polymerase reactions); Kozak sequence, promoter sequence, (e.g. T7 or SP6); and/or an identifying moiety, such as a fluorescent label.

A paired tag is distinguished from a ditag since a ditag is a randomized pairing of two tags usually from more than one nucleic acid sequence, for example, a 5' end of sequence A and the 3' end of sequence B. In contrast, a paired tag as described herein, is not a randomized pairing of two tags, but the pairing of two tags that are produced from a single contiguous nucleic acid sequence.

Paired tags facilitate the assembly (such as whole genome assembly, or genome mapping) of a nucleic acid sequence, such as a genomic DNA sequence, even if either tag (for example, the 5' tag) is generated from a non-informative sequence (for example, a repeat sequence) and the other tag in the pair (for example, the 3' tag) is generated from an informative sequence based on the paired tag's "signature". A paired tag's signature is derived from the size of the original nucleic acid sequence from which the paired tag represents the 5' end and 3' end of the paired tag's nucleic acid sequence. The random association of tags to form ditags does not retain any signature as the two tags in the ditag generally do not represent the 5' end and 3' end of any contiguous nucleic acid sequence. In addition, a paired tag can identify the presence of an inverted nucleic acid sequence in, for example, a genomic DNA sample, because of the paired tag's signature. Randomly associated tags that form ditags cannot detect the presence of an inverted nucleic acid sequence because the ditag does not retain a signature. For example, a database version of one genome places tags in the order of: X-Y-Z-A in a contiguous sequence. Paired tags from this sequences generates the following two paired tags: X-Y and Z-A. In a comparison genome, for example, from a cancer cell, the paired tags from the same contiguous sequence generates the following two paired tags: X-Z and Y-A. These two paired tags indicates the order of the tags in the contiguous sequence of the cancer cell genome as: X-Z-Y-A. Thus, it is determined that the fragment Y-Z is inverted. Ditags will not have sufficient information to determine if a contiguous sequence has an inversion due to the random association of any two tags together.

A contiguous nucleic acid sequence is a nucleic acid sequence having a sequential sequence of nucleic acids, for example, deoxyribonucleic acids, ribonucleic acids, derivatives or analogs thereof, and combinations thereof, as will be understood by one of skill in the art.

In one embodiment, a "contiguous nucleic acid sequence" is a nucleic acid fragment. Such a nucleic acid fragment can be obtained, for example, from sheared DNA, such as genomic DNA, from enzyme-digested DNA, for example, restriction enzyme-digested or non-specific endonuclease-digested DNA, or a combination thereof, or from a modified genomic DNA fragment derived by treatment of genomic DNA, for example, with one or more nucleic acid modifying enzymes. In a further embodiment, the contiguous nucleic acid sequence comprises at least two nucleic acid sequences that encode at least two interacting proteins, wherein the at least two nucleic acid sequences have been joined to form a contiguous nucleic acid sequence.

A "5'end tag" (also referred to as a "5'tag") and a "3'end tag" (also referred to as a "3'tag") of a contiguous nucleic acid sequence can be short nucleic acid sequences, for example, the 5' end tag or 3' end tag can be from about 6 to about 80 nucleotides, from about 6 to about 600 nucleotides, from about 6 to about 1200 nucleotides or longer, from about 10 to about 80 nucleotides, from about 10 to about 1200 nucleotides, from about 10 to about 1500 nucleotides or longer in length that are from the 5' end and 3' end, respectively, of the contiguous nucleic acid sequence. In one embodiment, the 5' end tag and/or the 3' end tag are about 14 nucleotides, about 20 nucleotides or about 27 nucleotides. The 5' end tag and a 3' end tag are generally sufficient in length to identify the contiguous nucleic acid sequence from which they were produced. In one embodiment, the 5' end tag and/or the 3' end tag are produced after cleavage of the contiguous nucleic acid sequence with a restriction endonuclease having a recognition site located at the 5' and/or 3' end of the contiguous nucleic acid sequence. In a particular embodiment, the restriction endonuclease cleaves the contiguous nucleic acid sequence distally to (outside of) its restriction endonuclease recognition site. The 5'end tag and/or 3'end tag can also be produced after cleavage by other fragmentation means, such as random shearing, treatment with non-specific endonucleases or other fragmentation methods as will be understood by one skilled in the art. In some embodiments, cleavage can occur in a linker or adapter sequence, in other embodiments, cleavage can occur outside a linker or adapter sequence, such as in a genomic DNA fragment.

Traditional classification of restriction endonucleases (restriction enzymes) generally divide restriction endonucleases according to their subunit composition, cleavage position, sequence-specificity and co-factor requirements. For example, restriction endonucleases can be classified as type I, type II, type IIs, type IIB, type III or type IV restriction endonucleases. Restriction endonucleases are also characterized according to their cleavage frequency for a particular sequence, such as a genomic sequence. For example, a restriction endonuclease can be characterized as a "rare-cutting restriction endonuclease" or a "rare-cutting restriction enzyme" based on the rarity or infrequency of its recognition site in a nucleic acid sequence, e.g., a genomic sequence. Examples of rare-cutting restriction endonucleases are well known to those of skill in the art, and include, for example, AsiSI, NotI. Further examples of enzymes that are rare-cutting include homing endonucleases. Homing endonucleases are rare-cutting enzymes encoded by introns and inteins (Belfort M. and Roberts R. J., Nucleic Acids Res. 25:3379-88 (1997)). Examples of homing endonucleases include I-CeuI, I-SceI, PI-PspI and PI-SceI.

In one embodiment, the restriction endonuclease for use in the methods of the invention includes one or more restriction endonucleases that cleave a nucleic acid distally to its restriction endonuclease recognition site. As used herein, "restriction endonucleases that cleave a nucleic acid distally to its restriction endonuclease recognition site" refers to a restriction endonuclease that recognizes a particular site within a nucleic acid sequence and cleaves this nucleic acid sequence outside the region of the recognition site (cleavage occurs at a site which is distal or outside the site recognized by the restriction endonuclease). In one embodiment, a restriction endonuclease that cleaves a nucleic acid distally to its restriction endonuclease recognition site cleaves on one side of the restriction endonuclease recognition site (for example, upstream or downstream of the recognition site). In another embodiment, restriction endonuclease that cleaves a nucleic acid distally to its restriction endonuclease recognition site cleaves on both sides of the restriction endonuclease recognition site (for example, upstream and downstream of the recognition site). In another embodiment, the restriction endonuclease cleaves once between two restriction endonuclease recognition sites. Examples of such restriction endonucleases are well known in the art, and include restriction endonucleases classified as Type I (e.g., CfrA I, Eco377 I, Hind I, KpnA, IngoAV, StySK I), Type Ius (e.g., MmeI, Fok I, Bsg I, Bpm I, Mbo II, and Alw I), Type IIB (e.g. AlfI, AloI, BaeI, BcgI, BplI, BsaXI, BslFI, Bsp24I, CjeI, CjePI, CspCI, FalI, HaeIV, Hin4I, PpiI, and PsrI), Type III (e.g., EcoP I, EcoP15I, Hine I, Hinf III) and Type IV (e.g., Eco57 I, Bcg I [recently re-classified as a Type IIB], BseMII) restriction endonucleases.

The present invention provides in one embodiment, a method for producing a paired tag from a nucleic acid sequence. In one embodiment, the nucleic acid sequence comprises at least one restriction endonuclease recognition site specific for a restriction endonuclease that cleaves the nucleic acid sequence distally to the restriction endonuclease recognition site. In another embodiment, the nucleic acid sequence comprises two restriction endonuclease recognition sites specific for a restriction endonuclease that cleaves the nucleic acid sequence distally to the restriction endonuclease recognition site. In a particular embodiment, the restriction endonuclease recognition site specific for a restriction endonuclease that cleaves the nucleic acid sequence distally to the recognition site is adjacent to the nucleic acid sequence of interest. These restriction endonuclease recognition sites are cleaved using the restriction endonuclease that is specific for the restriction endonuclease recognition sites. As a result of this cleavage, a 5' end tag and a 3' end tag is produced from the nucleic acid sequence. The 5' end tag is joined with the 3' end tag of the nucleic acid sequence to produce a paired tag from the nucleic acid sequence. The two restriction endonuclease recognition sites specific for a restriction endonuclease that cleaves the nucleic acid sequence fragment distally to the restriction endonuclease recognition site can be the same or different.

In another embodiment, the invention provides a method for generating paired tags from the 5' and 3' ends of a set of genomic DNA fragments, wherein the tags are generated by fragmentation means other than by cleavage with restriction endonucleases that cleave distally to their recognition sites, for example, by random shearing or by other non-specific cleavage methods. This is achieved, for example, by performing two rounds of intramolecular ligation in which a linker is incorporated between the 5' and 3' ends of the genomic DNA fragments, with a fragmentation step performed between the first and second intramolecular ligation steps. This method produces 5' and 3' end tags of the genomic DNA fragment that can be long in length, thereby facilitating long sequence read lengths.

As used herein, "joining" refers to methods such as ligation, annealing or recombination used to adhere one component to another. Recombination can be achieved by any methods known in the art. For example, recombination can be a Cre/Lox recombination. In one embodiment, the recombination is a between a lox71 site and a lox66 site. In another embodiment, joining of a nucleic acid sequence to another nucleic acid sequence is performed by intermolecular ligation. For example, two nucleic acid sequences can be joined to form one contiguous nucleic acid sequence. A typical example of intermolecular ligation is cloning a nucleic acid sequence into a vector. A vector is generally understood in the art, and is understood to contain an origin of replication ("ori"). In another embodiment, intermolecular ligation can be achieved using a non-vector vehicle (also referred to herein as "without cloning"). Without cloning means that a joining of nucleic acid sequence is not an accomplished using vector is not used to clone into. For example, a DNA sequence or an oligonucleotide, such as a linker or an adapter can be intermolecularly ligated to the nucleic acid sequence of interest to facilitate joining of nucleic acid sequences.

In one embodiment, intermolecular ligation is between two nucleic acid sequences having sticky ends ("sticky ends ligation"). In an alternative embodiment, intermolecular ligation is between two nucleic acid sequences having blunt ends ("blunt end ligation"). In another example, intermolecular ligation is between a number of paired tags, for example, to form a concatemer. In a further embodiment, intermolecular ligation is between at least three components, such as two paired tags and a linker, or two tags and a linker. The linker functions to link two components together, for example, the linking of one or more paired tags together. As used herein, a "linker" is a nucleic acid fragment, such as DNA, as is understood in the art. The linker can be double-stranded or single-stranded. In general, the linker acts to link two components together, such as linking the 5' end of a nucleic acid sequence to the 3' end of a nucleic acid sequence. Furthermore, a linker can comprise: at least one endonuclease recognition site, (e.g., for a restriction endonuclease enzyme such as a rare cutting enzyme, an enzyme that cleaves distally to its recognition sequence); an overhang that is compatible with joining to a complementary overhang from a restriction endonuclease digestion product; an attachment moiety, such as biotin; primer sites, for use in, (e.g., amplification, RNA polymerase reactions; Kozak sequence, promoter sequence), (e.g. T7 or SP6; and/or an identifying moiety, such as a fluorescent label). A double-stranded linker can be produced by annealing two oligonucleotides, for example, and typically ranges between about 6 to about 1000 base pairs in length, but more typically is between about 30 and about 100 base pairs in length. In one embodiment, the linker provides a link between two components having non-complementary ends. In another embodiment, the linker is a degenerate linker. As used herein, a "degenerate linker" is a linker having in at least one position, a plurality of possible nucleotides, as will be understood by those of skill in the art. In a particular embodiment, the linker has the sequence NNATGATGNN (SEQ ID NO: 1), where N=any nucleotide. In another embodiment, the linker comprises a restriction endonuclease recognition site. In a particular embodiment, the linker comprises a rare cutting restriction endonuclease recognition site. For example, the linker having SEQ ID NO: 1 allows the 3' overhangs of paired tags to come together when the paired tag produces a sequence comprising "linker-5' TAG-3'TAG-linker". In another example, the linker and the paired tag produces a sequence comprising "5' TAG-linker-3'TAG". Other examples are those that generate the arrangement "linker-5' TAG-linker-3'TAG-linker". As will be recognized by one of skill in the art, any of the linker moieties can be replaced by a vector.

In another embodiment, joining of two nucleic acid sequences is performed by intramolecular ligation. Intramolecular ligation includes, for example, the ligation of the 5' end of a nucleic acid sequence fragment to the 3' end of the same nucleic acid sequence fragment. In one embodiment, intramolecular ligation produces a circular nucleic acid sequence. For example, in one embodiment, joining of a 5' end tag to the 3' end tag of a contiguous sequence is performed by intramolecular ligation. In a further embodiment, joining of a 5' end tag to the 3' end tag of a contiguous sequence is performed by intramolecular ligation, wherein the 5' end tag nucleic acid sequence and the 3' end tag nucleic acid sequence have, for example, sticky ends ("sticky ends ligation"). In another embodiment, joining of a 5' t end tag to the 3' end tag comprised in a contiguous sequence is performed by intramolecular ligation, wherein the 5' end tag nucleic acid sequence and the 3' end tag nucleic acid sequence have, for example, blunt ends ("blunt end ligation").

In one embodiment, intramolecular ligation is performed by ligation of a nucleic acid sequence fragment in the presence of a linker such that one end of the linker is first ligated to one end of the nucleic acid sequence fragment by intermolecular ligation, then the other end of the linker is ligated to the other end of the nucleic acid sequence fragment by intramolecular ligation. This results in a circular molecule in which the linker is inserted between the two ends of the nucleic acid sequence fragment. Typically, the ends of the linker and the nucleic acid sequence fragment are complementary to each other, but not to themselves to avoid self-ligation of the inserts and linkers.

In the method of the invention, conditions that favor intramolecular ligation over intermolecular ligation are used when attempting to circularize DNA molecules in order to avoid chimeric ligation (i.e., the ligation of 5' and 3' ends from two different DNA molecules which results in the production of ditags). Conditions that favor intramolecular ligation over intermolecular ligation are known in the art. In one embodiment, intramolecular ligation is favored over intermolecular ligation by performing ligation at low DNA concentrations, and also in the presence of crowding reagents like polyethylene glycol (PEG) at low salt concentrations (Pfeiffer and Zimmerman, Nucl. Acids Res. (1983) 11(22): 7853-7871). Ligation at low DNA concentration can be expensive and impractical since large reaction volumes are used at high ligase concentration but dilute DNA concentration. The use of PEG increases the reaction rate, therefore, long reaction times can still result in intermolecular products. In addition, volume exclusion does not eliminate diffusion of DNA molecules such that given enough time, DNA molecules will diffuse within reach of one another and ligate to one another. To overcome these problems, water-in-oil emulsions can be used. Water-in-oil emulsions have been described by Dressman et al. for single molecule PCR (Dressman et al., PNAS (2003), 100(15): 8817-8822). By creating a water-in-oil emulsion, billions of micro-reaction bubbles, for example, 10 micrometers in diameter, can be generated. Using a dilute enough DNA concentration can ensure that only one or less than one molecule of DNA exists in any given micro-reactor. Under such conditions, long reaction times and additives (such as PEG, MgCl.sub.2, DMSO) which increase the reaction rate of ligase (Alexander et al., Nuc. Acids Res. (2003) 31(12): 3208-3216) can be utilized without any risk of intermolecular ligation.

In one embodiment, emulsion ligation of a nucleic acid sequence fragment is performed in the presence of a linker or adapter, such that the linker or adapter is incorporated into the resulting circular molecules between the 5' and 3' ends of the nucleic acid sequence fragment. In another embodiment, emulsion ligation of a nucleic acid sequence fragment is performed in the presence of a substrate, for example, a magnetic bead coupled to a linker or adaptor, such that the resulting circularized DNA becomes immobilized (covalently or non-covalently) onto the substrate. In each of these embodiments, the concentration of nucleic acid sequence fragments, linkers, and beads can be modulated independently to maximize intramolecular ligation or, if relevant, immobilization of an individual nucleic acid sequence fragment onto a single bead.

In another embodiment, emulsion ligation of a nucleic acid sequence fragment is performed in the presence of a substrate, for example, a magnetic bead coupled to a linker or adaptor, such that the resulting circularized DNA becomes immobilized onto the substrate. In each of these embodiments, the concentration of nucleic acid sequence fragments, linkers, and beads can be modulated independently to maximize intramolecular ligation or, if relevant, immobilization of an individual nucleic acid sequence fragment onto a single bead. As used herein, "immobilized" means attached to a surface by covalent or non-covalent attachment means, as understood in the art. As used herein, a "substrate" is a solid or polymeric support such as a silicon or glass surface, a magnetic bead, a semisolid bead, a gel, or a polymeric coating applied to the another material, as is understood in the art.

Circularized nucleic acid molecules produced by intramolecular ligation with an intervening linker may be purified by a variety of methods known in the art, such as by gel electrophoresis, by treatment with an exonuclease (e.g., Bal31 or "plasmid-safe" DNase) to remove contaminating linear molecules. Nucleic acid molecules incorporating a linker between the 5' and 3' ends of the starting nucleic acid sequence fragment can be purified by affinity capture using a number of methods known in the art, such as the use of a DNA binding protein that binds to the linker specifically, by triplex hybridization using a nucleic acid sequence complementary to the linker, or by means of a biotin moiety covalently attached to the linker. Affinity capture methods typically involve the use of capture reagents attached to a substrate such as a solid surface, magnetic bead, or semisolid bead or resin.

A nucleic acid sequence, fragment, or paired tag having compatible ends are understood by one of skill in the art to mean that the ends are compatible with joining to another nucleic acid sequence, fragment or paired tag as provided herein. Compatible ends can be "sticky ends" having a 5' and/or 3' overhang, or alternatively, compatible ends can be "blunt ends" having no 5' and/or 3' overhang. Sticky ends permit sequence-dependent ligation, whereas blunt ends permit sequence-independent ligation. Compatible ends are produced by any known methods that are standard in the art. For example, compatible ends of a nucleic acid sequence are produced by restriction endonuclease digestion of the 5' and/or 3' end. In another embodiment, compatible ends of a nucleic acid sequence are produced by introducing (for example, by annealing, ligating, or recombination) an adapter to the 5' end and/or 3' end of the nucleic acid sequence, wherein the adapter comprises a compatible end, or alternatively, the adapter comprises a recognition site for a restriction endonuclease that produces a compatible end on cleavage. As used herein, an "adapter" is, for example, nucleic acid fragment, such as DNA (double stranded, single stranded), as will be understood by one of skill in the art. An adapter can be used to modify the 5' end and/or the 3' end of a nucleic acid sequence. In one embodiment, the adapter can comprise: at least one endonuclease recognition site, e.g., for a restriction endonuclease enzyme such as a rare cutting enzyme, an enzyme that cleaves distally to its recognition sequence; an overhang that is compatible with joining to a complementary overhang from a restriction endonuclease digestion product; an attachment moiety, such as biotin; and/or an identifying moiety, such as a fluorescent label. Such adapters can be produced, for example, by annealing a pair of oligonucleotides having the appropriate nucleic acid sequences. In another embodiment, compatible ends of a nucleic acid sequence are produced by introducing (for example, by annealing, ligating, or recombination) the nucleic acid sequence into a vector. In one embodiment, the nucleic acid sequence is cloned into a vector, wherein the vector comprises at least one recognition site for a restriction endonuclease in proximity, for example, adjacent to where the nucleic acid sequence is cloned into, and wherein the recognition site produces a compatible end on cleavage.

In some aspects of the invention as disclosed herein, the use of an adapter or a linker can be used interchangeably, as will be understood by the person of skill in the art.

As used herein, a "vector" is, for example, a plasmid, phage or phagemid, as will be understood by one of skill in the art. A vector as is understood by one of skill in the art to contain an origin of replication ("ori") for DNA replication in a host organism (for example, E. coli). As used herein, "cloning" is the propagation of a nucleic acid sequence in a vector in a viable host cell, such as E. coli, as will be understood by one of skill in the art.

A variety of in vitro amplification methods are known in the art, including the polymerase chain reaction, "PCR", and amplification methods that can be performed under isothermal conditions, collectively referred to as "isothemal amplification", which include, for example, rolling circle amplification (RCA), strand displacement amplification (SDA), multiple displacement amplification (MDA), and methods involving the use of a DNA dependent RNA polymerase (such as T7 RNA polymerase) and RNaseH. Compositions comprising paired tags and introduced nucleic acid sequences, such as linkers, adapters, or vectors can readily be amplified in vitro by using such methods. Furthermore, it is well understood in the art that nucleic acid sequences may be amplified on substrates if one of the primers used in the amplification is immobilized on the substrate.

In another embodiment of the invention, a method is provided for producing a paired tag from a nucleic acid sequence, wherein the nucleic acid sequence comprises two restriction endonuclease recognition sites specific for a restriction endonuclease that cleaves the nucleic acid sequence distally to the restriction endonuclease recognition site, and at least two restriction endonuclease recognition sites specific for a rare cutting restriction endonuclease. In one embodiment, endonuclease recognition sites specific for a rare cutting restriction endonuclease occur minimally in a sequence (e.g. once, twice, etc.) are specifically recognized by a single rare (unique) cutting restriction endonuclease. In another embodiment, endonuclease recognition sites specific for a rare cutting restriction endonuclease are specifically recognized by multiple rare cutting restriction endonuclease. Thus, in one embodiment of the invention, a method is provided for producing a paired tag from a nucleic acid sequence comprising cleaving the nucleic acid sequence using the restriction endonuclease that cleaves the nucleic acid sequence distally to the restriction endonuclease recognition sites, thereby producing a 5' end tag and a 3' end tag from the nucleic acid sequence. The 5' end tag is joined with the 3' end tag of the nucleic acid sequence to produce a paired tag from the nucleic acid sequence. The paired tag can be further cleaved with a rare cutting restriction endonuclease, which produces a paired tag having compatible ends.

In an alternative embodiment, the present invention is drawn to a method for producing a paired tag from a nucleic acid sequence that comprises at least one restriction endonuclease recognition site specific for a restriction endonuclease that cleaves the nucleic acid sequence distally to the restriction endonuclease recognition site, and at least two restriction endonuclease recognition sites specific for a rare cutting restriction endonuclease. The nucleic acid sequence is cleaved with the rare cutting restriction endonuclease restriction endonuclease to produce nucleic acid sequence fragments that have compatible ends and which nucleic acid sequence fragments comprise at least one restriction endonuclease recognition site specific for a restriction endonuclease that cleaves distally to the recognition site. The fragments are intramolecularly ligated to produce a circularized nucleic acid sequence. The circularized nucleic acid sequences are cleaved with the restriction endonuclease that cleaves the nucleic acid sequence distally to the restriction endonuclease recognition site which results in the production of a paired tag comprising a 5' end tag of the nucleic acid sequence and a 3' end tag of the nucleic acid sequence.

A nucleic acid sequence that comprises two restriction endonuclease recognition sites specific for a restriction endonuclease that cleaves the nucleic acid sequence distally to the restriction endonuclease recognition site, and/or at least one restriction endonuclease recognition sites specific for a rare cutting restriction endonuclease can be naturally-occurring, or prepared using techniques that are standard in the art. Methods for introducing into the 5' end and/or into the 3' end of a nucleic acid sequence fragment a restriction endonuclease recognition site are well known in the art. For example, in one embodiment, a method for introducing into the 5' end and/or into the 3' end of a nucleic acid sequence fragment a restriction endonuclease recognition site comprises joining (e.g., ligating or annealing) to the 5' end and/or to the 3' end a nucleic acid sequence that comprises the restriction endonuclease recognition site or, alternatively, forms the restriction endonuclease recognition site once joined to the 5' end and/or to the 3' end of the nucleic acid sequence fragment. In another embodiment, a method for introducing a restriction endonuclease recognition site into the 5' end and/or into the 3' end of a nucleic acid sequence fragment comprises cloning the nucleic acid sequence fragment into a vector, wherein the 5' end and/or 3' end of the nucleic acid sequence fragment are cloned adjacent to one or more restriction endonuclease recognition sites present in the vector. Alternatively, in another embodiment, a method for introducing a restriction endonuclease recognition site into the 5' end and/or into the 3' end of a nucleic acid sequence fragment comprises cloning the nucleic acid sequence fragment into a vector, wherein the 5' end and/or 3' end of the nucleic acid sequence fragment once cloned into the vector produces one or more restriction endonuclease recognition sites at the 5' end and/or 3' end of the nucleic acid sequence fragment.

A nucleic acid sequence fragment can be prepared by a variety of methods. These methods are generally referred to herein as the "fragmenting" of a nucleic acid sequence. For example, fragmenting of a nucleic acid sequence can be achieved by shearing (e.g. by mechanical means such as nebulization, hydrodynamic shearing through a small orifice, or sonication) the nucleic acid sequence or digesting the nucleic acid sequence with an enzyme, such as a restriction endonuclease or a non-specific endonuclease. The nucleic acid sequence fragments obtained can be of any size (e.g., molecular weight, length, etc.). In one embodiment, nucleic acid sequence fragments of a specific size (e.g., approximately greater than about 1 mb, about 200 kb, about 100 kb, about 80 kb, about 40 kb, about 20 kb, about 10 kb, about 3 kb, about 1.5 kb, about 1 kb, about 500 bases, about 200 bases and ranges thereof) are isolated, for example, by gel electrophoresis purification and extraction, by filtration methods, such as column filtration, or by other size fractionation methods that are standard in the art.

The production of a paired tag from a nucleic acid sequence has many applications. Provided in one embodiment of the invention is a method for characterizing a nucleic acid sequence. In a particular embodiment, characterizing a nucleic acid sequence comprises sequencing the paired tags produced from the nucleic acid sequence. Sequencing methods are standard in the art, and include, for example, traditional sequencing using the Maxam and Gilbert technique or the Sanger method, or by hybridization to an array or microarray of known oligonucleotides on, for example, a chip. Alternative approaches include sequencing by synthesis methods in which primer-template complexes are immobilized, for example, to a substrate such as a polymer, a magnetic bead, or a solid surface, and are extended using a DNA polymerase or DNA ligase in the presence of labeled substrates such that the addition products can be characterized to determine the DNA sequence.

In one embodiment, the nucleic acid sequence to be characterized is a genome. A genome is the genomic DNA of a cell or organism. In one embodiment, the genome is of a prokaryote, eukaryote, plant, virus, fungus, or an isolated cell thereof. In another embodiment, the genome is a known (previously characterized or sequenced) genome. In a further embodiment, the genome is an unknown (not previously characterized or sequenced) genome. In one embodiment, characterizing a genome comprises karyotyping the genome. Karyotyping is the analysis of the genome of a cell or organism. In another embodiment, characterizing the genome comprises polymorphism discovery or genotyping to identify differences between two or more nucleic acid sequences derived from different sources.

In one embodiment of the invention, a method for characterizing a nucleic acid sequence is provided which comprises fragmenting a nucleic acid sequence to produce a plurality of nucleic acid sequence fragments having a 5' end and a 3' end. A restriction endonuclease that cleaves the nucleic acid sequence fragment distally to the restriction endonuclease recognition site and a restriction endonuclease recognition site specific for a rare cutting restriction endonuclease are introduced into the 5' end and into the 3' end (either upstream or downstream as appropriate) of each nucleic acid sequence fragment to produce modified nucleic acid sequence fragments. The modified nucleic acid sequence fragments are cleaved with the rare cutting restriction endonuclease specific for the previously introduced rare cutting restriction endonuclease recognition site, which produces a plurality of nucleic acid sequence fragments having compatible ends. The fragments are intramolecularly ligated to produce a plurality of circularized nucleic acid sequences comprising the two restriction endonuclease recognition sites specific for restriction endonucleases that cleave the nucleic acid fragment distally to the restriction endonuclease recognition sites. The circularized nucleic acid sequences are cleaved at the restriction endonuclease recognition sites with the restriction endonucleases specific for the restriction endonuclease recognition sites to produce a plurality of paired tags comprising a 5' end tag and a 3' end tag of the nucleic acid fragment. These the paired tags are characterized, which thus characterizes the nucleic acid sequence of interest.

In an alternative embodiment of the invention, a method for characterizing a nucleic acid sequence comprises, fragmenting a nucleic acid sequence to produce a plurality of nucleic acid sequence fragments having a 5' end and a 3' end. A restriction endonuclease recognition site specific for a restriction endonuclease that cleaves the nucleic acid fragment distally to the restriction endonuclease recognition site is introduced into the 5' end and into the 3' end of each nucleic acid sequence fragment, thus producing a plurality of modified nucleic acid sequence fragments. The modified nucleic acid sequence fragments are, for example, cloned into a vector. The cloned nucleic acid sequence fragments are cleaved at the restriction endonuclease recognition sites at the 5' end and the 3' end of the cloned nucleic acid sequence fragments using the restriction endonuclease that is specific for the restriction endonuclease recognition sites, which produces a 5' end tag and a 3' end tag of each cloned nucleic acid sequence fragment. The 5' end tag and a 3' end tag of each cloned nucleic acid sequence fragment are joined to produce a plurality of paired tags which can be characterized, thereby permitting the characterizing of the nucleic acid sequence.

In another embodiment of the invention, a method for characterizing a nucleic acid sequence comprises, fragmenting a nucleic acid sequence to produce a plurality of nucleic acid sequence fragments having a 5' end and a 3' end. A restriction endonuclease recognition site specific for a restriction endonuclease that cleaves the nucleic acid fragment distally to the restriction endonuclease recognition site is introduced into the 5' end and into the 3' end of each nucleic acid sequence fragment, thus producing a plurality of modified nucleic acid sequence fragments. The modified nucleic acid sequence fragments are intramolecularly ligated to produce circularized modified nucleic acid sequence fragments. Intramolecular ligation can be achieved, for example, by emulsion ligation. The circularized modified nucleic acid sequence fragments are cleaved at the restriction endonuclease recognition sites introduced at the 5' end and the 3' end of the modified nucleic acid sequence fragments using the restriction endonuclease specific for the restriction endonuclease recognition sites, which produces a 5' end tag and a 3' end tag of each modified nucleic acid sequence fragment. The 5' end tag and a 3' end tag of each nucleic acid sequence fragment are joined (i.e., concatemerized) to produce a plurality of paired tags (i.e., a concatemer) which can be characterized, thereby permitting the characterizing of the nucleic acid sequence.

In a further embodiment of the invention, a method for characterizing a nucleic acid sequence comprises, fragmenting a nucleic acid sequence to produce a plurality of nucleic acid sequence fragments having a 5' end and a 3' end. Each nucleic acid sequence fragment is cloned to introduce into the 5' end and into the 3' end of each cloned nucleic acid sequence fragment, a restriction endonuclease recognition site specific for a restriction endonuclease that cleaves the nucleic acid sequence fragment distally to the restriction endonuclease recognition site. The cloned fragments are cleaved at the restriction endonuclease recognition sites at the 5' end and the 3' end of each cloned nucleic acid sequence fragment using the restriction endonuclease that is specific for the restriction endonuclease recognition sites, thereby producing a 5' end tag and a 3' end tag of the cloned nucleic acid fragments. The 5' end tag and the 3' end tag of each cloned nucleic acid are joined to produce a plurality of paired tags. These paired tags can now be characterized, thereby characterizing the nucleic acid sequence.

In another embodiment of the invention, a method for characterizing a nucleic acid sequence comprises fragmenting a nucleic acid sequence to produce a plurality of nucleic acid sequence fragments having a 5' end and a 3' end. One or more linkers and/or adapters are joined to the ends, and an intramolecular ligation step is performed to produce a plurality of circularized nucleic acid sequences, wherein an intervening linker is introduced between the 5'end and the 3'end a nucleic acid sequence fragment. The circularized molecules are fragmented by random shearing or by other means and an adapter is joining to the ends of the fragments to produce a plurality of linear nucleic acid molecules wherein an adapter is introduced at each end. The resulting nucleic acid molecules containing the 5' and 3'ends of a nucleic acid sequence fragment (paired tag) are amplified by PCR using a universal primer complementary to the adapter sequences. The paired tags are then characterized, thereby characterizing the nucleic acid sequence.

In an alternative embodiment of the invention a method for characterizing a nucleic acid sequence comprises fragmenting a nucleic acid sequence to produce a plurality of nucleic acid sequence fragments having a 5' end and a 3' end. One or more linkers and/or adapters are joined to the ends, and an intramolecular ligation is performed to produce a plurality of circularized nucleic acid sequences, wherein an intervening first linker is introduced between the 5'end and the 3'end a nucleic acid sequence fragment. The circularized molecules are fragmented by random shearing or by other means, and adapters are joined to the ends of the fragments. A second intramolecular ligation is performed to produce a plurality of circularized nucleic acid sequences, wherein an intervening second linker is introduced between the ends of the fragments, wherein the second linker comprises two priming sites. The molecules containing the 5' and 3'ends of a nucleic acid sequence fragment (the paired tag) are amplified by PCR using two different primers that are complementary to the priming sites in the second linker. The paired tags are then characterized, thereby characterizing the nucleic acid sequence.

In another embodiment of the invention a method for characterizing a nucleic acid sequence comprises fragmenting a nucleic acid sequence to produce a plurality of nucleic acid sequence fragments having a 5' end and a 3' end. One or more linkers and/or adapters are joined to the ends, and an intramolecular ligation is performed to produce a plurality of circularized nucleic acid sequences, wherein an intervening first linker is introduced between the 5'end and the 3'end a nucleic acid sequence fragment. The circularized molecules are fragmented by random shearing or by other means, and adapters are joined to the ends of the fragments. A second intramolecular ligation is performed to produce a plurality of circularized nucleic acid sequences, wherein an intervening second linker is introduced between the ends of the fragments, wherein the second linker comprises two priming sites separated by a rare-cutting restriction endonuclease cleavage site. The molecules containing the 5' and 3'ends of a nucleic acid sequence fragment (the paired tag) are cleaved using a rare-cutting restriction endonuclease that recognizes the cleavage site in the linker. Linearization of the circular DNA molecules is not required, but improves the efficiency of PCR amplification in the next step. The resulting linear molecules are amplified by PCR using two different primers that are complementary to the priming sites in the second linker. The paired tags are then characterized, thereby characterizing the nucleic acid sequence.

In an alternate embodiment of the invention a method for characterizing a nucleic acid sequence comprises fragmenting a nucleic acid sequence to produce a plurality of nucleic acid sequence fragments having a 5' end and a 3' end. One or more linkers and/or adapters are joined to the ends, and an intramolecular ligation is performed to produce a plurality of circularized nucleic acid sequences, wherein an intervening first linker containing a sequence or chemical moiety that enables affinity capture is introduced between the 5end and the 3'end a nucleic acid sequence fragment. The circularized molecules are fragmented by random shearing or by other means, and adapters are joined to the ends of the fragments. The molecules containing the 5' and 3'ends of a nucleic acid sequence fragment are purified by affinity capture using a reagent specific for the first linker. A second intramolecular ligation is then performed to produce a plurality of circularized nucleic acid sequences, wherein an intervening second linker is introduced between the ends of the fragments, wherein the second linker comprises two priming sites. The molecules containing the 5' and 3'ends of a nucleic acid sequence fragment (the paired tag) are amplified by PCR using two different primers that are complementary to the priming sites in the second linker. The paired tags are then characterized, thereby characterizing the nucleic acid sequence.

A second purification step, for example, by affinity capture using a reagent specific for a sequence in the first linker, may be added prior to PCR amplification. Alternatively, the first purification step could be omitted and a single purification step could be performed prior to PCR amplification.

In another embodiment of the invention a method for characterizing a nucleic acid sequence comprises fragmenting a nucleic acid sequence to produce a plurality of nucleic acid sequence fragments having a 5' end and a 3' end. One or more linkers and/or adapters are joined to the ends, and an intramolecular ligation is performed to produce a plurality of circularized nucleic acid sequences, wherein an intervening first linker containing a sequence or chemical moiety that enables affinity capture is introduced between the 5'end and the 3'end a nucleic acid sequence fragment. The circularized molecules are fragmented by random shearing or by other means, and adapters are joined to the ends of the fragments. The molecules containing the 5' and 3'ends of a nucleic acid sequence fragment are purified by affinity capture using a reagent specific for the first linker. A second intramolecular ligation is then performed to produce a plurality of circularized nucleic acid sequences, wherein an intervening second linker is introduced between the ends of the fragments, wherein the second linker comprises two priming sites separated by a rare-cutting restriction endonuclease cleavage site. The molecules containing the 5' and 3'ends of a nucleic acid sequence fragment (the paired tag) are cleaved using a rare-cutting restriction endonuclease that recognizes the cleavage site in the linker. Linearization of the circular DNA molecules is not required, but improves the efficiency of PCR amplification in the next step. The resulting linear molecules are amplified by PCR using two different primers that are complementary to the priming sites in the second linker. The paired tags are then characterized, thereby characterizing the nucleic acid sequence. When two intramolecular ligation steps are performed, both the 5'end and the 3'end of a nucleic acid sequence fragment paired tag can be sequenced from the same DNA strand by using separate primers that are complementary to the sequences in the first and second linkers. The use of two distinct PCR primers enables amplification on a substrate (e.g., on the surface of a chip or a magnetic bead) wherein only one of the two primers is attached to the substrate, which results in all of the molecules being amplified in a unique orientation with respect to the substrate.

In a further embodiment of the invention, a method is provided for identifying nucleic acid sequences that encode at least two interacting proteins. Typically, this method comprises combining (1) a first vector that comprises a nucleic acid sequence that encodes a first protein that interacts with a second protein and a first restriction endonuclease recognition site specific for a restriction endonuclease that cleaves the nucleic acid sequence fragment distally to the restriction endonuclease recognition site and (2) a second vector that comprises a nucleic acid sequence that encodes the second protein and a second restriction endonuclease recognition site specific for a restriction endonuclease that cleaves the nucleic acid sequence fragment distally to the restriction endonuclease recognition site. Typically, this combination of vectors is maintained under conditions in which the first protein and the second protein are expressed and interact. Once interacting first and second interacting proteins are identified, the first and second vectors encoding same are selected for identification. Identification of interacting proteins use methods that are standard in the art (e.g., 2 or 3 hybrid systems such as yeast, bacteria and mammalian). The vectors encoding the two interacting proteins are joined to form a contiguous nucleic acid sequence which comprises the nucleic acid sequence that encodes the first protein, the first restriction endonuclease recognition site specific for a restriction endonuclease that cleaves the nucleic acid sequence fragment distally to the restriction endonuclease recognition site, the nucleic acid sequence that encodes the second protein, and the second restriction endonuclease recognition site specific for a restriction endonuclease that cleaves the nucleic acid sequence fragment distally to the restriction endonuclease recognition site. This contiguous nucleic acid sequence is cleaved at the first and second restriction endonuclease recognition sites with restriction endonucleases that cleave the contiguous nucleic acid sequence distally to the restriction endonuclease recognition sites to produce a 5' end tag and a 3' end tag of the contiguous nucleic acid sequence. The 5' end tag is joined to the 3' end tag to produce a paired tag which can be sequenced, thereby identifying the nucleic acid sequences that encode the at least two interacting proteins. In one embodiment, the paired tag produced from one combination of vectors that encode at least two interacting proteins can be joined with one or more paired tags produced from other combinations of vectors that encode at least two interacting proteins, to produce a concatemer that can be sequenced. Sequencing of such concatemers provides for high throughput analyses and increased efficiency.

In another embodiment of the invention, a method for identifying nucleic acid sequences that encode at least two interacting proteins is provided. This method provides combining a first vector which can comprise (1) a nucleic acid sequence that encodes a first protein that interacts with a second protein and (2) a first restriction endonuclease recognition site specific for a restriction endonuclease that cleaves the nucleic acid sequence fragment distally to the restriction endonuclease recognition site and a second vector which can comprise (1) a nucleic acid sequence that encodes the second protein, and (2) a second restriction endonuclease recognition site specific for a restriction endonuclease that cleaves the nucleic acid sequence fragment distally to the restriction endonuclease recognition site, which produces a combination. The combination is maintained under conditions the first protein and the second protein are expressed and interact. The first vector and second vector are joined to form a contiguous nucleic acid sequence that comprises (i) the nucleic acid sequence that encodes a first protein that interacts with a second protein, (ii) the first restriction endonuclease recognition site specific for a restriction endonuclease that cleaves the nucleic acid sequence fragment distally to the restriction endonuclease recognition site, (iii) the nucleic acid sequence that encodes the second protein, and (iv) the second restriction endonuclease recognition site specific for a restriction endonuclease that cleaves the nucleic acid sequence fragment distally to the restriction endonuclease recognition site. The contiguous nucleic acid sequence is sequenced, thereby identifying nucleic acid sequences that encode at least two interacting proteins.

In an alternative embodiment of the invention, a method for identifying nucleic acid sequences that encode at least two interacting proteins is provided. The method combines a first vector which can comprise (1) a nucleic acid sequence that encodes a first protein that interacts with a second protein, and (2) a first restriction endonuclease recognition site specific for a restriction endonuclease that cleaves the nucleic acid sequence fragment distally to the restriction endonuclease recognition site and a second vector which can comprise (1) a nucleic acid sequence that encodes the second protein and (2) a second restriction endonuclease recognition site specific for a restriction endonuclease that cleaves the nucleic acid sequence fragment distally to the restriction endonuclease recognition site, which produces a combination. The combination is maintained under conditions in which the first protein and the second protein are expressed and interact. The first vector is joined with the second vector, thereby forming a contiguous nucleic acid sequence that comprises (i) the nucleic acid sequence that encodes a first protein that interacts with a second protein, (ii) the first restriction endonuclease recognition site specific for a restriction endonuclease that cleaves the nucleic acid sequence fragment distally to the restriction endonuclease recognition site, (iii) the nucleic acid sequence that encodes the second protein and (iv) the second restriction endonuclease recognition site specific for a restriction endonuclease that cleaves the nucleic acid sequence fragment distally to the restriction endonuclease recognition site. The first restriction endonuclease recognition site and the second restriction endonuclease recognition site in the contiguous nucleic acid sequence are cleaved with restriction endonucleases that cleave the contiguous nucleic acid sequence distally to the restriction endonuclease recognition sites, thereby producing a paired tag comprising a 5' end tag and a 3' end tag of the contiguous nucleic acid sequence. The paired tag is sequenced, thereby identifying nucleic acid sequences that encode at least two interacting proteins.

In a further embodiment of the invention, a method is provided for identifying a plurality of nucleic acid sequences that encode at least two interacting proteins. In a particular embodiment, the method provides for screening multiple nucleic acids, such as, for example, a library of nucleic acids, as will be appreciated by one of skill in the art. The method comprises combining a plurality of first vectors each can comprise (1) a nucleic acid sequence that encodes a first protein that interact with a second protein and (2) a first restriction endonuclease recognition site specific for a restriction endonuclease that cleaves the nucleic acid sequence fragment distally to the restriction endonuclease recognition site and a plurality of second vectors each comprising (1) a nucleic acid sequence that encodes the second protein and (2) a second restriction endonuclease recognition site specific for a restriction endonuclease that cleaves the nucleic acid sequence fragment distally to the restriction endonuclease recognition site, thereby producing a combination comprising a plurality of first vectors and a plurality of second vectors. The combination is maintained under conditions in which the plurality of first vectors encoding a first protein and the plurality of second vectors encoding a second protein are expressed and the first protein and second protein interact. The first vectors are joined with the second vectors, wherein the first vectors and second vectors encode interacting proteins, thereby forming a plurality of contiguous nucleic acid sequences. The plurality of contiguous nucleic acid sequences each comprise (i) the nucleic acid sequence that encodes a first protein that interacts with a second protein, (ii) the first restriction endonuclease recognition site specific for a restriction endonuclease that cleaves the nucleic acid sequence fragment distally to the restriction endonuclease recognition site, (iii) the nucleic acid sequence that encodes the second protein and (iv) the second restriction endonuclease recognition site specific for a restriction endonuclease that cleaves the nucleic acid sequence fragment distally to the restriction endonuclease recognition site. In each contiguous nucleic acid sequence, the first restriction endonuclease recognition site and the second restriction endonuclease recognition site are cleaved with the restriction endonucleases that cleave the contiguous nucleic acid sequence distally to the restriction endonuclease recognition sites, thereby producing a plurality of paired tags comprising a 5' end tag and a 3' end tag of the contiguous nucleic acid sequence. The paired tags are joined and sequenced, thereby identifying a plurality of nucleic acid sequences that encode at least two interacting proteins.

Also provided in the invention is a method for identifying nucleic acid sequences that encode at least two interacting proteins comprising combining a first vector which can comprise (1) a nucleic acid sequence that encodes a first protein that interacts with a second protein and (2) a first restriction endonuclease recognition site specific for a restriction endonuclease that cleaves the nucleic acid sequence fragment distally to the restriction endonuclease recognition site and (3) a second restriction endonuclease recognition site, which in one embodiment, can be adjacent to the first restriction endonuclease recognition site and a second vector which can comprise (1) a nucleic acid sequence that encodes the second protein (2) a third restriction endonuclease recognition site specific for a restriction endonuclease that cleaves the nucleic acid sequence fragment distally to the restriction endonuclease recognition site, and (3) a fourth restriction endonuclease recognition site, which in one embodiment, can be adjacent to the third restriction endonuclease recognition site, thereby producing a combination. The combination is maintained under conditions in which the first protein and the second protein are expressed and interact. The first vector is joined with the second vector, thereby forming a contiguous nucleic acid sequence that comprises (i) the nucleic acid sequence that encodes a first protein that interacts with a second protein, (ii) the first restriction endonuclease recognition site specific for a restriction endonuclease that cleaves the nucleic acid sequence fragment distally to the restriction endonuclease recognition site, (iii) the second restriction endonuclease recognition site, (iv) the nucleic acid sequence that encodes the second protein, (v) the third restriction endonuclease recognition site specific for a restriction endonuclease that cleaves the nucleic acid sequence fragment distally to the restriction endonuclease recognition site, and (vi) the fourth restriction endonuclease recognition site. The second restriction endonuclease recognition site and the fourth restriction endonuclease recognition site in the contiguous nucleic acid sequence are cleaved with restriction endonucleases to produce compatible ends in the contiguous nucleic acid sequence. The nucleic acid sequence is maintained under conditions in which the compatible ends in the contiguous nucleic acid sequence intramolecularly ligate, thereby producing a circularized nucleic acid sequence. The circularized nucleic acid sequence is sequenced, thereby identifying nucleic acid sequences that encode at least two interacting proteins.

In a further embodiment of the invention, a method for identifying nucleic acid sequences that encode at least two interacting proteins is provided. The method comprises combining a first vector which can comprise (1) a nucleic acid sequence that encodes a first protein that interacts with a second protein, (2) a first restriction endonuclease recognition site specific for a restriction endonuclease that cleaves the nucleic acid sequence fragment distally to the restriction endonuclease recognition site; and (3) a second restriction endonuclease recognition site, which in one embodiment, can be adjacent to the first restriction endonuclease recognition site and a second vector which can comprise (1) a nucleic acid sequence that encodes the second protein (2) a third restriction endonuclease recognition site specific for a restriction endonuclease that cleaves the nucleic acid sequence fragment distally to the restriction endonuclease recognition site and (3) a fourth restriction endonuclease recognition site, which in one embodiment, can be adjacent to the third restriction endonuclease recognition site, thereby producing a combination. The combination is maintained under conditions in which the first protein and the second protein are expressed and interact. The first vector is joined with the second vector, thereby forming a contiguous nucleic acid sequence that comprises (i) the nucleic acid sequence that encodes a first protein that interacts with a second protein, (ii) the first restriction endonuclease recognition site specific for a restriction endonuclease that cleaves the nucleic acid sequence fragment distally to the restriction endonuclease recognition site, (iii) the second restriction endonuclease recognition site, (iv) the nucleic acid sequence that encodes the second protein, (v) the third restriction endonuclease recognition site specific for a restriction endonuclease that cleaves the nucleic acid sequence fragment distally to the restriction endonuclease recognition site and (vi) a fourth restriction endonuclease recognition site. The second restriction endonuclease recognition site and the fourth restriction endonuclease recognition site in the contiguous nucleic acid sequence are cleaved with restriction endonucleases, thereby producing compatible ends in the contiguous nucleic acid sequence. The contiguous nucleic acid sequence is maintained under conditions in which the compatible ends in the contiguous nucleic acid sequence intramolecularly ligate, thereby producing a circularized nucleic acid sequence. The first restriction endonuclease recognition site and the third restriction endonuclease recognition site in the circularized nucleic acid sequence are cleaved with restriction endonucleases that cleave the circularized nucleic acid sequence distally to the restriction endonuclease recognition sites, thereby producing a paired tag comprising a 5' end tag and a 3' end tag of the circularized nucleic acid sequence. The paired tag is sequenced, thereby identifying nucleic acid sequences that encode at least two interacting proteins.

Further provided in the invention is a method for identifying a plurality of nucleic acid sequences that encode at least two interacting proteins. The method comprises combining a plurality of first vectors each can comprise (1) a nucleic acid sequence that encodes a first protein that interacts with a second protein, (2) a first restriction endonuclease recognition site specific for a restriction endonuclease that cleaves the nucleic acid sequence fragment distally to the restriction endonuclease recognition site, and (3) a second restriction endonuclease recognition site, which in one embodiment, can be adjacent to the first restriction endonuclease recognition site and a plurality of second vector each comprising (1) a nucleic acid sequence that encodes the second protein, (2) a third restriction endonuclease recognition site specific for a restriction endonuclease that cleaves the nucleic acid sequence fragment distally to the restriction endonuclease recognition site and (3) a fourth restriction endonuclease recognition site, which in one embodiment, can be adjacent to the third restriction endonuclease recognition site, thereby producing a combination comprising a plurality of first vectors and a plurality of second vector. The combination is maintained under conditions in which the plurality of first vectors encoding a first protein and the plurality of second vectors encoding a second protein are expressed and the first protein and second protein interact. The first vectors are joined the second vectors, wherein the first vectors and second vectors encode interacting proteins, thereby forming a plurality of contiguous nucleic acid sequences that each can comprise (i) the nucleic acid sequence that encodes a first protein that interacts with a second protein, (ii) the first restriction endonuclease recognition site specific for a restriction endonuclease that cleaves the nucleic acid sequence fragment distally to the restriction endonuclease recognition site, (iii) the second restriction endonuclease recognition site, which in one embodiment, can be adjacent to the first restriction endonuclease recognition site, (iv) the nucleic acid sequence that encodes the second protein, (v) the third restriction endonuclease recognition site specific for a restriction endonuclease that cleaves the nucleic acid sequence fragment distally to the restriction endonuclease recognition site, and (vi) the fourth restriction endonuclease recognition site, which in one embodiment, can be adjacent to the third restriction endonuclease recognition site. The second restriction endonuclease recognition site and the fourth restriction endonuclease recognition site in the contiguous nucleic acid sequence are cleaved with restriction endonucleases that produce compatible ends. The contiguous nucleic acid sequence with compatible ends is maintained under conditions in which the compatible ends intramolecularly ligate, thereby producing a circularized nucleic acid sequence that encodes a sequence from the first protein and a sequence from the second protein that interact with each other. The first restriction endonuclease recognition site and the third restriction endonuclease recognition site in each circularized nucleic acid sequence is cleaved with restriction endonucleases that cleave each contiguous nucleic acid sequence distally to the restriction endonuclease recognition sites, thereby producing a plurality of paired tags comprising a 5' end tag and a 3' end tag of the circularized nucleic acid sequence. The paired tags are joined and sequenced, thereby identifying a plurality of nucleic acid sequences that encode at least two interacting proteins.

In one embodiment of the invention, joining is a site-specific intermolecular recombination. In another embodiment, joining is a site-specific intermolecular recombination at mutant site specific recombinase recognition sites, wherein recombination produces recombined sites having a decreased ability to subsequently recombine. In a further embodiment of the invention, the joining is site-specific intermolecular recombination between a lox71 site and a lox66 site. In a still further embodiment, cleaving the second restriction endonuclease recognition site and cleaving the fourth restriction endonuclease recognition site in the contiguous nucleic acid sequence releases a fragment containing a recombined site-specific recombinase recognition site between the nucleic acid sequence that encodes a sequence from the first protein and a sequence from the second protein that interact with each other.

Example 1

Whole Genome Assembly

The whole genome shotgun sequencing, assembly and finishing paradigm is generally the strategy of choice for microbial and fungal genome sequencing. Contrary to the expectations of some, recent advances in the development and application of whole genome assembly (WGA) software, such as Arachne, the Celera Assembler, Phusion, or Jazz, have also demonstrated that it is straightforward to produce a high quality assembly of plant and mammalian genomes using such tools (Mural, Adams et al. 2002; Jaffe, Butler et al. 2003). The cost-advantages and simplicity of the whole genome approach relative to a BAC based or hybrid sequencing strategy argue strongly for its continued development and application in future sequencing projects. One problem with the BAC based approaches is the high cost and operational burden associated with the production of 15,000-25,000 individual BAC subclone libraries, the 15-20% waste associated with re-sequencing the vector as well as the unavoidable E. coli contamination, the need to deal with transposon and bacteriophage insertions, and the 20-50% waste in redundant sequencing of BAC overlaps. Although these costs can be reduced by sequencing the BACs at low coverage (using a hybrid BAC/WGS strategy, for example) or by using a pooling strategy, they cannot be eliminated. The need to generate a physical map by using restriction digest fingerprinting or by complex pooling and sequence based mapping strategies adds additional cost and operational overhead.

For genomic sequencing and assembly, the preferred library that is constructed has a narrow fragment size distribution (Jaffe et al.). Using restriction enzyme digestion can lead to a reduced representation library because of the difficulty in size selection of a restriction-digested genome (Altshuler et al.). For a particular size range of genomic fragments to be achieved, restriction enzyme recognition sites are necessary to be spaced appropriately in order to achieve the desired results. In contrast, physical shearing permits the whole genome to be fragmented into a particular size range regardless of where restriction enzyme recognition sites are found in the genome. Additionally, using in vivo library construction requires the library to be cloned into vectors and transformed into the preferred host E. coli. This results in a cloning bias which typically under-represents AT-rich regions of the genome (Mead et al.). In a preferred method, the production of a genomic library would not be dependent on the use of vectors and E. coli, thereby minimizing cloning biases. For example, performing emulsion ligations in combination with Emulsion PCR avoids the necessity of E. coli and permits DNA amplification on a solid support for future sequencing.

A critical question regarding the WGS approach is whether it is possible to generate enough long range scaffolding information to avoid misassemblies of genomic regions involving complex repeats, significant levels of allelic polymorphism, or recent segmental duplications. One aim is to provide a reliable sequence-derived genome map that can support the accurate selection of clones to finish any desired region of the genome. As pointed out by Jaffe et al., (supra), the C57BL6/J mouse genome has certain characteristics that may have expedited the whole genome assembly process. These include the inbred status and the apparently low number of recent segmental duplications compared to the human genome. In addition, a significant number of large insert reads were generated (about 4-fold clone coverage from 10 kb inserts, 9-fold from 40 kb inserts, and 14 fold from 200 kb inserts), although this was a strategic decision that could be applied to any genome. As stated above, the recent improvements in the ability to produce paired end sequences (paired tags) from large insert clones make it possible to significantly increase the number of such sequences compared to that used in the mouse project. A more detailed discussion of issues relating to segmental duplications and sequence polymorphism is presented below.

Clearly, independent mapping data (genetic or RH markers, or BAC overlap data, for example) is helpful for placing supercontigs in relation to each other, especially where BAC end data are missing or ambiguous. However, it is possible to generate such information by other means (see below), or to collect the necessary data to disambiguate such regions through targeted post-assembly mapping efforts (for example, using sequence data from unmapped supercontigs to identify overlapping clones directly or to augment other existing mapping resources). The method provided herein increases the number of Fosmid ends and other long range links such that they occur at a spacing of at least one every 500 bp in the assembly, more than four times the density used in the mouse project, and four times the number required to achieve statistical closure of supercontigs.

Mathematical modeling studies (Ru-Fang Yeh, 1999) indicate that genome closure, as expressed in terms of supercontig length, can be significantly accelerated by using a high level of clone coverage and a broad range of insert sizes in large whole genome shotgun projects. This is illustrated in FIG. 1 (computed from the Yeh model), in which the sigmoidal curves indicate the theoretical length of supercontigs that would be produced using our proposed mix of insert sizes (green curve) versus a single insert size (blue curve), for a non-repetitive 3 Gb genome and a 100% paired end rate.

Supercontig closure can be significantly accelerated by using high clone coverage with a mix of insert sizes.

As shown in FIG. 1, there is a significant increase in the expected contig length (from .about.98 kb to .about.567 kb) and decrease in contig number (from .about.30,000 to .about.5,300) as the sequence coverage goes up from about 7 to about 9 fold coverage (approximately equivalent to an increase in Phred Q20 coverage from about 6 to about 8 fold).

Experiments can determine the effect of insert size and modification of distance to improve the assembly. By focusing on accurate sizing of libraries from which reads are derived, the assembly based on more careful sizing of inserts is refined. For the special case of comparative sequencing applications within a species it is possible to define the distance constraints very precisely based on comparison of the paired end data to a reference sequence. All WGS reads can be pre-processed this way and entered into the assembly program.

Given the high level of shotgun coverage and the large amount of long range linking information that is obtained, genomic assemblies are generated with an average contig length of approximately 125 kb, and with supercontigs spanning a large proportion of the euchromatic chromosome arms. Gap in the large insert scaffold can be bridged through the generation and mapping of paired end GST sequences. Thus, completion of the project having very few clone gaps remaining will be achieved.

Segmental Duplications

Figure 2:
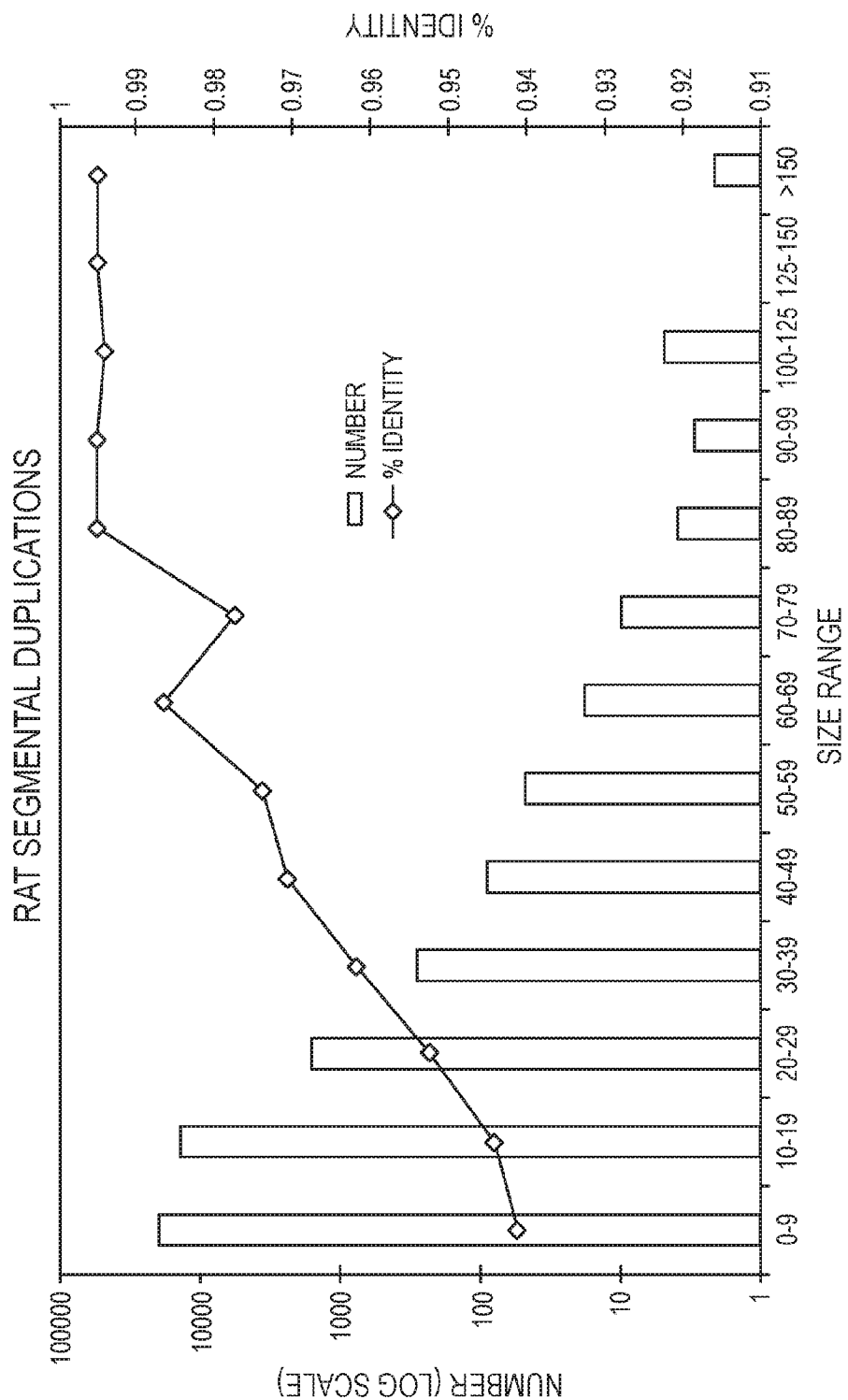
FIG. 2 is a graph depicting the number of segmental duplications identified in the rat genome versus the percent identity of the cognate pairs.

FIG. 2 graphs the information on the numbers of segmental duplications identified in the rat genome by Evan Eichler and colleagues versus the % identity of the cognate pairs (referred to here as duplicons). The number of duplications in the rat genome is similar to that in the human genome, about 3.7% vs about 4%, respectively. It is clear from the graph that there is a trend towards stronger similarity as the size of the duplicated region goes up. This phenomenon has been described previously, and presumably reflects degradation of segmental duplications over evolutionary timescales. Notably, more than 99.9% of the duplications are less than 70 kb in size, and these are generally less than 98% identical.

For duplications up to 70 kb in size, the large number of Fosmid sequence links generated in this assembly method (occurring every 500 bp or so; less than the average read length), will allow the Arachne software to connect nearly all of the sequence reads falling within the duplicated region to the unique sequences flanking it on either side (the Fosmid links to either side will still meet at the center). This, in turn, will allow clear segregation of the four chromosomal haplotypes within each pair of duplicons, considering especially the high expected accuracy of the component sequences (.about.4 fold Q20 coverage).

Larger duplications that collapsed in the assembly can be detected as extended regions with high coverage (.about.16.times.Q20), and are readily deconvoluted using the Fosmid and BAC-end information to link out to the unique sequences on each side. To correctly segregate and precisely map the two nearly identical sequences for a particular duplication of special interest, the representative BACs from each duplicon can be used to generate finished sequences.

Polymorphism

Sequences with polymorphism rates that fall significantly below the mismatch threshold settings of the assembly software (as implied above; typically about 1% mismatch for bases of Phred 20 quality and about 0.2% mismatch for bases of Phred 30 quality) will be well tolerated and correctly assembled by the software, in most cases. In the resulting assembly, these regions will be characterized by high-quality discrepancies in contigs where the assembly is otherwise strongly supported by mate pair information, allowing SNPs to be detected and characterized.

Figure 3:
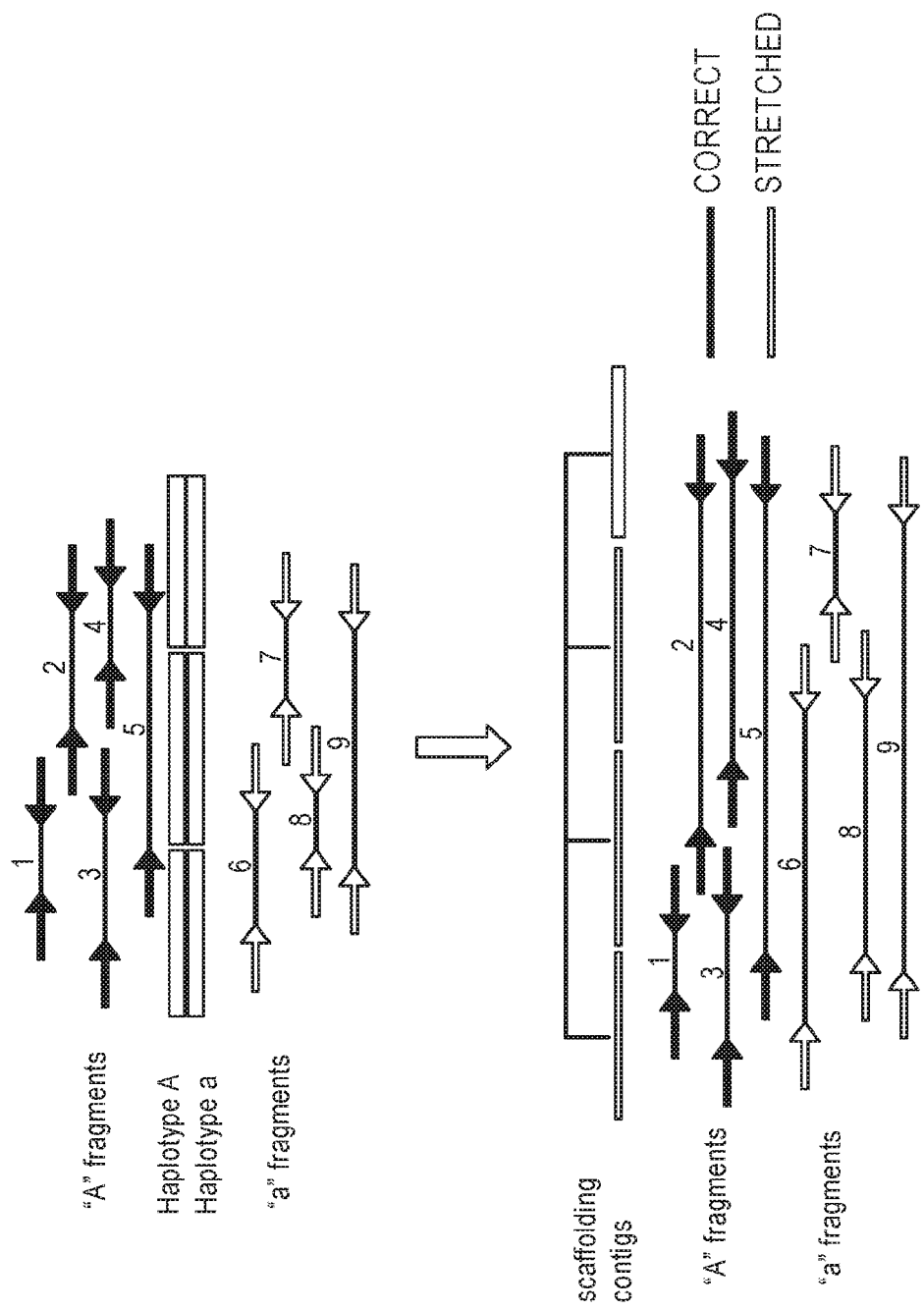
FIG. 3 is a schematic of sequence assembly (derived from Holt et al., Science 298:129-149 (2002)).

In the case of *Anopheles*, the Celera assembler was tuned to accept a higher mismatch frequency than usual to allow most regions with a high-density of SNPs to be assembled correctly (Holt, Subramanian et al. 2002). However, some regions remained where both haplotypes were assembled into separate contigs in the same supercontig causing "pseudo tandem duplication", or where one haplotype was left out of the supercontig as an entirely separate element (see FIG. 3). An understanding of the origin of these effects and their consequences in terms of mate pair conflicts between the associated contigs, however, allows detection and correction of such sequences. For example, a contig that represents a correctly assembled region with low heterozygosity would have mate pair bridges to two separate contigs representing the two different haplotypes of an adjoining region with high heterozygosity. These mate pair conflicts will force the assembler to either shift one of the polymorphic contigs out of position or to exclude it from the supercontig. Algorithmic improvements can be made to the assembly software to deal with such situations automatically. Other problems due to genomic inversions, or large palindromic sequences, can be detected by a different pattern of characteristic mate pair conflicts.

Regular assemblies of the reads will help monitor the quality of libraries on an ongoing basis. Assemblies using Arachne 2.0.1 can be monitored for number and N50 length of contigs, number and N50 length of supercontigs, average fold coverage, for the occurrence of contigs with local coverage in a sliding window that deviates significantly from the expected levels, and for mate pair conflicts as described above. If there are previously sequenced clones from the genome, comparisons to these regions can be conducted using Arachne to evaluate the assembly quality. Arachne's output assists in detecting deviations of observed K-mer frequencies versus expected, for example, which can be monitored.

New Sequenced Based Mapping Tools

It will be useful to develop sequence-based mapping tools that can compliment the WGS and BAC end sequencing data without adding significant incremental cost or operational overhead.

A high density of BAC- and Fosmid-end sequence pairs can obviate the need for independent mapping data in most regions of the genome by providing a highly redundant network of long-range clone links. However, it is possible that certain regions that are incompatible with these cloning systems would not be represented. Wherever such sequences occur in the genome, a persistent break in the large insert scaffold will be encountered. A linking strategy to jump over such sequences, such as that applied by Celera to produce "virtual 50 kb clones" (Venter, Adams et al. 2001) can be used to overcome these instances. However, by replacing the standard restriction based jumping library strategy with a novel long SAGE-like approach (Velculescu, Zhang et al. 1995), large numbers of long range links (from about 20 to about 100 kb) can be created using short sequence tags (from about 20 to about 25 bases) with approximately 20 times the efficiency of standard paired end sequencing. By using such a strategy, a genomic tag spacing of 500 bp can be generated with only about 300,000 sequencing reads. Unlike BAC- or Fosmid-end sequencing, the tags can be cloned in high copy number vectors that are compatible with our current high copy prepping methods. In addition, short genomic sequence stretches, punctuated by linker sequences, may allow efficient generation of tag pairs for AT-rich sequences that are often difficult to clone in large insert E. coli based vector systems. Thus, the method provides long range linking information where it is otherwise very difficult to generate.

Figure 4:
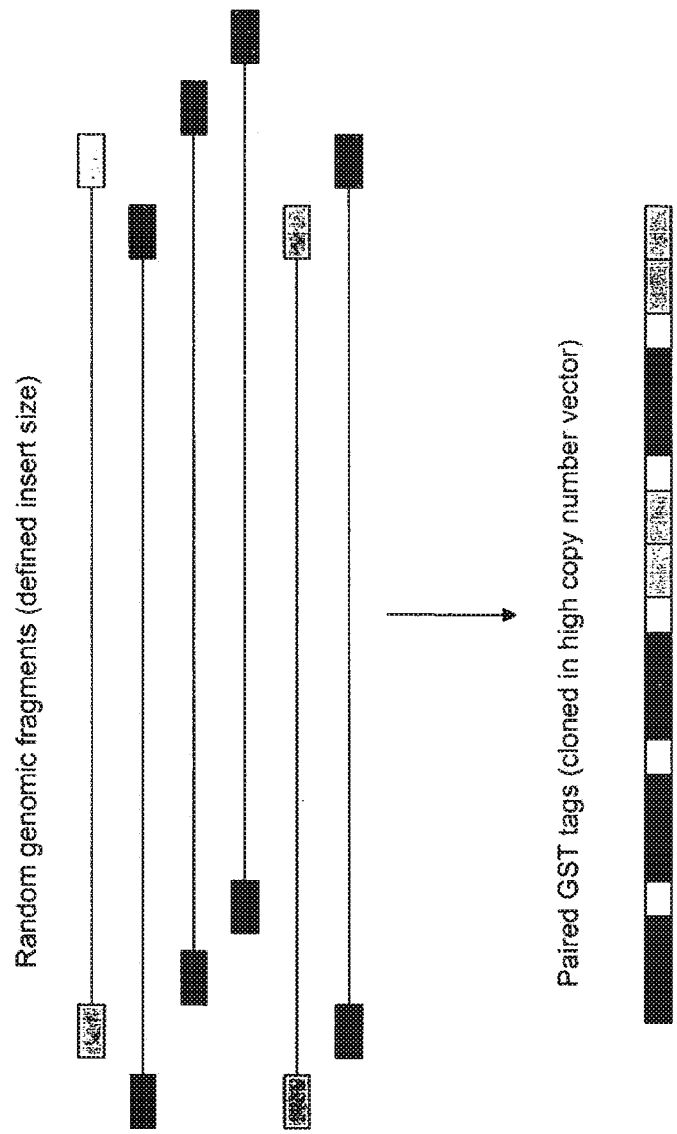
FIG. 4 is a schematic of paired tags in a concatemer.
Figure 6A:
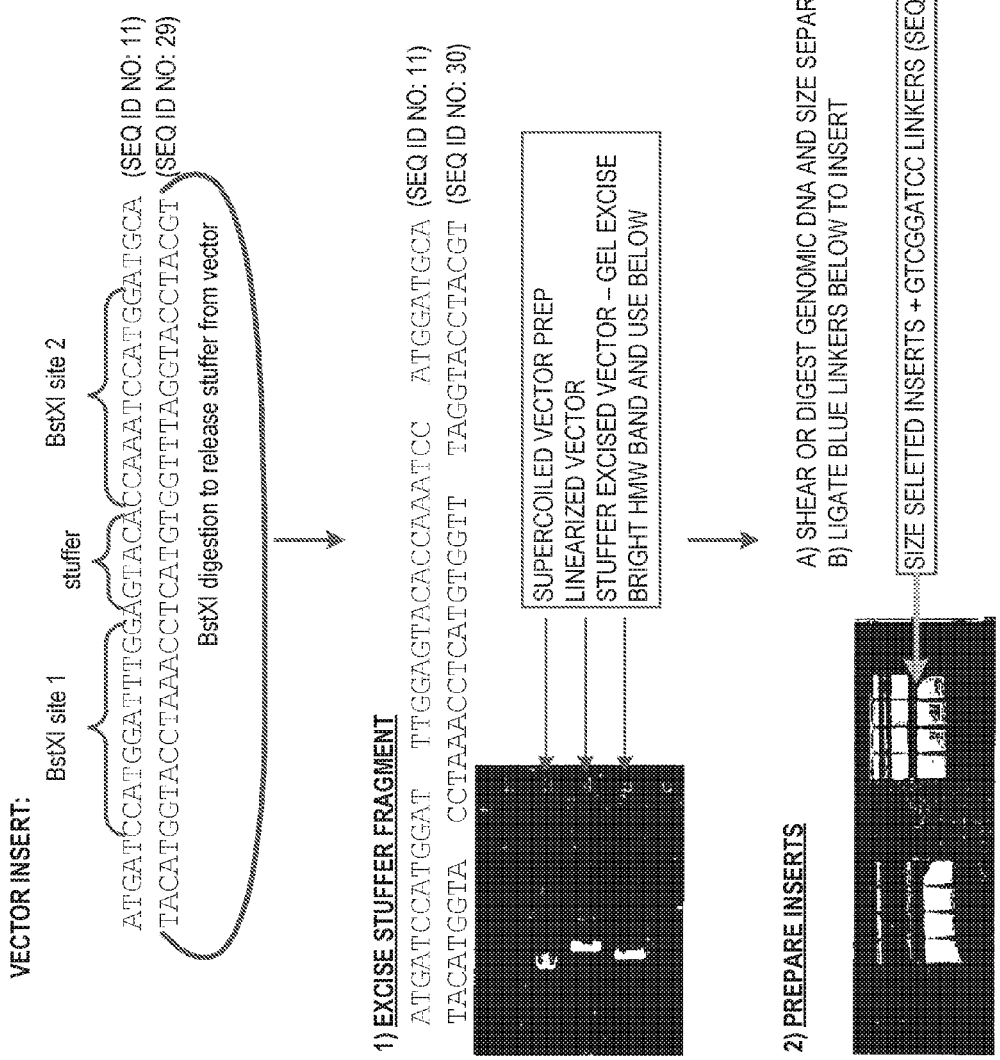
Figure 6B:
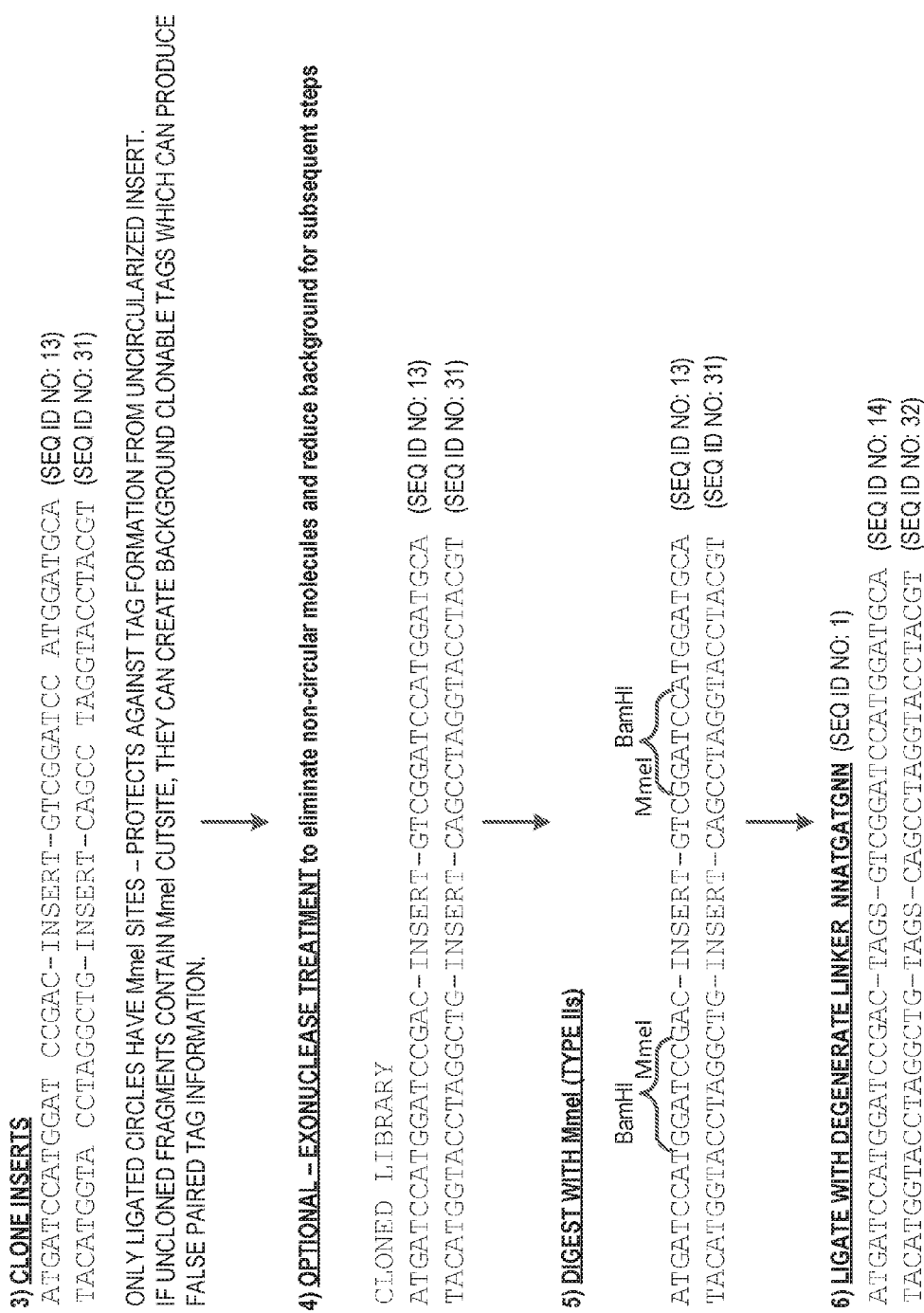
Figure 6C:
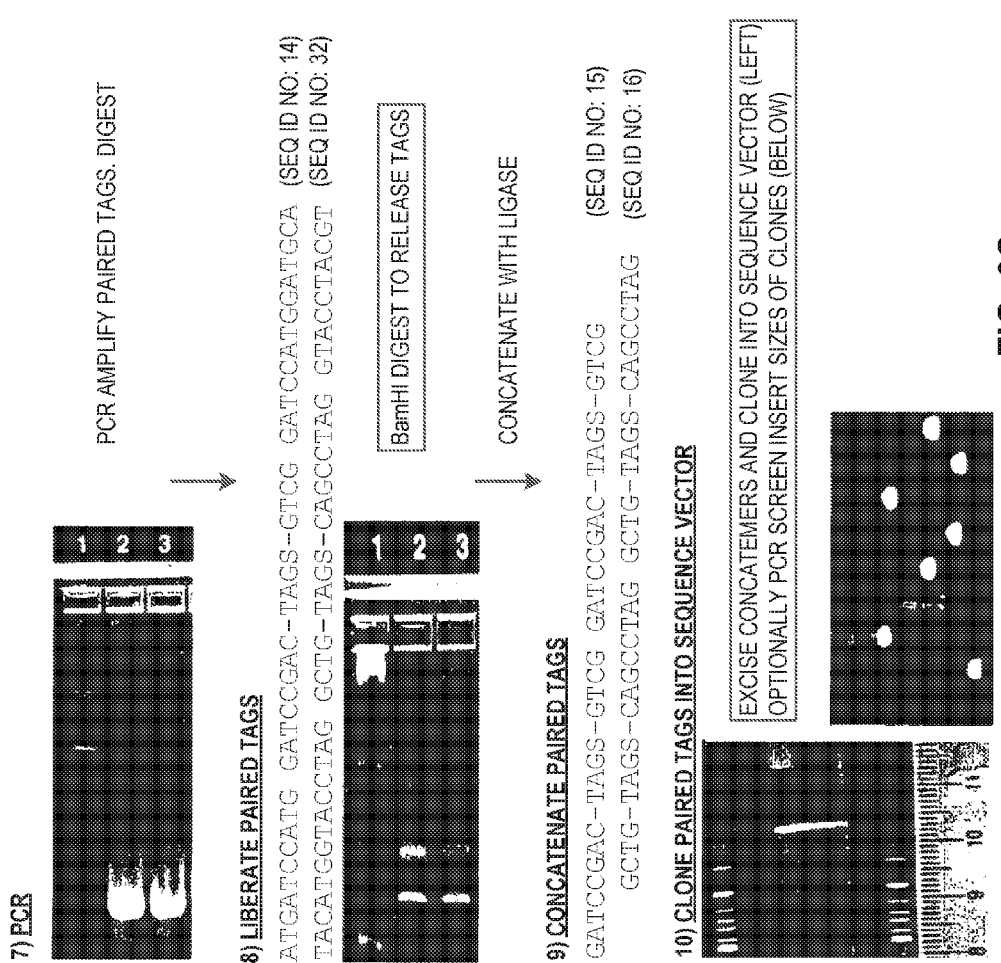
Figure 7:
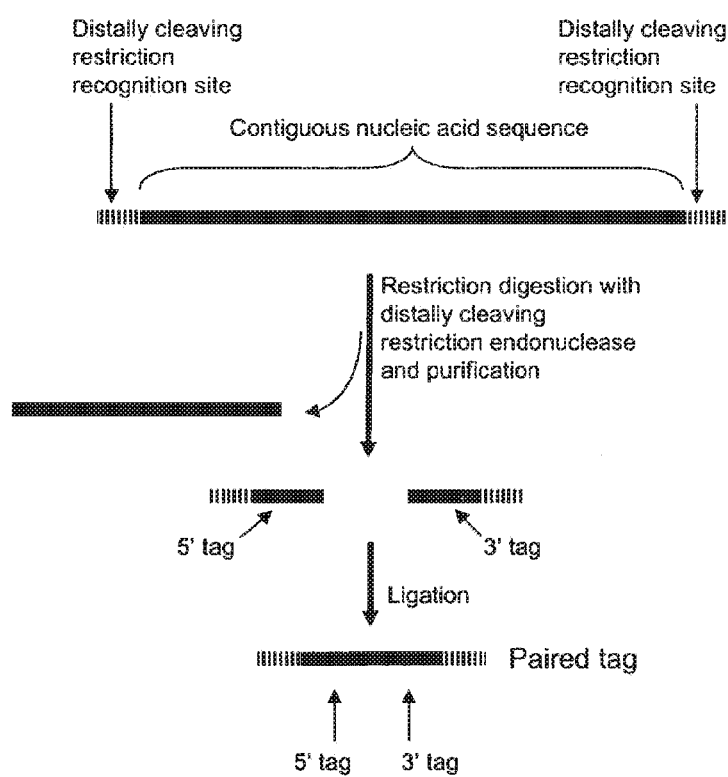
FIG. 7 is a schematic of one embodiment of paired tag formation.
Figure 8:
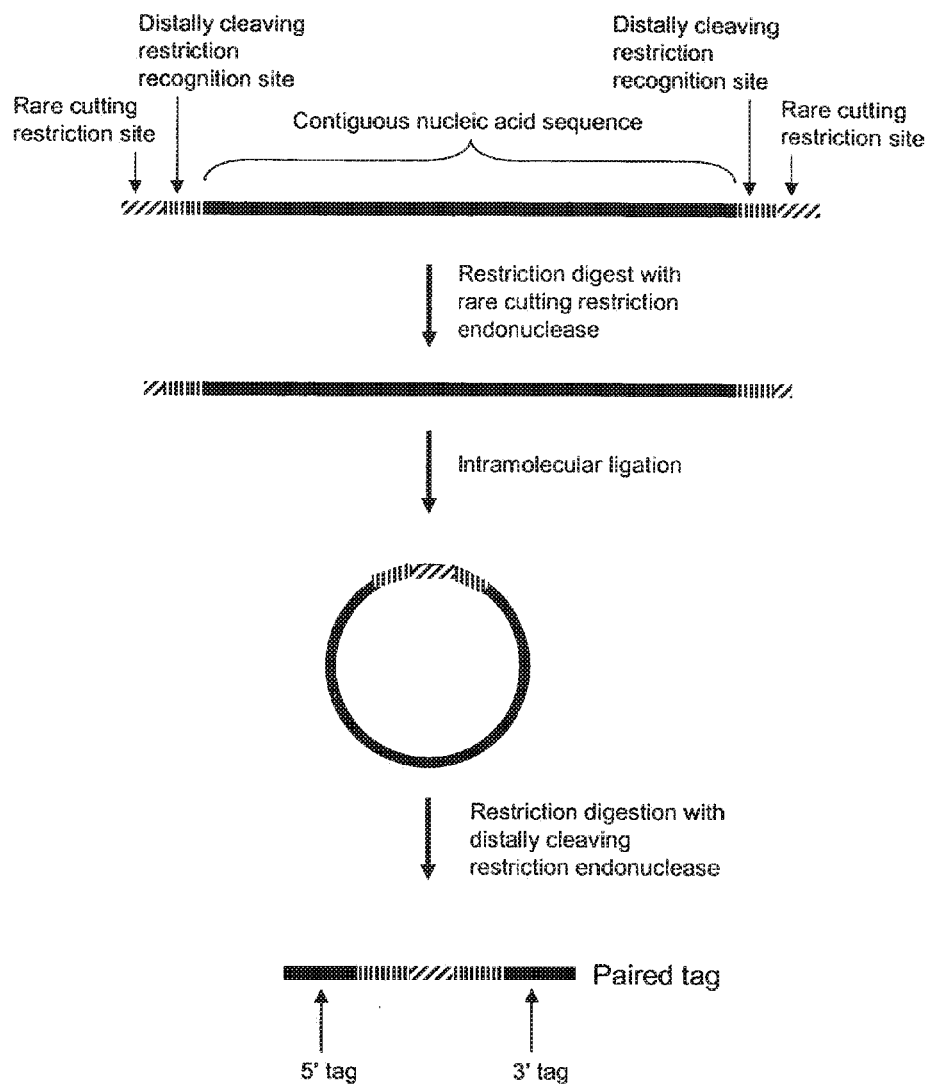
FIG. 8 is a schematic of one embodiment of paired tag formation.

This method efficiently produces paired tag pairs from randomly sheared or restriction digested fragment ends with any desired length up to about 100 kb, ensuring that only contiguous paired end tags are generated (see, for example, FIG. 4). This method is also referred to herein as Paired Genomic Sequence Tagging, or Paired GST. Paired GST libraries are distinctly different from conventional Digital karyotyping ("DK") libraries in that the paired tags are generated from the ends of individual genomic fragments.

In one method, several different restriction enzymes with hexanucleotide recognition sites that generate 4 base overhangs are used (for example, to avoid sequence bias) to partially digest the target DNA, creating a collection of fragments averaging 40 kb in size. The genomic fragments are treated with a single-strand specific endo- or exonuclease to remove the single stranded overhangs, destroying the restriction sites and leaving one base of the original hexanucleotide recognition site at each end of the fragments. This method generates sequence tags of approximately 25 base if a MmeI site is juxtaposed to the ends of the fragments because the reach of MmeI is 20 bases and 5 bases can be inferred from the destroyed restriction sites. The use of restriction enzymes can be avoided (e.g., the starting DNA can be fragmented by shearing) at the cost of 5 bases in the tag length. The method utilizes in vitro paired tag generation via intramolecular ligation in dilute solution and does not necessarily require any passage of large fragments through E. coli, thereby avoiding any cloning bias. The resulting tag pairs will bridge any persistent gaps in the high coverage plasmid and Fosmid/BAC clone scaffold.

Although tags of about 25 bases will generally be unique in a 3 Gb genome (frequency of 1 in 10.sup.15), tags with one or both ends falling in a repeated sequence may not be used to reliably force a join between two contigs or supercontigs. However, a genomic spacing of approximately 50 kb between tag pair elements (insert length) and an average spacing of approximately 500 bases between tags in the genome would result in an average of approximately 50 redundant links across any given point in the genome. Even if half of these tag pairs must be excluded for assembly purposes due to repeats, the remaining linking information across any given point would equate to approximately 1,250 bases of unique sequence information (approximately 25 paired tags of approximately 50 bases each), and would be mutually confirming, resulting in an astronomically small probability of joining error. Tag pairs with only one repeated end can be used later to confirm joins that were made during assembly using the unique information.

Example 2

Paired Genome Sequence Tag Method

Typically, a collection of genomic DNA fragments is produced by fragmentation using one or more restriction endonucleases, or by shearing, with subsequent repair of the ends to produce blunt-ended fragments. Fragments of a specific size range are purified by gel electrophoresis, followed by extraction from a gel slice by electroelution, extraction with chaotropic salts and glass beads, or enzymatic dissolution of the gel followed by phenol extraction and ethanol precipitation. The fragments are ligated to an adapter containing a type IIs restriction enzyme site juxtaposed to a blunt end and the resulting circularized products are subsequently digested with the enzyme to create short tags specific to the ends of the DNA fragment. These tags, which remain connected to each other through the process via the adapter are ligated to form concatemers of paired tags. The concatemers are sequenced and the paired tags extracted from the sequence. The paired information can be used to improve shotgun genome assemblies or detect regions of a genome that have been rearranged/translocated, amplified and/or deleted.

In one method, adapters containing a TypeIIs site followed by a rare-cutting restriction site are ligated on to the DNA in a manner that brings the TypeIIs site immediately next to the end of the prepared DNA. The adapters are created in such a way as to stop long concatemers of adapters from forming during the ligation process. Excess unligated linkers are removed using gel purification, solid phase reversible immobilization (SPRI), filtration, or selective precipitation. The adapted DNA is digested with the rare-cutting restriction enzyme generating compatible sites at the end of each adapted DNA strand. The DNA is ligated at a molarity encouraging high intramolecular ligation rather than intermolecular ligation, or in an emulsion. This creates circles of DNA with a fragment of unknown DNA and a joined linker containing two divergent TypeIIs restriction sites. These circles are digested with the TypeIIs enzyme creating a structure of: a tag, the joined linker, another tag. These tags come from the 5' and 3' ends of the prepared DNA fragment. These tags are purified from a gel and can, optionally, be concatemerized to form DNA strands containing numerous paired tags. In an alternative method, the tags are purified and can be sequence in parallel on a large scale. The concatemerized tags can either be cloned directly, or amplified using the Polymerase Chain Reaction (PCR) amplification with Phi29 or similar polymerases prior to cloning. Tags and their paring information are decoded using DNA sequencing.

In a second method, a linker containing a portion of a TypeIIs restriction followed by a non-compatible restriction site such as BstXI site, is ligated onto either end of the prepared DNA fragments. Excess linker is removed using a purification method such as gel purification, solid phase immobilization, solid phase reversible immobilization (SPRI), filtration, or selective precipitation. The DNA fragments with linkers attached are ligated to an adapter/vector which comprises a compatible form of the BstXI or similar site, the remainder of the TypeIIs site with internal divergent primer sites at a molarity that encourages circularization of the DNA on the vector/adapter. The circles are selected on a gel and digested with the TypeIIs restriction site creating linear fragments with structure: a tag, the adapter/vector, followed by another tag. These tags come from the 5' and 3' ends of the prepared DNA fragment and are blunted using appropriate enzymes prior to the subsequent ligation. The structure is ligated at a low molarity to encourage high intramolecular ligation rather than intermolecular ligation, or alternatively, in an emulsion under conditions that favor ligation of a single adapter/vector to a single prepared genomic fragment. The circles that are formed contain primer sites outside of the ligated tag pair. These primer sites are used to amplify the paired tags plus flanking sites. The amplification product is digested with the rare cut site and the tag pair purified, or the flanking sites removed using streptavidin purification if the primers were labeled with biotin. The purified tag pairs are concatemerized and cloned. Tag pair information is obtained by sequencing of the concatemers.

Example 3

Paired Tag Two-Hybrid

This method provides a linked pair of bait and prey molecules that derive from cells that screen positive for an interaction. The bait-prey pairs can be sequenced individually, for example, from plasmids, PCR or rolling circle amplification (RCA) products, or from short sequence paired tags. The paired tags can be catenated into longer molecules and sequenced using conventional unidirectional or paired end sequencing methods to generate approximately a 6-10 tag pair sequences from each sequencing read. The linking of bait and prey tags allows thousands of baits to be screened against thousands of preys (e.g., complete libraries of both) simultaneously in a single transformation and screening experiment. The catenation of tag pairs allows approximately 10 or more pairs to be characterized for the cost of one hi-copy plasmid sequencing read (depending on the read length). By using a paired end sequencing approach, approximately 12-20 tag pairs can be generated from each plasmid template isolated.

The principle of the method illustrated below for the bacterial two-hybrid system (Dove and Hochschild, Genes and Development 12:745-754, 1998) in FIG. 5. Clone libraries containing the bait and prey ORFs are typically generated in the pBT and pTRG plasmids according to established methods (for example, the ORFs can be prescreened by sequencing to select a genomic subset representing only the particular ORFs, sub-ORFs or domains of interest). The pBT and pTRG plasmids can be modified to contain a loxP or other phage attachment site at the cloning sites where ORFs are inserted. The cloning site modification may also contain, for example, a type-IIs restriction endonuclease cleavage site (such as MmeI) in such an orientation that restriction digestion will result in the generation of a short tag sequence adjacent to the loxP or other phage attachment site. Another modification includes a rare-cutting restriction endonuclease site to allow excision of the loxP site from the recombined product (described below). Cells containing individual bait plasmids are transformed with prey plasmids, or alternatively the prey molecules are introduced into cells by conjugation or by phage infection. The reciprocal experiment can also be performed (for example, transforming cells containing prey plasmids with a bait library). The cells into which the constructs are transferred can additionally contain an inducible Cre recombinase or other phage integrase gene in addition to the appropriate genetic components for the two-hybrid screening. The presence of interacting bait and prey pairs are detected, for example, by selection on agar plates containing ampicillin or carbenicillin using techniques that are standard in the art. Expression of the recombinase is induced in the selected cells to allow recombination between the two plasmids. If two different mutant loxP sites are used (e.g., lox71 and lox66) on the bait and prey constructs, respectively, then a unidirectional recombination event can be induced upon Cre expression (see Albert, et al., Plant J. 7:649-59, 1995, and Zhang and Lutz, Nucleic Acids Research 30:e90, 2002). This will increase the efficiency of generation of the recombined product, pJOIN, and will ensure that the bait-prey pairs do not undergo any further recombination after initial formation (because the lox site between them will be a double mutant). While this is advantageous, it is not absolutely required for the successful practice of the method.

After recombination, the pJOIN plasmid can be isolated by standard methods, or the bait-prey pair can be amplified, for example, by PCR using primers flanking the 3' ends of the bait and prey genes. The bait and prey ORFs can be identified, for example, by complete sequencing, or by primer-directed sequencing outward from the loxP site (or form another sequence introduced into the starting plasmids flanking the loxP sites, e.g., an M13 sequencing primer binding site).

Alternatively, plasmid DNA can be prepared from a large pool of selected colonies and digested with MmeI (or another distally-cleaving restriction endonuclease, such as a type-Ius enzyme) to release approximately 85 bp fragments containing the loxp site flanked by bait and prey tags. Alternatively, the pooled plasmid molecules can be cut at a pair of rare-cutting endonuclease sites (e.g., AsiSI) flanking the mutant loxP site between the bait and prey ORFs and the plasmids can be recircularized to eliminate that loxP site prior to MmeI digestion. This will remove the approximately 34 bp lox site, resulting in approximately 56 bp fragments after MmeI digestion, which can be purified, for example, by gel electrophoresis. A linker with appropriate overhanging ends (e.g., two base 3' overhangs of random sequence to match the MmeI ends) is ligated to the purified fragments (this preserves the full tag length of 20 bp). Digestion of the ligated linkers at a rare-cutting restriction endonuclease recognition site contained within them (e.g., AscI) will result in compatible termini on all of the fragments allowing them to be ligated together (for example, after a suitable purification step to remove excess linkers and linker fragments) to form a concatemer. After catenation of the fragments, the DNA can be fragmented, for example, sheared or subjected to shearing, or to partial digestion with AscI to generate fragments of approximately 1.5-2 kb in size. These fragments are typically cloned into high copy number vectors, such as pSMART or pUC for sequencing. Sequencing of the tag pairs is accomplished by standard methods.

The method herein described is illustrated in conjunction with the bacterial two-hybrid system. However, it can also be used in conjunction with yeast two-hybrid screening using the appropriate vectors. The Cre/loxP recombination system (or other site-specific recombination system can be used as will be understood by one of skill in the art) can be used with inducible expression of the heterologous Cre recombinase in the appropriate yeast host. In one method, to improve the recovery of large amounts of plasmid from yeast cells, the plasmids can be amplified by passage through E. coli, or by rolling circle amplification. Alternatively, the region including the bait-prey tags can be amplified by PCR using primers that hybridize outside of the cloned ORF sequences (e.g., in the fused genes, promoter regions or multiple cloning sites).

The tagging method generates paired tags from bait and prey molecules that originally existed on different plasmids that were introduced into the target cells at different times. Paired tag formation can also be accomplished by cloning bait and prey molecules into a modified two-hybrid vector in which the two ORFs are appropriately arranged in a single vector with relation to the distally-cleaving restriction enzyme, such as MmeI or other type-Ius restriction sites, so that the intervening regions are excised enzymatically. This permits the bait-prey paired tags to be generated without using recombination.

Example 4

Method for Generating Paired Genome Sequence Tags

Detecting genome amplifications, deletions and translocations has been shown to pinpoint genes of interest in various disease states including cancer and mental retardation. Paired-end sequences have been shown capable of detecting these regions of change in previously sequenced genomes in addition to improving the assembly of novel shotgun sequences. In this method of "Digital Karyotyping," translocations, amplifications and deletions can be detected in a previously sequenced genome using "Paired Genome Sequence Tags" (PGSTs). These tags can be produced, for example, using a Type IIs restriction enzyme similar to those generated in Digital Karyotyping and SAGE. The tags in PGST, however, are generated from both ends of DNA fragments and remain associated through concatemerization and sequencing steps. This produces paired tags a defined distance from each other in the genome. Greater than about 15 tag pairs can be obtained from a single sequence. The tags can be used to detect regions of amplification and deletion in previously sequenced genomes. The additional information obtained through pairing also allows the detection of translocations. This method also applies to generating paired tag information for scaffolding genome shotgun assemblies. In this method, paired-end sequence information is produced in an extremely efficient manner that is free from cloning biases and is a valuable method in genome shotgun sequencing.
Creation of a PGST Linker An oligonucleotide and its complement containing two BstXI restriction recognition sites separated by an RsaI recognition site were synthesized. The oligonucleotide has the sequence: TABLE-US-00001 AGCTTCCATGGATTTG-GAGTACACCAAATCCATGGT (SEQ ID NO:2)

In this example, the BstXI sites were designed to have the same recognition site sequence and which were not complementary to each other so that cleavage with BstXI would not generate a 5' and 3' end which could self-ligate. Furthermore, the oligonucleotide and its complement were designed to contain one nucleotide base of a Type Ius restriction enzyme recognition site, in this example, MmeI, as well as a portion of an additional restriction enzyme recognition site, in this case BamHI, which was used later for concatenation of the paired genome sequence tags (also referred to herein as paired tags).

The oligonucleotide and its complement were annealed to produce a double stranded oligonucleotide which was inserted into a vector, such as pUC18 or pUC 19, between an M13R primer site/SP6 promoter and an T7 promoter/M13F primer site. The vector was digested with the restriction enzyme PvuII, which has two recognition sites that flank the M13R primer site/SP6 promoter and T7 promoter/M13F primer sites, to release a fragment having the order: [0130]— PvuII-M13R/Sp6-BstXI-RsaI-BstXI-T7/M13F-PvuII—

This fragment was purified using agarose gel electrophoresis and the fragment circularized on itself by intramolecular ligation. The circularized fragment was then digested with the restriction enzyme RsaI to create a linear linker having the order: [0131]—BstXI-Sp6/M13R-PvuII-M13F/T7-BstXI—

This linker was inserted by blunt end cloning into an E. coli-based vector (such as the pAGEN vector) which did not contain any of the primer sites contained in the above linker. The linker construct was transformed into an E. coli strain for maintenance, propagation and amplification of the linker, using standard protocols as will be understood by one of skill in the art. Preparation of the Linker for Use in the System A plasmid DNA preparation from the strain containing the linker construct was digested with the restriction enzyme BstXI, thereby releasing the linker and creating identical, non-complementary, 3' overhangs on either side of the linker. Preparation of DNA of Interest for Ligation to the Linker The nucleic acid sequence or DNA of interest, in this example, the E. coli genome, was sheared using a mechanical method (either nebulization, hydrodynamic shearing through a small orifice, or sonication). The randomly sheared DNA was end repaired using nucleotides (dNTPs) with T4 DNA Polymerase which has 5'-3' polymerase activity as well as 3'-5' exonuclease activity which fills in 3' overhangs and cuts back 5' overhangs, respectively. In this example, the T4 DNA Polymerase with the free nucleotides (dNTPs) filled in the BstXI 3' overhangs. This end-repaired randomly sheared DNA was separated by size using agarose gel electrophoresis. Fragments of the desired size, in this example, 2-3 kilobases (kb), were cut from the gel and purified using standard gel purification columns. The purified, size selected DNA fragments were ligated to specific DNA adaptors in vast molar excess to ensure that the DNA fragments neither circularized nor ligated to the end of another DNA fragment. The DNA adaptors were complementary to the digested BstXI sites of the linker prepared earlier. The adapter has the following top and bottom strands: TABLE-US-00002 (top strand) 5' CCGACA 3' (SEQ ID NO:3) ||||| (bottom strand) 3' CCTAG-GCTGT 5' (SEQ ID NO:4)

The blunt end of the adapter is ligated to the fragment of interest while the overhang is complementary to the overhang left after digestion of the DNA linker with BstXI. Excess adapter was removed by agarose gel purification of the 2-3 kb adapted DNA fragments. Ligation of the Adapted DNA Fragments to the Linker The adapted DNA fragments were ligated to the DNA linker (prepared above) using the following formulas to determine the molar ratio of adapted DNA fragments to DNA linker to ensure the greatest number of circular fragments comprising one adapted DNA fragment and one DNA linker generated by intramolecular interactions during ligation (Current Protocols in Human Genetics (1994) "Construction of Chromosome Jumping and Linking Libraries in *E. coli*" by Drumm, Eds. Nicholas C. Dracoploi et al.): J=K/S.sup.1/2 N=J/(I+J) Where, K is the constant 63.4 micrograms per milliliter (.mu.g/mL), S is the size of the DNA fragment ligated to the linker in units of Kilobases (kb), N is the fraction of intramolecular interactions (e.g., 0.95=95% intramolecular interactions), and I is the concentration of DNA in micrograms per milliliter (.mu.g/mL) to obtain the desired fraction of intramolecular interactions.

Ligation of the DNA linker to the adapted DNA fragments creates a full MmeI site and a full BamHI site on either end of the adapted DNA fragment due to the design of the linker and the adapter. The circular DNA was purified from the other products of the ligation reaction by size separation on an agarose gel. The circular DNA was digested with MmeI releasing all of the DNA fragment except a 20/18 bp tag on either side of the DNA linker (i.e., a paired tag on the linker). The 20 bp is the number of nucleotides remaining from the restriction endonuclease recognition site in the 5 prime to 3 prime direction of the DNA upon digestion with the restriction enzyme. Likewise, the 18 bp refers to the number of nucleotides remaining from the enzyme recognition site on the 3 prime to 5 prime strand upon digestion with the restriction enzyme.

The DNA linker plus the paired tags from the DNA fragment of interest were separated from other digestion fragments by size selection using agarose gel electrophoresis using standard protocols. The DNA linker plus the paired tags were blunt ended to remove the 3' overhang using T4 DNA Polymerase to leave 18 bp of each of tag in the paired tag. The DNA linker plus blunt-ended paired tag was subsequently purified using phenol/chloroform extraction. Each DNA linker plus the blunt-ended paired tags were self-ligated to form a circular DNA using the above formula to ensure intramolecular interactions leading to formation of single circles such that the paired tags were now adjacent to each other. This circularization also caused the primer sites (M13R/Sp6 and T7/M13F) on the DNA linker flanking the paired tags to become convergent (i.e., while the DNA linker is linear, the PCR primer sites are directed away from each other (divergent), but upon circularization, the primer sites are directed toward each other thereby allowing amplification of the intervening DNA (the paired tags).

Using the primer sites, the joined paired tags were PCR amplified using standard PCR conditions, gel purified, and digested with BamHI to release the joined paired tags flanked by cut BamHI sites. The released joined paired tags flanked by cut BamHI sites were gel purified using PolyAcrylamide Gel Electrophoresis (PAGE) followed by elution of the paired tags from the gel. The released paired tags flanked by cut BamHI sites ("sticky ends") were concatenated by ligation to each other via the BamHI sticky ends to form concatemers of approximately 600-800 base pairs. The concatemers were size-selected on an agarose gel and subsequently purified. The purified, size-selected concatemers were ligated into the BamHI site of pUC-based *E. coli* vector (e.g., pUC18), and the construct transformed into *E. coli* using standard electroporation procedures. Colonies containing the concatemer vectors were selected, grown, and plasmid DNA was prepared from them for sequencing using standard protocols.

The plasmid DNA was sequenced using cycle sequencing kits from Applied Biosystems and separated on an Applied Biosystems 3730XL DNA analyzer. The readout sequences were then separated using a PERL script which split the sequences based on the flanking BamHI sites in order to identify the sequences of the paired tags. Individual tags in the paired tag were determined by using the substring of sequence on each side of a paired tag that contained the BamHI recognition site plus 18 nucleotides. The BamHI restriction site was subtracted from the tag sequence and the tag sequence matched to a hash of all 18mers in the *E. coli* genome. As will be understood by a person of skill in the art, a "hash" is a standard computing term meaning an array of arrays, or a list of lists in which the first list contains each 18mer in the genome as separate entries and each 18mer entry has associated with it a list of information, which in this case has information regarding where the 18 mer is located in the genome and which strand it was located. The hash of all 18 mers in the *E. coli* genome contained information on the location and orientation of each 18 mer present in the genome. Each tag was therefore assigned a location and orientation in the genome. Some tags matched repetitive 18 mers in the genome, i.e., a stretch of 18 nucleotides was found in multiple locations in the genome. In these cases, half of the repetitive 18 mer tags sequenced were unambiguously placed based on the location and orientation of their paired tag mate. Initial analysis of 45 unique paired tags obtained from the sequencing revealed approximately 85% of them were correctly paired, i.e., the paired tag sequences were both the expected 2-3 kb distance away from each other and on opposite strands in the genome.

Example 5

Method for Generating Paired Genome Sequence Tags

This method generates paired tags from the ends of a set of genomic DNA fragments by generating the tags by fragmentation means other than by cleavage with restriction endonucleases that cleave distally to their recognition sites. This method produces end-sequence tags in which the tag length can be arbitrarily large, thus accommodating longer sequence read lengths than the shorter sequence read lengths (e.g., 18-27 bases) typically obtained by a restriction endonuclease approach.

This method is particularly useful for generating DNA sequence information from each of the two ends of a set of DNA fragments in such a way that the pairing information is preserved. Such information is useful for de novo sequencing and DNA sequence assembly using genome assembly software such as Arachne, the Paracel Genome assembler, Jazz or the Celera Assembler. It is also useful for re-sequencing, polymorphism discovery and genotyping applications to characterize the genetic differences between genomes from different individuals, for example, between two human genomes, to characterize a genome for the presence of known mutations or polymorphisms, or to characterize associations between specific sequences or polymorphisms with particular phenotypes, predisposition to disease or with other traits of interest. An illustration of the method is presented in FIG. 9.

Some steps of this procedure are optional, or could be substituted by other specific methods. In a particular embodiment, the method comprises circularizing a first set of DNA fragments ("1" in FIG. 9), produced by random fragmentation of the DNA to be sequenced (e.g., a genomic DNA sample—this could be accomplished by mechanical shearing, or by specific- or non-specific endonuclease digestion, oxidative fragmentation by metal ions, or any other fragmentation means) using a short DNA linker that has an attached affinity tag (3 in FIG. 9) to allow subsequent binding and recovery of DNA fragments containing the affinity tag. The method shown in FIG. 9 specifies ligation of non-self-complementary end-linkers (2 in FIG. 9) having a unique 5' or 3' overhang to the starting set of fragments prior to circularization (after healing the ends on the starting set of fragments to create blunt ends using a combination of DNA polymerase(s), exonuclease(s) and/or polynucleotide kinase). This approach improves the specificity of the subsequent circularization step to ensure that the DNA fragments do not self-ligate or circularize without incorporating the affinity tag linker (3 in FIG. 9), which, in the above example comprises a set of non-self-complementary ends that are complementary to those on the end-linkers (2 in FIG. 9). After circularization, the sample is treated with Bal31, (or with a similar exonuclease, or with a mixture of an exonuclease plus a single-stranded DNA specific exo- or endonuclease, or with a commercial "plasmid-safe" DNAse product) to destroy any leftover linear molecules including any unligated affinity tag. The exonuclease is inactivated, and the remaining circles are fragmented into smaller pieces to produce a second set of DNA fragments. The pieces that contain the affinity tag are captured, purified and are then sequenced: a) directly, using a single molecule sequencing approach, b) after molecular cloning using standard methods (e.g., after ligation into a selectable vector followed by transformation and propagation of individual fragments in *E. coli* or other suitable host), or c) after amplification by PCR (with or without the addition of universal priming sites (4) by ligation of oligonucleotides at the ends). One method for amplification and sequencing, shown in the figure above, is by clonal amplification on magnetic beads containing an oligonucleotide complementary to the universal primers (4 in FIG. 9) in a water/oil emulsion (or by some other clonal amplification means) such that the amplified fragments become bound to the beads in both possible orientations. Alternate means of amplifying after applying means for attachment of different primers to the two ends of the sheared fragments could be applied to produce magnetic beads with the final amplified fragments in one orientation only.

Figure 9:
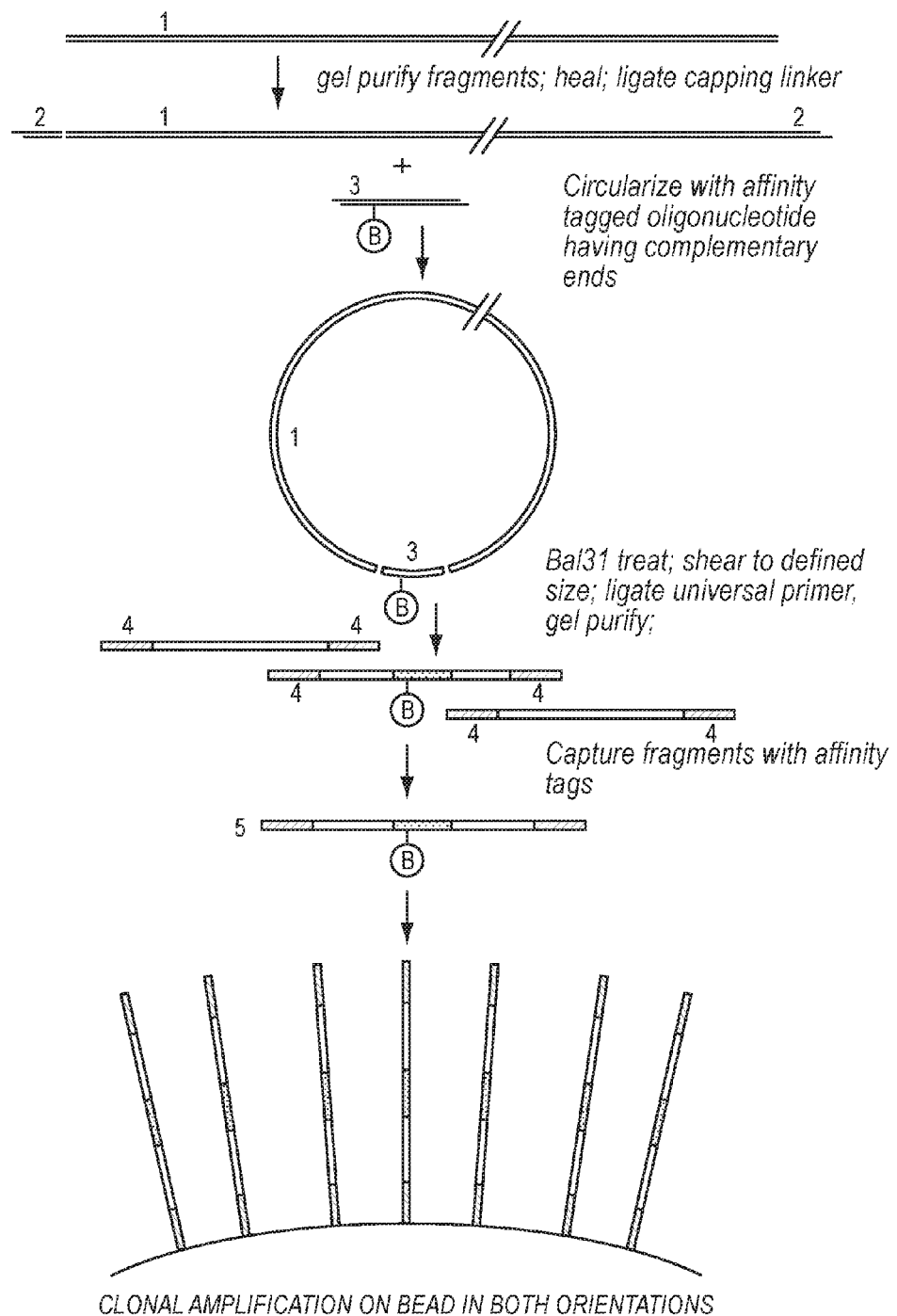
FIG. 9 is a schematic of one embodiment for generating paired genome sequence tags.

The affinity tag shown in FIG. 9 represents biotin attached to one of the nucleotides, but many other types of affinity tags could be used, such as digoxygenin or other small molecule for which specific antibodies are available. Alternatively, a target sequence for a DNA binding protein such as the *E. coli* lactose repressor could be included in the linker, or a sequence capable of being hybridized as a triple helix. In the example above, the DNA fragments would be recovered by binding to a matrix (e.g., magnetic beads) with immobilized streptavidin prior to ligation of the universal primer oligonucleotides The affinity tag oligonucleotide comprises sequences that double as sequencing primers. A different primer is used to sequence in each direction outward from the tag.

An advantage of this method over previous methods is that it can generate tags of any desired length, up to several kilobases, on average, if desired. Paired tag fragment lengths of several hundred bases would be adequate to support sequence read lengths of 25-200 bases using conventional Sanger sequencing or revolutionary sequencing by synthesis methodologies, such as Polony Technology as developed by G. Chuch and colleagues, Pyrosequencing in picotiter plates as developed by 454 corporation, or Massively Parallel Signature Sequencing as developed by Lynx Therapeutics. The precise size of the two sub-fragments flanking the affinity tag linker will be variable, and unknown, but on average it will be about half of the total fragment length). Thus for a 50 base read length and a total fragment length of 580 bases with a 30 base affinity tag, 90% of sequence reads originating from the affinity tag would be at least 50 bases long. If longer read lengths are desired, a longer paired tag fragment length can be generated.

Figure 10:
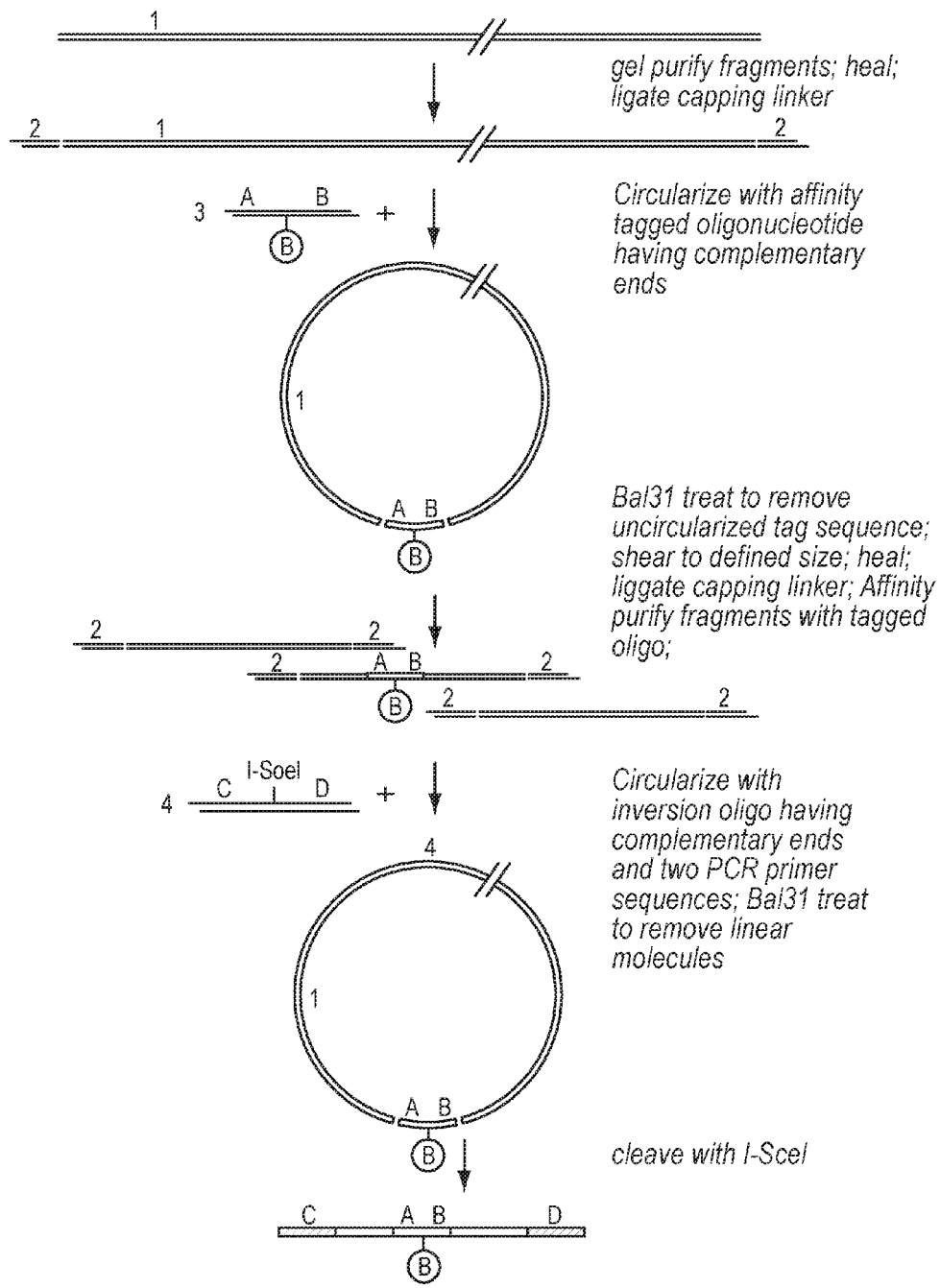
FIG. 10 is a schematic of one embodiment for generating paired genome sequence tags.

One means for attachment of two different primers to the two ends of the final fragments involves the use of a second circularization step to introduce two different sequences capable of being used as PCR primers instead of ligating a single universal primer. The advantage of this implementation is that it avoid the requirement for doing PCR on a support using a single primer by "bridge PCR"—a method that is known to result in poor efficiency of fragment amplification and which also results in both DNA strands being attached to the support, which reduces sequencing efficiency. The second circularization method is illustrated in the lower half of FIG. 10.

Figure 11:
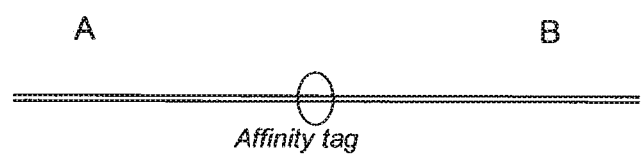
FIG. 11 is a schematic of an affinity tag with two unique primer sequences.

The first steps in this procedure are the same as before. A first set of DNA fragments (1 in FIG. 10) produced by fragmentation of genomic DNA are circularized using a short DNA linker that has an attached affinity tag (3 in FIG. 10) to allow subsequent binding and recovery of DNA fragments containing the affinity tag. As, before, the method employs initial ligation of non-self-complementary end-linkers (2 in FIG. 10) having a unique 5' or 3' overhang to the starting set of fragments prior to circularization (after healing the ends on the starting set of fragments to create blunt ends using a combination of DNA polymerase(s), exonuclease(s) and/or polynucleotide kinase). The capping step improves the specificity of the subsequent circularization step to ensure that the DNA fragments do not self-ligate or circularize without incorporating the affinity tag linker (3 in FIG. 10), which, in the above example comprises a set of non-self-complementary ends that are complementary to those on the end-linkers (2 in FIG. 10). The length of the affinity tag linker is at least 20 nucleotides, such that two unique primer sequences (A and B) can be accommodated, which will allow hybridization of primers to both DNA strands to allow priming of DNA synthesis in either direction, as seen in FIG. 11.

After circularization, the sample is treated with Bal31, (or with a similar exonuclease, or with a mixture of an exonuclease plus a single-stranded DNA specific exo- or endonuclease, or with a commercial "plasmid-safe" DNAse product) to destroy any leftover linear molecules including any unligated affinity tag. The endonuclease is inactivated and the remaining circles are fragmented into smaller pieces to produce a second set of DNA fragments. The pieces that contain the affinity tag are captured at this point, by mixing with streptavidin coated magnetic beads, for example. After healing the ends on the starting set of fragments to create blunt ends using a combination of DNA polymerase(s), exonuclease(s) and/or polynucleotide kinase), a capping linker (2 in FIG. 11) is added to the linear DNA fragments. As before, the preferred capping linker has non-self-complementary ends with a unique 5' or 3' overhang. This approach improves the specificity of the subsequent circularization step to ensure that the DNA fragments do not self-ligate or circularize without incorporating the inversion linker (4 in FIG. 11), which, in the above example comprises a set of non-self-complementary ends that are complementary to those on the end-linkers (2 in FIG. 11). The inversion linker (4 in FIG. 11) comprises two unique sequences (C and D) that can be used subsequently to prime DNA synthesis in a PCR reaction, and a rare-cutting endonuclease site between the C and D sequences. After circularization, the sample is treated with Bal31, (or with a similar exonuclease, or with a mixture of an exonuclease plus a single-stranded DNA specific exo- or endonuclease, or with a commercial "plasmid-safe" DNAse product) to destroy any leftover linear molecules including any unligated inversion tag. The nuclease is inactivated and the remaining circles are linearized using the rare-cutting Endonuclease (or other rare cleavage means), in the case illustrated the endonuclease is I-SceI. If desired, a second round of enrichment for fragments containing the affinity tag could be performed at this stage.

As before, sequencing could be done: a) directly, using a single molecule sequencing approach, b) after molecular cloning using standard Sanger methods (e.g., after ligation into a selectable vector followed by transformation and propagation of individual fragments in *E. coli* or other suitable host), c) after amplification by PCR, or d) after clonal amplification using polony technology, emulsion PCR, bridge PCR, or some other clonal amplification means. A preferred method for amplification and sequencing is by clonal amplification on magnetic beads containing an oligonucleotide complementary to one end of the molecules to be amplified (in a water/oil emulsion, for example) such that the amplified fragments become bound to the beads in only one orientation. For example, if the "C" primer is covalently attached to the beads through a chemical linker at the 5' end (or non-covalently using 5' biotin and streptavidin beads—or by some other high affinity non-covalent attachment means). Molecules amplified on beads will then become attached as shown in FIG. 12.

All molecules on any one bead will contain the same sequences, in the same orientation. The unattached strand can then be removed by denaturation. On some beads (I. in FIG. 12), the orientation of the affinity-tag linker will be such that a primer complementary to the A sequence will hybridize to attached DNA strand. On other beads (II. in FIG. 12), the orientation of the affinity-tag linker will be such that a primer complementary to the B sequence will hybridize to attached DNA strand. By performing a sequencing by synthesis procedure on a mixture of clonally amplified templates (e.g., a mixture of beads on a polony slide) sequentially with two sets of primers, sequences from both ends of the starting set of DNA fragments (1 in FIG. 12) can be acquired. To do this, sequences are first generated by priming with the D primer (each bead with clonally amplified molecules will produce a unique sequence). Next, sequences are generated by priming with a mixture of the A and B primers (each bead with clonally amplified molecules will produce a unique sequence, primed from either the A or B primer only).

The starting set of fragments (1 in FIG. 12) can be of any length up to several hundred kilobases, but preferably will be in the range of 2 to 200 kb. The second set of DNA fragments (produced after circularization with the affinity tag) can be of any length up to the size of the first set of fragments, but preferably will be in the range of 0.1 to 2 kb. The average read length that can be obtained from each end will be equal to ½ the length of the second set of fragments minus the length of the affinity tag linker.

The relevant teachings of all the references, patents and patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for preparing a plurality of nucleic acids, comprising:
   a) producing a plurality of circular nucleic acids, by intramolecularly ligating a plurality of nucleic acid fragments each having one or more first adaptors joined to the 5' and 3' ends of a linear nucleic acid fragment;
   b) fragmenting the plurality of circularized nucleic acids by shearing, thereby producing a plurality of linear paired tag fragments containing the one or more first adaptors and a paired tag having the 5' end and the 3' end of the linear nucleic acid fragment in step (a); and
   c) joining a second adapter to both ends of the plurality of linear paired tag fragments thereby producing a plurality of adaptor-joined paired tag fragments.

2. The method of claim 1, further comprising the step: amplifying the plurality of adaptor-joined paired tag fragments thereby producing amplified paired tags.

3. The method of claim 2, further comprising: sequencing the amplified paired tags.

4. The method of claim 2, wherein the plurality of adaptor-joined paired tag fragments are subjected to size fractionation prior to amplifying the plurality of adaptor-joined paired tag fragments.

5. The method hod of claim 1, further comprising the step: sequencing the plurality of adaptor-joined paired tag fragments.

6. The method of claim 1, wherein the first adaptors include a 5' overhang end, a 3' overhang end or a blunt end.

7. The method of claim 1, wherein the first adaptors include a biotin moiety.

8. A method for characterizing a nucleic acid, comprising:
   a) fragmenting a nucleic acid to produce a plurality of nucleic acid fragments, each nucleic acid fragment in the plurality having a 5' end and a 3' end;
   b) joining one or more first adapters to the 5' and 3' ends of the plurality of nucleic acid fragments, thereby producing a plurality of first modified nucleic acid fragments;
   c) intramolecularly ligating the plurality of modified nucleic acid fragments, thereby producing a plurality of circularized nucleic acids having the one or more first adapters located between the 5' end and the 3'end sequences of the nucleic acid fragment of step (a);
   d) fragmenting the plurality of circularized nucleic acids by shearing, thereby producing a plurality of linear fragments containing the one or more first adaptors and a paired tag having the 5' end and the 3' end of the linear nucleic acid fragment in step (a); and
   e) joining a second adapter to the 5' and 3' ends of the plurality of linear fragments thereby producing a plurality of second modified nucleic acid fragments.

9. The method of claim 8, further comprising: amplifying the plurality of second modified nucleic acid fragments, thereby producing amplified paired tags.

10. The method of claim 9, further comprising: sequencing the amplified paired tags.

11. The method of claim 8, further comprising: sequencing the plurality of second modified nucleic acid fragments.

12. The method of claim 8, wherein the joining in step (b) is selected from a group consisting of ligation, annealing and recombination.

13. The method of claim 12, wherein the joining in step (b) comprises homologous recombination.

14. The method of claim 8, wherein the first adaptors include a 5' overhang end, a 3' overhang end or a blunt end.

15. The method of claim 8, wherein the first adaptors include a biotin moiety.

16. The method of claim 8, wherein the shearing comprises nebulization, hydrodynamic shearing through a small orifice, or sonication.

17. The method of claim 8, wherein the joining in step (e) comprises ligation.

* * * * *

SEQUENCE LISTING

```
<160> NUMBER OF SEQ ID NOS: 33

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      Oligonucleotide linker
<220> FEATURE:
<221> NAME/KEY: modified_base
<222> LOCATION: (1)..(2)
<223> OTHER INFORMATION: a, c, t or g
<220> FEATURE:
<221> NAME/KEY: modified_base
<222> LOCATION: (9)..(10)
<223> OTHER INFORMATION: a, c, t or g

<400> SEQUENCE: 1 nnatgatgnn                                                            10

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
agcttccatg gatttggagt acaccaaatc catggt                               36

<210> SEQ ID NO 3
<211> LENGTH: 6
```

```
<212> TYPE: DNA
<213> ORGANISM: Artificial Sequence
<220> FEATURE:
<223> OTHER INFORMATION: Description of Artificial Sequence: Synthetic
      adapter-top strand oligonucleotide

<400> SEQUENCE: 3 ccgaca                                                                    6

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      adapter-bottom strand oligonucleotide

<400> SEQUENCE: 4
tgtcggatcc                                                               10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      top strand oligonucleotide ASCI linker
<220> FEATURE:
<221> NAME/KEY: modified_base
<222> LOCATION: (9)..(10)
<223> OTHER INFORMATION: a, c, t or g

<400> SEQUENCE: 5 ggcgcgccnn                                                               10

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      bottom strand oligonucleotide ASCI linker
<220> FEATURE:
<221> NAME/KEY: modified_base
<222> LOCATION: (9)..(10)
<223> OTHER INFORMATION: a, c, t or g

<400> SEQUENCE: 6 ggcgcgccnn                                                               10

<210> SEQ ID NO 7
<211> LENGTH: 68
<212> TYPE: DNA
<213> ORGANISM: Artificial Sequence
<220> FEATURE:
<223> OTHER INFORMATION: Description of Artificial Sequence: Synthetic
      pBT Lox oligonucleotide linker
<220> FEATURE:
<221> NAME/KEY: modified_base
<222> LOCATION: (49)..(68)
<223> OTHER INFORMATION: a, c, t or g

<400> SEQUENCE: 7
ataacttcgt ataatgtatg ctatacgaac ggtagcgatc gctccaacnn nnnnnnnn        60 nnnnnnnn                                                                 68

<210> SEQ ID NO 8
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      pBT Lox peptide linker

<400> SEQUENCE: 8

Ile Thr Ser Tyr Asn Val Cys Tyr Thr Asn Gly Ser Asp Arg Ser Asn
1               5                   10                  15

<210> SEQ ID NO 9
<211> LENGTH: 68
<212> TYPE: DNA
<213> ORGANISM: Artificial Sequence
<220> FEATURE:
<223> OTHER INFORMATION: Description of Artificial Sequence: Synthetic
      pTRG Lox oligonucleotide linker
<220> FEATURE:
<221> NAME/KEY: modified_base
<222> LOCATION: (49)..(68)
<223> OTHER INFORMATION: a, c, t or g

<400> SEQUENCE: 9
ataacttcgt atagcataca ttatacgaac ggtagcgatc gctccaacnn nnnnnnnnn     60 nnnnnnnn                                                             68

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      pTRG Lox peptide linker

<400> SEQUENCE: 10

Tyr Arg Ser Tyr Ser Ile His Tyr Thr Asn Gly Ser Asp Arg Ser Asn
1               5                   10                  15

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Synthetic
      vector insert oligonucleotide

<400> SEQUENCE: 11
atgatccatg gatttggagt acaccaaatc catggatgca                          40

<210> SEQ ID NO 12
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12 gtcggatcc                                                             9

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide linker
<220> FEATURE:
```

```
<221> NAME/KEY: modified_base
<222> LOCATION: (19)..(19)
<223> OTHER INFORMATION: a, c, t or g

<400> SEQUENCE: 13
atgatccatg gatccgacng tcggatccat ggatgca                             37

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Synthetic
      cloned oligonucleotide tag
<220> FEATURE:
<221> NAME/KEY: modified_base
<222> LOCATION: (19)..(19)
<223> OTHER INFORMATION: a, c, t or g

<400> SEQUENCE: 14
atgatccatg gatccgacng tcggatccat ggatgca                             37

<210> SEQ ID NO 15
<211> LENGTH: 13
<212> TYPE: DNA
<213> ORGANISM: Artificial Sequence
<220> FEATURE:
<223> OTHER INFORMATION: Description of Artificial Sequence: Synthetic
      top-strand oligonucleotide paired tag
<220> FEATURE:
<221> NAME/KEY: modified_base
<222> LOCATION: (9)..(9)
<223> OTHER INFORMATION: a, c, t or g

<400> SEQUENCE: 15
gatccgacng tcg                                                       13

<210> SEQ ID NO 16
<211> LENGTH: 13
<212> TYPE: DNA
<213> ORGANISM: Artificial Sequence
<220> FEATURE:
<223> OTHER INFORMATION: Description of Artificial Sequence: Synthetic
      bottom-strand oligonucleotide paired tag
<220> FEATURE:
<221> NAME/KEY: modified_base
<222> LOCATION: (9)..(9)
<223> OTHER INFORMATION: a, c, t or g

<400> SEQUENCE: 16
gatccgacng tcg                                                       13

<210> SEQ ID NO 17
<211> LENGTH: 8
<212> TYPE: DNA
<213> ORGANISM: Artificial Sequence
<220> FEATURE:
<223> OTHER INFORMATION: Description of Artificial Sequence: Synthetic
      restriction site oligonucleotide

<400> SEQUENCE: 17 gcgatcgc                                                              8

<210> SEQ ID NO 18
<211> LENGTH: 8
<212> TYPE: DNA
<213> ORGANISM: Artificial Sequence
<220> FEATURE:
<223> OTHER INFORMATION: Description of Artificial Sequence: Synthetic
``` restriction site oligonucleotide

<400> SEQUENCE: 18 gcggccgc                                                                  8

<210> SEQ ID NO 19
<211> LENGTH: 8
<212> TYPE: DNA
<213> ORGANISM: Artificial Sequence
<220> FEATURE:
<223> OTHER INFORMATION: Description of Artificial Sequence: Synthetic
      restriction site oligonucleotide

<400> SEQUENCE: 19 ttaattaa                                                                  8

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      top strand oligonucleotide linker

<400> SEQUENCE: 20
aaaaaattag cggccgctcc gac                                                23

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      bottom strand oligonucleotide linker
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (19)..(19)
<223> OTHER INFORMATION: 3' methyl

<400> SEQUENCE: 21
gtcggagcgg ccgctaatt                                                     19

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      top strand oligonucleotide linker
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (23)..(23)
<223> OTHER INFORMATION: 3' methyl

<400> SEQUENCE: 22
aaaaaatgat taattaatcc gac                                                23

<210> SEQ ID NO 23
<211> LENGTH: 19
<212> TYPE: DNA
<213> ORGANISM: Artificial Sequence -continued

```
<220> FEATURE:
<223> OTHER INFORMATION: Description of Artificial Sequence: Synthetic
      bottom strand oligonucleotide linker

<400> SEQUENCE: 23
gtcggattaa ttaatcatt                                                    19

<210> SEQ ID NO 24
<211> LENGTH: 10042
<212> TYPE: DNA
<213> ORGANISM: Artificial Sequence
<220> FEATURE:
<223> OTHER INFORMATION: Description of Artificial Sequence: Synthetic
      top strand polynucleotide cloned fragment
<220> FEATURE:
<221> NAME/KEY: modified_base
<222> LOCATION: (24)..(10023)
<223> OTHER INFORMATION: a, c, t or g

<400> SEQUENCE: 24
aaaaaattag cggccgctcc gacnnnnnnn nnnnnnnnnn nnnnnnnnnn nnnnnnnnnn       60
nnnnnnnnnn nnnnnnnnnn nnnnnnnnnn nnnnnnnnnn nnnnnnnnnn nnnnnnnnnn      120
nnnnnnnnnn nnnnnnnnnn nnnnnnnnnn nnnnnnnnnn nnnnnnnnnn nnnnnnnnnn      180
nnnnnnnnnn nnnnnnnnnn nnnnnnnnnn nnnnnnnnnn nnnnnnnnnn nnnnnnnnnn      240
nnnnnnnnnn nnnnnnnnnn nnnnnnnnnn nnnnnnnnnn nnnnnnnnnn nnnnnnnnnn      300
nnnnnnnnnn nnnnnnnnnn nnnnnnnnnn nnnnnnnnnn nnnnnnnnnn nnnnnnnnnn      360
nnnnnnnnnn nnnnnnnnnn nnnnnnnnnn nnnnnnnnnn nnnnnnnnnn nnnnnnnnnn      420
nnnnnnnnnn nnnnnnnnnn nnnnnnnnnn nnnnnnnnnn nnnnnnnnnn nnnnnnnnnn      480
nnnnnnnnnn nnnnnnnnnn nnnnnnnnnn nnnnnnnnnn nnnnnnnnnn nnnnnnnnnn      540
nnnnnnnnnn nnnnnnnnnn nnnnnnnnnn nnnnnnnnnn nnnnnnnnnn nnnnnnnnnn      600
nnnnnnnnnn nnnnnnnnnn nnnnnnnnnn nnnnnnnnnn nnnnnnnnnn nnnnnnnnnn      660
nnnnnnnnnn nnnnnnnnnn nnnnnnnnnn nnnnnnnnnn nnnnnnnnnn nnnnnnnnnn      720
nnnnnnnnnn nnnnnnnnnn nnnnnnnnnn nnnnnnnnnn nnnnnnnnnn nnnnnnnnnn      780
nnnnnnnnnn nnnnnnnnnn nnnnnnnnnn nnnnnnnnnn nnnnnnnnnn nnnnnnnnnn      840
nnnnnnnnnn nnnnnnnnnn nnnnnnnnnn nnnnnnnnnn nnnnnnnnnn nnnnnnnnnn      900
nnnnnnnnnn nnnnnnnnnn nnnnnnnnnn nnnnnnnnnn nnnnnnnnnn nnnnnnnnnn      960
nnnnnnnnnn nnnnnnnnnn nnnnnnnnnn nnnnnnnnnn nnnnnnnnnn nnnnnnnnnn     1020
nnnnnnnnnn nnnnnnnnnn nnnnnnnnnn nnnnnnnnnn nnnnnnnnnn nnnnnnnnnn     1080
nnnnnnnnnn nnnnnnnnnn nnnnnnnnnn nnnnnnnnnn nnnnnnnnnn nnnnnnnnnn     1140
nnnnnnnnnn nnnnnnnnnn nnnnnnnnnn nnnnnnnnnn nnnnnnnnnn nnnnnnnnnn     1200
nnnnnnnnnn nnnnnnnnnn nnnnnnnnnn nnnnnnnnnn nnnnnnnnnn nnnnnnnnnn     1260
nnnnnnnnnn nnnnnnnnnn nnnnnnnnnn nnnnnnnnnn nnnnnnnnnn nnnnnnnnnn     1320
nnnnnnnnnn nnnnnnnnnn nnnnnnnnnn nnnnnnnnnn nnnnnnnnnn nnnnnnnnnn     1380
nnnnnnnnnn nnnnnnnnnn nnnnnnnnnn nnnnnnnnnn nnnnnnnnnn nnnnnnnnnn     1440
nnnnnnnnnn nnnnnnnnnn nnnnnnnnnn nnnnnnnnnn nnnnnnnnnn nnnnnnnnnn     1500
nnnnnnnnnn nnnnnnnnnn nnnnnnnnnn nnnnnnnnnn nnnnnnnnnn nnnnnnnnnn     1560
nnnnnnnnnn nnnnnnnnnn nnnnnnnnnn nnnnnnnnnn nnnnnnnnnn nnnnnnnnnn     1620
nnnnnnnnnn nnnnnnnnnn nnnnnnnnnn nnnnnnnnnn nnnnnnnnnn nnnnnnnnnn     1680
```

```
nnnnnnnnnn nnnnnnnnnn nnnnnnnnnn nnnnnnnnnn nnnnnnnnnn nnnnnnnnnn     1740
nnnnnnnnnn nnnnnnnnnn nnnnnnnnnn nnnnnnnnnn nnnnnnnnnn nnnnnnnnnn     1800
nnnnnnnnnn nnnnnnnnnn nnnnnnnnnn nnnnnnnnnn nnnnnnnnnn nnnnnnnnnn     1860
nnnnnnnnnn nnnnnnnnnn nnnnnnnnnn nnnnnnnnnn nnnnnnnnnn nnnnnnnnnn     1920
nnnnnnnnnn nnnnnnnnnn nnnnnnnnnn nnnnnnnnnn nnnnnnnnnn nnnnnnnnnn     1980
nnnnnnnnnn nnnnnnnnnn nnnnnnnnnn nnnnnnnnnn nnnnnnnnnn nnnnnnnnnn     2040
nnnnnnnnnn nnnnnnnnnn nnnnnnnnnn nnnnnnnnnn nnnnnnnnnn nnnnnnnnnn     2100
nnnnnnnnnn nnnnnnnnnn nnnnnnnnnn nnnnnnnnnn nnnnnnnnnn nnnnnnnnnn     2160
nnnnnnnnnn nnnnnnnnnn nnnnnnnnnn nnnnnnnnnn nnnnnnnnnn nnnnnnnnnn     2220
nnnnnnnnnn nnnnnnnnnn nnnnnnnnnn nnnnnnnnnn nnnnnnnnnn nnnnnnnnnn     2280
nnnnnnnnnn nnnnnnnnnn nnnnnnnnnn nnnnnnnnnn nnnnnnnnnn nnnnnnnnnn     2340
nnnnnnnnnn nnnnnnnnnn nnnnnnnnnn nnnnnnnnnn nnnnnnnnnn nnnnnnnnnn     2400
nnnnnnnnnn nnnnnnnnnn nnnnnnnnnn nnnnnnnnnn nnnnnnnnnn nnnnnnnnnn     2460
nnnnnnnnnn nnnnnnnnnn nnnnnnnnnn nnnnnnnnnn nnnnnnnnnn nnnnnnnnnn     2520
nnnnnnnnnn nnnnnnnnnn nnnnnnnnnn nnnnnnnnnn nnnnnnnnnn nnnnnnnnnn     2580
nnnnnnnnnn nnnnnnnnnn nnnnnnnnnn nnnnnnnnnn nnnnnnnnnn nnnnnnnnnn     2640
nnnnnnnnnn nnnnnnnnnn nnnnnnnnnn nnnnnnnnnn nnnnnnnnnn nnnnnnnnnn     2700
nnnnnnnnnn nnnnnnnnnn nnnnnnnnnn nnnnnnnnnn nnnnnnnnnn nnnnnnnnnn     2760
nnnnnnnnnn nnnnnnnnnn nnnnnnnnnn nnnnnnnnnn nnnnnnnnnn nnnnnnnnnn     2820
nnnnnnnnnn nnnnnnnnnn nnnnnnnnnn nnnnnnnnnn nnnnnnnnnn nnnnnnnnnn     2880
nnnnnnnnnn nnnnnnnnnn nnnnnnnnnn nnnnnnnnnn nnnnnnnnnn nnnnnnnnnn     2940
nnnnnnnnnn nnnnnnnnnn nnnnnnnnnn nnnnnnnnnn nnnnnnnnnn nnnnnnnnnn     3000
nnnnnnnnnn nnnnnnnnnn nnnnnnnnnn nnnnnnnnnn nnnnnnnnnn nnnnnnnnnn     3060
nnnnnnnnnn nnnnnnnnnn nnnnnnnnnn nnnnnnnnnn nnnnnnnnnn nnnnnnnnnn     3120
nnnnnnnnnn nnnnnnnnnn nnnnnnnnnn nnnnnnnnnn nnnnnnnnnn nnnnnnnnnn     3180
nnnnnnnnnn nnnnnnnnnn nnnnnnnnnn nnnnnnnnnn nnnnnnnnnn nnnnnnnnnn     3240
nnnnnnnnnn nnnnnnnnnn nnnnnnnnnn nnnnnnnnnn nnnnnnnnnn nnnnnnnnnn     3300
nnnnnnnnnn nnnnnnnnnn nnnnnnnnnn nnnnnnnnnn nnnnnnnnnn nnnnnnnnnn     3360
nnnnnnnnnn nnnnnnnnnn nnnnnnnnnn nnnnnnnnnn nnnnnnnnnn nnnnnnnnnn     3420
nnnnnnnnnn nnnnnnnnnn nnnnnnnnnn nnnnnnnnnn nnnnnnnnnn nnnnnnnnnn     3480
nnnnnnnnnn nnnnnnnnnn nnnnnnnnnn nnnnnnnnnn nnnnnnnnnn nnnnnnnnnn     3540
nnnnnnnnnn nnnnnnnnnn nnnnnnnnnn nnnnnnnnnn nnnnnnnnnn nnnnnnnnnn     3600
nnnnnnnnnn nnnnnnnnnn nnnnnnnnnn nnnnnnnnnn nnnnnnnnnn nnnnnnnnnn     3660
nnnnnnnnnn nnnnnnnnnn nnnnnnnnnn nnnnnnnnnn nnnnnnnnnn nnnnnnnnnn     3720
nnnnnnnnnn nnnnnnnnnn nnnnnnnnnn nnnnnnnnnn nnnnnnnnnn nnnnnnnnnn     3780
nnnnnnnnnn nnnnnnnnnn nnnnnnnnnn nnnnnnnnnn nnnnnnnnnn nnnnnnnnnn     3840
nnnnnnnnnn nnnnnnnnnn nnnnnnnnnn nnnnnnnnnn nnnnnnnnnn nnnnnnnnnn     3900
nnnnnnnnnn nnnnnnnnnn nnnnnnnnnn nnnnnnnnnn nnnnnnnnnn nnnnnnnnnn     3960
nnnnnnnnnn nnnnnnnnnn nnnnnnnnnn nnnnnnnnnn nnnnnnnnnn nnnnnnnnnn     4020
nnnnnnnnnn nnnnnnnnnn nnnnnnnnnn nnnnnnnnnn nnnnnnnnnn nnnnnnnnnn     4080
```

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 4140 |
| nnnnnnnnnn | nnnnnnnnnn | nnnnnnnnnn | nnnnnnnnnn | nnnnnnnnnn | nnnnnnnnnn | 4200 |
| nnnnnnnnnn | nnnnnnnnnn | nnnnnnnnnn | nnnnnnnnnn | nnnnnnnnnn | nnnnnnnnnn | 4260 |
| nnnnnnnnnn | nnnnnnnnnn | nnnnnnnnnn | nnnnnnnnnn | nnnnnnnnnn | nnnnnnnnnn | 4320 |
| nnnnnnnnnn | nnnnnnnnnn | nnnnnnnnnn | nnnnnnnnnn | nnnnnnnnnn | nnnnnnnnnn | 4380 |
| nnnnnnnnnn | nnnnnnnnnn | nnnnnnnnnn | nnnnnnnnnn | nnnnnnnnnn | nnnnnnnnnn | 4440 |
| nnnnnnnnnn | nnnnnnnnnn | nnnnnnnnnn | nnnnnnnnnn | nnnnnnnnnn | nnnnnnnnnn | 4500 |
| nnnnnnnnnn | nnnnnnnnnn | nnnnnnnnnn | nnnnnnnnnn | nnnnnnnnnn | nnnnnnnnnn | 4560 |
| nnnnnnnnnn | nnnnnnnnnn | nnnnnnnnnn | nnnnnnnnnn | nnnnnnnnnn | nnnnnnnnnn | 4620 |
| nnnnnnnnnn | nnnnnnnnnn | nnnnnnnnnn | nnnnnnnnnn | nnnnnnnnnn | nnnnnnnnnn | 4680 |
| nnnnnnnnnn | nnnnnnnnnn | nnnnnnnnnn | nnnnnnnnnn | nnnnnnnnnn | nnnnnnnnnn | 4740 |
| nnnnnnnnnn | nnnnnnnnnn | nnnnnnnnnn | nnnnnnnnnn | nnnnnnnnnn | nnnnnnnnnn | 4800 |
| nnnnnnnnnn | nnnnnnnnnn | nnnnnnnnnn | nnnnnnnnnn | nnnnnnnnnn | nnnnnnnnnn | 4860 |
| nnnnnnnnnn | nnnnnnnnnn | nnnnnnnnnn | nnnnnnnnnn | nnnnnnnnnn | nnnnnnnnnn | 4920 |
| nnnnnnnnnn | nnnnnnnnnn | nnnnnnnnnn | nnnnnnnnnn | nnnnnnnnnn | nnnnnnnnnn | 4980 |
| nnnnnnnnnn | nnnnnnnnnn | nnnnnnnnnn | nnnnnnnnnn | nnnnnnnnnn | nnnnnnnnnn | 5040 |
| nnnnnnnnnn | nnnnnnnnnn | nnnnnnnnnn | nnnnnnnnnn | nnnnnnnnnn | nnnnnnnnnn | 5100 |
| nnnnnnnnnn | nnnnnnnnnn | nnnnnnnnnn | nnnnnnnnnn | nnnnnnnnnn | nnnnnnnnnn | 5160 |
| nnnnnnnnnn | nnnnnnnnnn | nnnnnnnnnn | nnnnnnnnnn | nnnnnnnnnn | nnnnnnnnnn | 5220 |
| nnnnnnnnnn | nnnnnnnnnn | nnnnnnnnnn | nnnnnnnnnn | nnnnnnnnnn | nnnnnnnnnn | 5280 |
| nnnnnnnnnn | nnnnnnnnnn | nnnnnnnnnn | nnnnnnnnnn | nnnnnnnnnn | nnnnnnnnnn | 5340 |
| nnnnnnnnnn | nnnnnnnnnn | nnnnnnnnnn | nnnnnnnnnn | nnnnnnnnnn | nnnnnnnnnn | 5400 |
| nnnnnnnnnn | nnnnnnnnnn | nnnnnnnnnn | nnnnnnnnnn | nnnnnnnnnn | nnnnnnnnnn | 5460 |
| nnnnnnnnnn | nnnnnnnnnn | nnnnnnnnnn | nnnnnnnnnn | nnnnnnnnnn | nnnnnnnnnn | 5520 |
| nnnnnnnnnn | nnnnnnnnnn | nnnnnnnnnn | nnnnnnnnnn | nnnnnnnnnn | nnnnnnnnnn | 5580 |
| nnnnnnnnnn | nnnnnnnnnn | nnnnnnnnnn | nnnnnnnnnn | nnnnnnnnnn | nnnnnnnnnn | 5640 |
| nnnnnnnnnn | nnnnnnnnnn | nnnnnnnnnn | nnnnnnnnnn | nnnnnnnnnn | nnnnnnnnnn | 5700 |
| nnnnnnnnnn | nnnnnnnnnn | nnnnnnnnnn | nnnnnnnnnn | nnnnnnnnnn | nnnnnnnnnn | 5760 |
| nnnnnnnnnn | nnnnnnnnnn | nnnnnnnnnn | nnnnnnnnnn | nnnnnnnnnn | nnnnnnnnnn | 5820 |
| nnnnnnnnnn | nnnnnnnnnn | nnnnnnnnnn | nnnnnnnnnn | nnnnnnnnnn | nnnnnnnnnn | 5880 |
| nnnnnnnnnn | nnnnnnnnnn | nnnnnnnnnn | nnnnnnnnnn | nnnnnnnnnn | nnnnnnnnnn | 5940 |
| nnnnnnnnnn | nnnnnnnnnn | nnnnnnnnnn | nnnnnnnnnn | nnnnnnnnnn | nnnnnnnnnn | 6000 |
| nnnnnnnnnn | nnnnnnnnnn | nnnnnnnnnn | nnnnnnnnnn | nnnnnnnnnn | nnnnnnnnnn | 6060 |
| nnnnnnnnnn | nnnnnnnnnn | nnnnnnnnnn | nnnnnnnnnn | nnnnnnnnnn | nnnnnnnnnn | 6120 |
| nnnnnnnnnn | nnnnnnnnnn | nnnnnnnnnn | nnnnnnnnnn | nnnnnnnnnn | nnnnnnnnnn | 6180 |
| nnnnnnnnnn | nnnnnnnnnn | nnnnnnnnnn | nnnnnnnnnn | nnnnnnnnnn | nnnnnnnnnn | 6240 |
| nnnnnnnnnn | nnnnnnnnnn | nnnnnnnnnn | nnnnnnnnnn | nnnnnnnnnn | nnnnnnnnnn | 6300 |
| nnnnnnnnnn | nnnnnnnnnn | nnnnnnnnnn | nnnnnnnnnn | nnnnnnnnnn | nnnnnnnnnn | 6360 |
| nnnnnnnnnn | nnnnnnnnnn | nnnnnnnnnn | nnnnnnnnnn | nnnnnnnnnn | nnnnnnnnnn | 6420 |

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 6480 |
| nnnnnnnnnn | nnnnnnnnnn | nnnnnnnnnn | nnnnnnnnnn | nnnnnnnnnn | nnnnnnnnnn | 6540 |
| nnnnnnnnnn | nnnnnnnnnn | nnnnnnnnnn | nnnnnnnnnn | nnnnnnnnnn | nnnnnnnnnn | 6600 |
| nnnnnnnnnn | nnnnnnnnnn | nnnnnnnnnn | nnnnnnnnnn | nnnnnnnnnn | nnnnnnnnnn | 6660 |
| nnnnnnnnnn | nnnnnnnnnn | nnnnnnnnnn | nnnnnnnnnn | nnnnnnnnnn | nnnnnnnnnn | 6720 |
| nnnnnnnnnn | nnnnnnnnnn | nnnnnnnnnn | nnnnnnnnnn | nnnnnnnnnn | nnnnnnnnnn | 6780 |
| nnnnnnnnnn | nnnnnnnnnn | nnnnnnnnnn | nnnnnnnnnn | nnnnnnnnnn | nnnnnnnnnn | 6840 |
| nnnnnnnnnn | nnnnnnnnnn | nnnnnnnnnn | nnnnnnnnnn | nnnnnnnnnn | nnnnnnnnnn | 6900 |
| nnnnnnnnnn | nnnnnnnnnn | nnnnnnnnnn | nnnnnnnnnn | nnnnnnnnnn | nnnnnnnnnn | 6960 |
| nnnnnnnnnn | nnnnnnnnnn | nnnnnnnnnn | nnnnnnnnnn | nnnnnnnnnn | nnnnnnnnnn | 7020 |
| nnnnnnnnnn | nnnnnnnnnn | nnnnnnnnnn | nnnnnnnnnn | nnnnnnnnnn | nnnnnnnnnn | 7080 |
| nnnnnnnnnn | nnnnnnnnnn | nnnnnnnnnn | nnnnnnnnnn | nnnnnnnnnn | nnnnnnnnnn | 7140 |
| nnnnnnnnnn | nnnnnnnnnn | nnnnnnnnnn | nnnnnnnnnn | nnnnnnnnnn | nnnnnnnnnn | 7200 |
| nnnnnnnnnn | nnnnnnnnnn | nnnnnnnnnn | nnnnnnnnnn | nnnnnnnnnn | nnnnnnnnnn | 7260 |
| nnnnnnnnnn | nnnnnnnnnn | nnnnnnnnnn | nnnnnnnnnn | nnnnnnnnnn | nnnnnnnnnn | 7320 |
| nnnnnnnnnn | nnnnnnnnnn | nnnnnnnnnn | nnnnnnnnnn | nnnnnnnnnn | nnnnnnnnnn | 7380 |
| nnnnnnnnnn | nnnnnnnnnn | nnnnnnnnnn | nnnnnnnnnn | nnnnnnnnnn | nnnnnnnnnn | 7440 |
| nnnnnnnnnn | nnnnnnnnnn | nnnnnnnnnn | nnnnnnnnnn | nnnnnnnnnn | nnnnnnnnnn | 7500 |
| nnnnnnnnnn | nnnnnnnnnn | nnnnnnnnnn | nnnnnnnnnn | nnnnnnnnnn | nnnnnnnnnn | 7560 |
| nnnnnnnnnn | nnnnnnnnnn | nnnnnnnnnn | nnnnnnnnnn | nnnnnnnnnn | nnnnnnnnnn | 7620 |
| nnnnnnnnnn | nnnnnnnnnn | nnnnnnnnnn | nnnnnnnnnn | nnnnnnnnnn | nnnnnnnnnn | 7680 |
| nnnnnnnnnn | nnnnnnnnnn | nnnnnnnnnn | nnnnnnnnnn | nnnnnnnnnn | nnnnnnnnnn | 7740 |
| nnnnnnnnnn | nnnnnnnnnn | nnnnnnnnnn | nnnnnnnnnn | nnnnnnnnnn | nnnnnnnnnn | 7800 |
| nnnnnnnnnn | nnnnnnnnnn | nnnnnnnnnn | nnnnnnnnnn | nnnnnnnnnn | nnnnnnnnnn | 7860 |
| nnnnnnnnnn | nnnnnnnnnn | nnnnnnnnnn | nnnnnnnnnn | nnnnnnnnnn | nnnnnnnnnn | 7920 |
| nnnnnnnnnn | nnnnnnnnnn | nnnnnnnnnn | nnnnnnnnnn | nnnnnnnnnn | nnnnnnnnnn | 7980 |
| nnnnnnnnnn | nnnnnnnnnn | nnnnnnnnnn | nnnnnnnnnn | nnnnnnnnnn | nnnnnnnnnn | 8040 |
| nnnnnnnnnn | nnnnnnnnnn | nnnnnnnnnn | nnnnnnnnnn | nnnnnnnnnn | nnnnnnnnnn | 8100 |
| nnnnnnnnnn | nnnnnnnnnn | nnnnnnnnnn | nnnnnnnnnn | nnnnnnnnnn | nnnnnnnnnn | 8160 |
| nnnnnnnnnn | nnnnnnnnnn | nnnnnnnnnn | nnnnnnnnnn | nnnnnnnnnn | nnnnnnnnnn | 8220 |
| nnnnnnnnnn | nnnnnnnnnn | nnnnnnnnnn | nnnnnnnnnn | nnnnnnnnnn | nnnnnnnnnn | 8280 |
| nnnnnnnnnn | nnnnnnnnnn | nnnnnnnnnn | nnnnnnnnnn | nnnnnnnnnn | nnnnnnnnnn | 8340 |
| nnnnnnnnnn | nnnnnnnnnn | nnnnnnnnnn | nnnnnnnnnn | nnnnnnnnnn | nnnnnnnnnn | 8400 |
| nnnnnnnnnn | nnnnnnnnnn | nnnnnnnnnn | nnnnnnnnnn | nnnnnnnnnn | nnnnnnnnnn | 8460 |
| nnnnnnnnnn | nnnnnnnnnn | nnnnnnnnnn | nnnnnnnnnn | nnnnnnnnnn | nnnnnnnnnn | 8520 |
| nnnnnnnnnn | nnnnnnnnnn | nnnnnnnnnn | nnnnnnnnnn | nnnnnnnnnn | nnnnnnnnnn | 8580 |
| nnnnnnnnnn | nnnnnnnnnn | nnnnnnnnnn | nnnnnnnnnn | nnnnnnnnnn | nnnnnnnnnn | 8640 |
| nnnnnnnnnn | nnnnnnnnnn | nnnnnnnnnn | nnnnnnnnnn | nnnnnnnnnn | nnnnnnnnnn | 8700 |
| nnnnnnnnnn | nnnnnnnnnn | nnnnnnnnnn | nnnnnnnnnn | nnnnnnnnnn | nnnnnnnnnn | 8760 |
| nnnnnnnnnn | nnnnnnnnnn | nnnnnnnnnn | nnnnnnnnnn | nnnnnnnnnn | nnnnnnnnnn | 8820 |

```
nnnnnnnnnn nnnnnnnnnn nnnnnnnnnn nnnnnnnnnn nnnnnnnnnn nnnnnnnnnn    8880
nnnnnnnnnn nnnnnnnnnn nnnnnnnnnn nnnnnnnnnn nnnnnnnnnn nnnnnnnnnn    8940
nnnnnnnnnn nnnnnnnnnn nnnnnnnnnn nnnnnnnnnn nnnnnnnnnn nnnnnnnnnn    9000
nnnnnnnnnn nnnnnnnnnn nnnnnnnnnn nnnnnnnnnn nnnnnnnnnn nnnnnnnnnn    9060
nnnnnnnnnn nnnnnnnnnn nnnnnnnnnn nnnnnnnnnn nnnnnnnnnn nnnnnnnnnn    9120
nnnnnnnnnn nnnnnnnnnn nnnnnnnnnn nnnnnnnnnn nnnnnnnnnn nnnnnnnnnn    9180
nnnnnnnnnn nnnnnnnnnn nnnnnnnnnn nnnnnnnnnn nnnnnnnnnn nnnnnnnnnn    9240
nnnnnnnnnn nnnnnnnnnn nnnnnnnnnn nnnnnnnnnn nnnnnnnnnn nnnnnnnnnn    9300
nnnnnnnnnn nnnnnnnnnn nnnnnnnnnn nnnnnnnnnn nnnnnnnnnn nnnnnnnnnn    9360
nnnnnnnnnn nnnnnnnnnn nnnnnnnnnn nnnnnnnnnn nnnnnnnnnn nnnnnnnnnn    9420
nnnnnnnnnn nnnnnnnnnn nnnnnnnnnn nnnnnnnnnn nnnnnnnnnn nnnnnnnnnn    9480
nnnnnnnnnn nnnnnnnnnn nnnnnnnnnn nnnnnnnnnn nnnnnnnnnn nnnnnnnnnn    9540
nnnnnnnnnn nnnnnnnnnn nnnnnnnnnn nnnnnnnnnn nnnnnnnnnn nnnnnnnnnn    9600
nnnnnnnnnn nnnnnnnnnn nnnnnnnnnn nnnnnnnnnn nnnnnnnnnn nnnnnnnnnn    9660
nnnnnnnnnn nnnnnnnnnn nnnnnnnnnn nnnnnnnnnn nnnnnnnnnn nnnnnnnnnn    9720
nnnnnnnnnn nnnnnnnnnn nnnnnnnnnn nnnnnnnnnn nnnnnnnnnn nnnnnnnnnn    9780
nnnnnnnnnn nnnnnnnnnn nnnnnnnnnn nnnnnnnnnn nnnnnnnnnn nnnnnnnnnn    9840
nnnnnnnnnn nnnnnnnnnn nnnnnnnnnn nnnnnnnnnn nnnnnnnnnn nnnnnnnnnn    9900
nnnnnnnnnn nnnnnnnnnn nnnnnnnnnn nnnnnnnnnn nnnnnnnnnn nnnnnnnnnn    9960
nnnnnnnnnn nnnnnnnnnn nnnnnnnnnn nnnnnnnnnn nnnnnnnnnn nnnnnnnnnn   10020
nnngtcggag cggccgctaa tt                                             10042

<210> SEQ ID NO 25
<211> LENGTH: 10042
<212> TYPE: DNA
<213> ORGANISM: Artificial Sequence
<220> FEATURE:
<223> OTHER INFORMATION: Description of Artificial Sequence: Synthetic
      bottom strand polynucleotide cloned fragment
<220> FEATURE:
<221> NAME/KEY: modified_base
<222> LOCATION: (24)..(10023)
<223> OTHER INFORMATION: a, c, t or g

<400> SEQUENCE: 25
aaaaaattag cggccgctcc gacnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
```

```
nnnnnnnnnn nnnnnnnnnn nnnnnnnnnn nnnnnnnnnn nnnnnnnnnn nnnnnnnnnn         720
nnnnnnnnnn nnnnnnnnnn nnnnnnnnnn nnnnnnnnnn nnnnnnnnnn nnnnnnnnnn         780
nnnnnnnnnn nnnnnnnnnn nnnnnnnnnn nnnnnnnnnn nnnnnnnnnn nnnnnnnnnn         840
nnnnnnnnnn nnnnnnnnnn nnnnnnnnnn nnnnnnnnnn nnnnnnnnnn nnnnnnnnnn         900
nnnnnnnnnn nnnnnnnnnn nnnnnnnnnn nnnnnnnnnn nnnnnnnnnn nnnnnnnnnn         960
nnnnnnnnnn nnnnnnnnnn nnnnnnnnnn nnnnnnnnnn nnnnnnnnnn nnnnnnnnnn        1020
nnnnnnnnnn nnnnnnnnnn nnnnnnnnnn nnnnnnnnnn nnnnnnnnnn nnnnnnnnnn        1080
nnnnnnnnnn nnnnnnnnnn nnnnnnnnnn nnnnnnnnnn nnnnnnnnnn nnnnnnnnnn        1140
nnnnnnnnnn nnnnnnnnnn nnnnnnnnnn nnnnnnnnnn nnnnnnnnnn nnnnnnnnnn        1200
nnnnnnnnnn nnnnnnnnnn nnnnnnnnnn nnnnnnnnnn nnnnnnnnnn nnnnnnnnnn        1260
nnnnnnnnnn nnnnnnnnnn nnnnnnnnnn nnnnnnnnnn nnnnnnnnnn nnnnnnnnnn        1320
nnnnnnnnnn nnnnnnnnnn nnnnnnnnnn nnnnnnnnnn nnnnnnnnnn nnnnnnnnnn        1380
nnnnnnnnnn nnnnnnnnnn nnnnnnnnnn nnnnnnnnnn nnnnnnnnnn nnnnnnnnnn        1440
nnnnnnnnnn nnnnnnnnnn nnnnnnnnnn nnnnnnnnnn nnnnnnnnnn nnnnnnnnnn        1500
nnnnnnnnnn nnnnnnnnnn nnnnnnnnnn nnnnnnnnnn nnnnnnnnnn nnnnnnnnnn        1560
nnnnnnnnnn nnnnnnnnnn nnnnnnnnnn nnnnnnnnnn nnnnnnnnnn nnnnnnnnnn        1620
nnnnnnnnnn nnnnnnnnnn nnnnnnnnnn nnnnnnnnnn nnnnnnnnnn nnnnnnnnnn        1680
nnnnnnnnnn nnnnnnnnnn nnnnnnnnnn nnnnnnnnnn nnnnnnnnnn nnnnnnnnnn        1740
nnnnnnnnnn nnnnnnnnnn nnnnnnnnnn nnnnnnnnnn nnnnnnnnnn nnnnnnnnnn        1800
nnnnnnnnnn nnnnnnnnnn nnnnnnnnnn nnnnnnnnnn nnnnnnnnnn nnnnnnnnnn        1860
nnnnnnnnnn nnnnnnnnnn nnnnnnnnnn nnnnnnnnnn nnnnnnnnnn nnnnnnnnnn        1920
nnnnnnnnnn nnnnnnnnnn nnnnnnnnnn nnnnnnnnnn nnnnnnnnnn nnnnnnnnnn        1980
nnnnnnnnnn nnnnnnnnnn nnnnnnnnnn nnnnnnnnnn nnnnnnnnnn nnnnnnnnnn        2040
nnnnnnnnnn nnnnnnnnnn nnnnnnnnnn nnnnnnnnnn nnnnnnnnnn nnnnnnnnnn        2100
nnnnnnnnnn nnnnnnnnnn nnnnnnnnnn nnnnnnnnnn nnnnnnnnnn nnnnnnnnnn        2160
nnnnnnnnnn nnnnnnnnnn nnnnnnnnnn nnnnnnnnnn nnnnnnnnnn nnnnnnnnnn        2220
nnnnnnnnnn nnnnnnnnnn nnnnnnnnnn nnnnnnnnnn nnnnnnnnnn nnnnnnnnnn        2280
nnnnnnnnnn nnnnnnnnnn nnnnnnnnnn nnnnnnnnnn nnnnnnnnnn nnnnnnnnnn        2340
nnnnnnnnnn nnnnnnnnnn nnnnnnnnnn nnnnnnnnnn nnnnnnnnnn nnnnnnnnnn        2400
nnnnnnnnnn nnnnnnnnnn nnnnnnnnnn nnnnnnnnnn nnnnnnnnnn nnnnnnnnnn        2460
nnnnnnnnnn nnnnnnnnnn nnnnnnnnnn nnnnnnnnnn nnnnnnnnnn nnnnnnnnnn        2520
nnnnnnnnnn nnnnnnnnnn nnnnnnnnnn nnnnnnnnnn nnnnnnnnnn nnnnnnnnnn        2580
nnnnnnnnnn nnnnnnnnnn nnnnnnnnnn nnnnnnnnnn nnnnnnnnnn nnnnnnnnnn        2640
nnnnnnnnnn nnnnnnnnnn nnnnnnnnnn nnnnnnnnnn nnnnnnnnnn nnnnnnnnnn        2700
nnnnnnnnnn nnnnnnnnnn nnnnnnnnnn nnnnnnnnnn nnnnnnnnnn nnnnnnnnnn        2760
nnnnnnnnnn nnnnnnnnnn nnnnnnnnnn nnnnnnnnnn nnnnnnnnnn nnnnnnnnnn        2820
nnnnnnnnnn nnnnnnnnnn nnnnnnnnnn nnnnnnnnnn nnnnnnnnnn nnnnnnnnnn        2880
nnnnnnnnnn nnnnnnnnnn nnnnnnnnnn nnnnnnnnnn nnnnnnnnnn nnnnnnnnnn        2940
nnnnnnnnnn nnnnnnnnnn nnnnnnnnnn nnnnnnnnnn nnnnnnnnnn nnnnnnnnnn        3000
```

```
nnnnnnnnnn nnnnnnnnnn nnnnnnnnnn nnnnnnnnnn nnnnnnnnnn nnnnnnnnnn    3060
nnnnnnnnnn nnnnnnnnnn nnnnnnnnnn nnnnnnnnnn nnnnnnnnnn nnnnnnnnnn    3120
nnnnnnnnnn nnnnnnnnnn nnnnnnnnnn nnnnnnnnnn nnnnnnnnnn nnnnnnnnnn    3180
nnnnnnnnnn nnnnnnnnnn nnnnnnnnnn nnnnnnnnnn nnnnnnnnnn nnnnnnnnnn    3240
nnnnnnnnnn nnnnnnnnnn nnnnnnnnnn nnnnnnnnnn nnnnnnnnnn nnnnnnnnnn    3300
nnnnnnnnnn nnnnnnnnnn nnnnnnnnnn nnnnnnnnnn nnnnnnnnnn nnnnnnnnnn    3360
nnnnnnnnnn nnnnnnnnnn nnnnnnnnnn nnnnnnnnnn nnnnnnnnnn nnnnnnnnnn    3420
nnnnnnnnnn nnnnnnnnnn nnnnnnnnnn nnnnnnnnnn nnnnnnnnnn nnnnnnnnnn    3480
nnnnnnnnnn nnnnnnnnnn nnnnnnnnnn nnnnnnnnnn nnnnnnnnnn nnnnnnnnnn    3540
nnnnnnnnnn nnnnnnnnnn nnnnnnnnnn nnnnnnnnnn nnnnnnnnnn nnnnnnnnnn    3600
nnnnnnnnnn nnnnnnnnnn nnnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn nnnnnnnnnn    3720
nnnnnnnnnn nnnnnnnnnn nnnnnnnnnn nnnnnnnnnn nnnnnnnnnn nnnnnnnnnn    3780
nnnnnnnnnn nnnnnnnnnn nnnnnnnnnn nnnnnnnnnn nnnnnnnnnn nnnnnnnnnn    3840
nnnnnnnnnn nnnnnnnnnn nnnnnnnnnn nnnnnnnnnn nnnnnnnnnn nnnnnnnnnn    3900
nnnnnnnnnn nnnnnnnnnn nnnnnnnnnn nnnnnnnnnn nnnnnnnnnn nnnnnnnnnn    3960
nnnnnnnnnn nnnnnnnnnn nnnnnnnnnn nnnnnnnnnn nnnnnnnnnn nnnnnnnnnn    4020
nnnnnnnnnn nnnnnnnnnn nnnnnnnnnn nnnnnnnnnn nnnnnnnnnn nnnnnnnnnn    4080
nnnnnnnnnn nnnnnnnnnn nnnnnnnnnn nnnnnnnnnn nnnnnnnnnn nnnnnnnnnn    4140
nnnnnnnnnn nnnnnnnnnn nnnnnnnnnn nnnnnnnnnn nnnnnnnnnn nnnnnnnnnn    4200
nnnnnnnnnn nnnnnnnnnn nnnnnnnnnn nnnnnnnnnn nnnnnnnnnn nnnnnnnnnn    4260
nnnnnnnnnn nnnnnnnnnn nnnnnnnnnn nnnnnnnnnn nnnnnnnnnn nnnnnnnnnn    4320
nnnnnnnnnn nnnnnnnnnn nnnnnnnnnn nnnnnnnnnn nnnnnnnnnn nnnnnnnnnn    4380
nnnnnnnnnn nnnnnnnnnn nnnnnnnnnn nnnnnnnnnn nnnnnnnnnn nnnnnnnnnn    4440
nnnnnnnnnn nnnnnnnnnn nnnnnnnnnn nnnnnnnnnn nnnnnnnnnn nnnnnnnnnn    4500
nnnnnnnnnn nnnnnnnnnn nnnnnnnnnn nnnnnnnnnn nnnnnnnnnn nnnnnnnnnn    4560
nnnnnnnnnn nnnnnnnnnn nnnnnnnnnn nnnnnnnnnn nnnnnnnnnn nnnnnnnnnn    4620
nnnnnnnnnn nnnnnnnnnn nnnnnnnnnn nnnnnnnnnn nnnnnnnnnn nnnnnnnnnn    4680
nnnnnnnnnn nnnnnnnnnn nnnnnnnnnn nnnnnnnnnn nnnnnnnnnn nnnnnnnnnn    4740
nnnnnnnnnn nnnnnnnnnn nnnnnnnnnn nnnnnnnnnn nnnnnnnnnn nnnnnnnnnn    4800
nnnnnnnnnn nnnnnnnnnn nnnnnnnnnn nnnnnnnnnn nnnnnnnnnn nnnnnnnnnn    4860
nnnnnnnnnn nnnnnnnnnn nnnnnnnnnn nnnnnnnnnn nnnnnnnnnn nnnnnnnnnn    4920
nnnnnnnnnn nnnnnnnnnn nnnnnnnnnn nnnnnnnnnn nnnnnnnnnn nnnnnnnnnn    4980
nnnnnnnnnn nnnnnnnnnn nnnnnnnnnn nnnnnnnnnn nnnnnnnnnn nnnnnnnnnn    5040
nnnnnnnnnn nnnnnnnnnn nnnnnnnnnn nnnnnnnnnn nnnnnnnnnn nnnnnnnnnn    5100
nnnnnnnnnn nnnnnnnnnn nnnnnnnnnn nnnnnnnnnn nnnnnnnnnn nnnnnnnnnn    5160
nnnnnnnnnn nnnnnnnnnn nnnnnnnnnn nnnnnnnnnn nnnnnnnnnn nnnnnnnnnn    5220
nnnnnnnnnn nnnnnnnnnn nnnnnnnnnn nnnnnnnnnn nnnnnnnnnn nnnnnnnnnn    5280
nnnnnnnnnn nnnnnnnnnn nnnnnnnnnn nnnnnnnnnn nnnnnnnnnn nnnnnnnnnn    5340
nnnnnnnnnn nnnnnnnnnn nnnnnnnnnn nnnnnnnnnn nnnnnnnnnn nnnnnnnnnn    5400
```

| | |
|---|---|
| nnnnnnnnnn nnnnnnnnnn nnnnnnnnnn nnnnnnnnnn nnnnnnnnnn nnnnnnnnnn | 5460 |
| nnnnnnnnnn nnnnnnnnnn nnnnnnnnnn nnnnnnnnnn nnnnnnnnnn nnnnnnnnnn | 5520 |
| nnnnnnnnnn nnnnnnnnnn nnnnnnnnnn nnnnnnnnnn nnnnnnnnnn nnnnnnnnnn | 5580 |
| nnnnnnnnnn nnnnnnnnnn nnnnnnnnnn nnnnnnnnnn nnnnnnnnnn nnnnnnnnnn | 5640 |
| nnnnnnnnnn nnnnnnnnnn nnnnnnnnnn nnnnnnnnnn nnnnnnnnnn nnnnnnnnnn | 5700 |
| nnnnnnnnnn nnnnnnnnnn nnnnnnnnnn nnnnnnnnnn nnnnnnnnnn nnnnnnnnnn | 5760 |
| nnnnnnnnnn nnnnnnnnnn nnnnnnnnnn nnnnnnnnnn nnnnnnnnnn nnnnnnnnnn | 5820 |
| nnnnnnnnnn nnnnnnnnnn nnnnnnnnnn nnnnnnnnnn nnnnnnnnnn nnnnnnnnnn | 5880 |
| nnnnnnnnnn nnnnnnnnnn nnnnnnnnnn nnnnnnnnnn nnnnnnnnnn nnnnnnnnnn | 5940 |
| nnnnnnnnnn nnnnnnnnnn nnnnnnnnnn nnnnnnnnnn nnnnnnnnnn nnnnnnnnnn | 6000 |
| nnnnnnnnnn nnnnnnnnnn nnnnnnnnnn nnnnnnnnnn nnnnnnnnnn nnnnnnnnnn | 6060 |
| nnnnnnnnnn nnnnnnnnnn nnnnnnnnnn nnnnnnnnnn nnnnnnnnnn nnnnnnnnnn | 6120 |
| nnnnnnnnnn nnnnnnnnnn nnnnnnnnnn nnnnnnnnnn nnnnnnnnnn nnnnnnnnnn | 6180 |
| nnnnnnnnnn nnnnnnnnnn nnnnnnnnnn nnnnnnnnnn nnnnnnnnnn nnnnnnnnnn | 6240 |
| nnnnnnnnnn nnnnnnnnnn nnnnnnnnnn nnnnnnnnnn nnnnnnnnnn nnnnnnnnnn | 6300 |
| nnnnnnnnnn nnnnnnnnnn nnnnnnnnnn nnnnnnnnnn nnnnnnnnnn nnnnnnnnnn | 6360 |
| nnnnnnnnnn nnnnnnnnnn nnnnnnnnnn nnnnnnnnnn nnnnnnnnnn nnnnnnnnnn | 6420 |
| nnnnnnnnnn nnnnnnnnnn nnnnnnnnnn nnnnnnnnnn nnnnnnnnnn nnnnnnnnnn | 6480 |
| nnnnnnnnnn nnnnnnnnnn nnnnnnnnnn nnnnnnnnnn nnnnnnnnnn nnnnnnnnnn | 6540 |
| nnnnnnnnnn nnnnnnnnnn nnnnnnnnnn nnnnnnnnnn nnnnnnnnnn nnnnnnnnnn | 6600 |
| nnnnnnnnnn nnnnnnnnnn nnnnnnnnnn nnnnnnnnnn nnnnnnnnnn nnnnnnnnnn | 6660 |
| nnnnnnnnnn nnnnnnnnnn nnnnnnnnnn nnnnnnnnnn nnnnnnnnnn nnnnnnnnnn | 6720 |
| nnnnnnnnnn nnnnnnnnnn nnnnnnnnnn nnnnnnnnnn nnnnnnnnnn nnnnnnnnnn | 6780 |
| nnnnnnnnnn nnnnnnnnnn nnnnnnnnnn nnnnnnnnnn nnnnnnnnnn nnnnnnnnnn | 6840 |
| nnnnnnnnnn nnnnnnnnnn nnnnnnnnnn nnnnnnnnnn nnnnnnnnnn nnnnnnnnnn | 6900 |
| nnnnnnnnnn nnnnnnnnnn nnnnnnnnnn nnnnnnnnnn nnnnnnnnnn nnnnnnnnnn | 6960 |
| nnnnnnnnnn nnnnnnnnnn nnnnnnnnnn nnnnnnnnnn nnnnnnnnnn nnnnnnnnnn | 7020 |
| nnnnnnnnnn nnnnnnnnnn nnnnnnnnnn nnnnnnnnnn nnnnnnnnnn nnnnnnnnnn | 7080 |
| nnnnnnnnnn nnnnnnnnnn nnnnnnnnnn nnnnnnnnnn nnnnnnnnnn nnnnnnnnnn | 7140 |
| nnnnnnnnnn nnnnnnnnnn nnnnnnnnnn nnnnnnnnnn nnnnnnnnnn nnnnnnnnnn | 7200 |
| nnnnnnnnnn nnnnnnnnnn nnnnnnnnnn nnnnnnnnnn nnnnnnnnnn nnnnnnnnnn | 7260 |
| nnnnnnnnnn nnnnnnnnnn nnnnnnnnnn nnnnnnnnnn nnnnnnnnnn nnnnnnnnnn | 7320 |
| nnnnnnnnnn nnnnnnnnnn nnnnnnnnnn nnnnnnnnnn nnnnnnnnnn nnnnnnnnnn | 7380 |
| nnnnnnnnnn nnnnnnnnnn nnnnnnnnnn nnnnnnnnnn nnnnnnnnnn nnnnnnnnnn | 7440 |
| nnnnnnnnnn nnnnnnnnnn nnnnnnnnnn nnnnnnnnnn nnnnnnnnnn nnnnnnnnnn | 7500 |
| nnnnnnnnnn nnnnnnnnnn nnnnnnnnnn nnnnnnnnnn nnnnnnnnnn nnnnnnnnnn | 7560 |
| nnnnnnnnnn nnnnnnnnnn nnnnnnnnnn nnnnnnnnnn nnnnnnnnnn nnnnnnnnnn | 7620 |
| nnnnnnnnnn nnnnnnnnnn nnnnnnnnnn nnnnnnnnnn nnnnnnnnnn nnnnnnnnnn | 7680 |
| nnnnnnnnnn nnnnnnnnnn nnnnnnnnnn nnnnnnnnnn nnnnnnnnnn nnnnnnnnnn | 7740 |

| | |
|---|---|
| nnnnnnnnnn nnnnnnnnnn nnnnnnnnnn nnnnnnnnnn nnnnnnnnnn nnnnnnnnnn | 7800 |
| nnnnnnnnnn nnnnnnnnnn nnnnnnnnnn nnnnnnnnnn nnnnnnnnnn nnnnnnnnnn | 7860 |
| nnnnnnnnnn nnnnnnnnnn nnnnnnnnnn nnnnnnnnnn nnnnnnnnnn nnnnnnnnnn | 7920 |
| nnnnnnnnnn nnnnnnnnnn nnnnnnnnnn nnnnnnnnnn nnnnnnnnnn nnnnnnnnnn | 7980 |
| nnnnnnnnnn nnnnnnnnnn nnnnnnnnnn nnnnnnnnnn nnnnnnnnnn nnnnnnnnnn | 8040 |
| nnnnnnnnnn nnnnnnnnnn nnnnnnnnnn nnnnnnnnnn nnnnnnnnnn nnnnnnnnnn | 8100 |
| nnnnnnnnnn nnnnnnnnnn nnnnnnnnnn nnnnnnnnnn nnnnnnnnnn nnnnnnnnnn | 8160 |
| nnnnnnnnnn nnnnnnnnnn nnnnnnnnnn nnnnnnnnnn nnnnnnnnnn nnnnnnnnnn | 8220 |
| nnnnnnnnnn nnnnnnnnnn nnnnnnnnnn nnnnnnnnnn nnnnnnnnnn nnnnnnnnnn | 8280 |
| nnnnnnnnnn nnnnnnnnnn nnnnnnnnnn nnnnnnnnnn nnnnnnnnnn nnnnnnnnnn | 8340 |
| nnnnnnnnnn nnnnnnnnnn nnnnnnnnnn nnnnnnnnnn nnnnnnnnnn nnnnnnnnnn | 8400 |
| nnnnnnnnnn nnnnnnnnnn nnnnnnnnnn nnnnnnnnnn nnnnnnnnnn nnnnnnnnnn | 8460 |
| nnnnnnnnnn nnnnnnnnnn nnnnnnnnnn nnnnnnnnnn nnnnnnnnnn nnnnnnnnnn | 8520 |
| nnnnnnnnnn nnnnnnnnnn nnnnnnnnnn nnnnnnnnnn nnnnnnnnnn nnnnnnnnnn | 8580 |
| nnnnnnnnnn nnnnnnnnnn nnnnnnnnnn nnnnnnnnnn nnnnnnnnnn nnnnnnnnnn | 8640 |
| nnnnnnnnnn nnnnnnnnnn nnnnnnnnnn nnnnnnnnnn nnnnnnnnnn nnnnnnnnnn | 8700 |
| nnnnnnnnnn nnnnnnnnnn nnnnnnnnnn nnnnnnnnnn nnnnnnnnnn nnnnnnnnnn | 8760 |
| nnnnnnnnnn nnnnnnnnnn nnnnnnnnnn nnnnnnnnnn nnnnnnnnnn nnnnnnnnnn | 8820 |
| nnnnnnnnnn nnnnnnnnnn nnnnnnnnnn nnnnnnnnnn nnnnnnnnnn nnnnnnnnnn | 8880 |
| nnnnnnnnnn nnnnnnnnnn nnnnnnnnnn nnnnnnnnnn nnnnnnnnnn nnnnnnnnnn | 8940 |
| nnnnnnnnnn nnnnnnnnnn nnnnnnnnnn nnnnnnnnnn nnnnnnnnnn nnnnnnnnnn | 9000 |
| nnnnnnnnnn nnnnnnnnnn nnnnnnnnnn nnnnnnnnnn nnnnnnnnnn nnnnnnnnnn | 9060 |
| nnnnnnnnnn nnnnnnnnnn nnnnnnnnnn nnnnnnnnnn nnnnnnnnnn nnnnnnnnnn | 9120 |
| nnnnnnnnnn nnnnnnnnnn nnnnnnnnnn nnnnnnnnnn nnnnnnnnnn nnnnnnnnnn | 9180 |
| nnnnnnnnnn nnnnnnnnnn nnnnnnnnnn nnnnnnnnnn nnnnnnnnnn nnnnnnnnnn | 9240 |
| nnnnnnnnnn nnnnnnnnnn nnnnnnnnnn nnnnnnnnnn nnnnnnnnnn nnnnnnnnnn | 9300 |
| nnnnnnnnnn nnnnnnnnnn nnnnnnnnnn nnnnnnnnnn nnnnnnnnnn nnnnnnnnnn | 9360 |
| nnnnnnnnnn nnnnnnnnnn nnnnnnnnnn nnnnnnnnnn nnnnnnnnnn nnnnnnnnnn | 9420 |
| nnnnnnnnnn nnnnnnnnnn nnnnnnnnnn nnnnnnnnnn nnnnnnnnnn nnnnnnnnnn | 9480 |
| nnnnnnnnnn nnnnnnnnnn nnnnnnnnnn nnnnnnnnnn nnnnnnnnnn nnnnnnnnnn | 9540 |
| nnnnnnnnnn nnnnnnnnnn nnnnnnnnnn nnnnnnnnnn nnnnnnnnnn nnnnnnnnnn | 9600 |
| nnnnnnnnnn nnnnnnnnnn nnnnnnnnnn nnnnnnnnnn nnnnnnnnnn nnnnnnnnnn | 9660 |
| nnnnnnnnnn nnnnnnnnnn nnnnnnnnnn nnnnnnnnnn nnnnnnnnnn nnnnnnnnnn | 9720 |
| nnnnnnnnnn nnnnnnnnnn nnnnnnnnnn nnnnnnnnnn nnnnnnnnnn nnnnnnnnnn | 9780 |
| nnnnnnnnnn nnnnnnnnnn nnnnnnnnnn nnnnnnnnnn nnnnnnnnnn nnnnnnnnnn | 9840 |
| nnnnnnnnnn nnnnnnnnnn nnnnnnnnnn nnnnnnnnnn nnnnnnnnnn nnnnnnnnnn | 9900 |
| nnnnnnnnnn nnnnnnnnnn nnnnnnnnnn nnnnnnnnnn nnnnnnnnnn nnnnnnnnnn | 9960 |
| nnnnnnnnnn nnnnnnnnnn nnnnnnnnnn nnnnnnnnnn nnnnnnnnnn nnnnnnnnnn | 10020 |
| nnngtcggag cggccgctaa tt | 10042 |

```
<210> SEQ ID NO 26
<211> LENGTH: 10020
<212> TYPE: DNA
<213> ORGANISM: Artificial Sequence
<220> FEATURE:
<223> OTHER INFORMATION: Description of Artificial Sequence: Synthetic
      top strand polynucleotide cloned fragment
<220> FEATURE:
<221> NAME/KEY: modified_base
<222> LOCATION: (13)..(10012)
<223> OTHER INFORMATION: a, c, t or g

<400> SEQUENCE: 26
ggccgctccg acnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnnnnnnn nnnnnnnnnn nnnnnnnnnn     420
nnnnnnnnnn nnnnnnnnnn nnnnnnnnnn nnnnnnnnnn nnnnnnnnnn nnnnnnnnnn     480
nnnnnnnnnn nnnnnnnnnn nnnnnnnnnn nnnnnnnnnn nnnnnnnnnn nnnnnnnnnn     540
nnnnnnnnnn nnnnnnnnnn nnnnnnnnnn nnnnnnnnnn nnnnnnnnnn nnnnnnnnnn     600
nnnnnnnnnn nnnnnnnnnn nnnnnnnnnn nnnnnnnnnn nnnnnnnnnn nnnnnnnnnn     660
nnnnnnnnnn nnnnnnnnnn nnnnnnnnnn nnnnnnnnnn nnnnnnnnnn nnnnnnnnnn     720
nnnnnnnnnn nnnnnnnnnn nnnnnnnnnn nnnnnnnnnn nnnnnnnnnn nnnnnnnnnn     780
nnnnnnnnnn nnnnnnnnnn nnnnnnnnnn nnnnnnnnnn nnnnnnnnnn nnnnnnnnnn     840
nnnnnnnnnn nnnnnnnnnn nnnnnnnnnn nnnnnnnnnn nnnnnnnnnn nnnnnnnnnn     900
nnnnnnnnnn nnnnnnnnnn nnnnnnnnnn nnnnnnnnnn nnnnnnnnnn nnnnnnnnnn     960
nnnnnnnnnn nnnnnnnnnn nnnnnnnnnn nnnnnnnnnn nnnnnnnnnn nnnnnnnnnn    1020
nnnnnnnnnn nnnnnnnnnn nnnnnnnnnn nnnnnnnnnn nnnnnnnnnn nnnnnnnnnn    1080
nnnnnnnnnn nnnnnnnnnn nnnnnnnnnn nnnnnnnnnn nnnnnnnnnn nnnnnnnnnn    1140
nnnnnnnnnn nnnnnnnnnn nnnnnnnnnn nnnnnnnnnn nnnnnnnnnn nnnnnnnnnn    1200
nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnnn    1500
nnnnnnnnnn nnnnnnnnnn nnnnnnnnnn nnnnnnnnnn nnnnnnnnnn nnnnnnnnnn    1560
nnnnnnnnnn nnnnnnnnnn nnnnnnnnnn nnnnnnnnnn nnnnnnnnnn nnnnnnnnnn    1620
nnnnnnnnnn nnnnnnnnnn nnnnnnnnnn nnnnnnnnnn nnnnnnnnnn nnnnnnnnnn    1680
nnnnnnnnnn nnnnnnnnnn nnnnnnnnnn nnnnnnnnnn nnnnnnnnnn nnnnnnnnnn    1740
nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
nnnnnnnnnn nnnnnnnnnn nnnnnnnnnn nnnnnnnnnn nnnnnnnnnn nnnnnnnnnn    1980
```

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 2040 |
| nnnnnnnnnn | nnnnnnnnnn | nnnnnnnnnn | nnnnnnnnnn | nnnnnnnnnn | nnnnnnnnnn | 2100 |
| nnnnnnnnnn | nnnnnnnnnn | nnnnnnnnnn | nnnnnnnnnn | nnnnnnnnnn | nnnnnnnnnn | 2160 |
| nnnnnnnnnn | nnnnnnnnnn | nnnnnnnnnn | nnnnnnnnnn | nnnnnnnnnn | nnnnnnnnnn | 2220 |
| nnnnnnnnnn | nnnnnnnnnn | nnnnnnnnnn | nnnnnnnnnn | nnnnnnnnnn | nnnnnnnnnn | 2280 |
| nnnnnnnnnn | nnnnnnnnnn | nnnnnnnnnn | nnnnnnnnnn | nnnnnnnnnn | nnnnnnnnnn | 2340 |
| nnnnnnnnnn | nnnnnnnnnn | nnnnnnnnnn | nnnnnnnnnn | nnnnnnnnnn | nnnnnnnnnn | 2400 |
| nnnnnnnnnn | nnnnnnnnnn | nnnnnnnnnn | nnnnnnnnnn | nnnnnnnnnn | nnnnnnnnnn | 2460 |
| nnnnnnnnnn | nnnnnnnnnn | nnnnnnnnnn | nnnnnnnnnn | nnnnnnnnnn | nnnnnnnnnn | 2520 |
| nnnnnnnnnn | nnnnnnnnnn | nnnnnnnnnn | nnnnnnnnnn | nnnnnnnnnn | nnnnnnnnnn | 2580 |
| nnnnnnnnnn | nnnnnnnnnn | nnnnnnnnnn | nnnnnnnnnn | nnnnnnnnnn | nnnnnnnnnn | 2640 |
| nnnnnnnnnn | nnnnnnnnnn | nnnnnnnnnn | nnnnnnnnnn | nnnnnnnnnn | nnnnnnnnnn | 2700 |
| nnnnnnnnnn | nnnnnnnnnn | nnnnnnnnnn | nnnnnnnnnn | nnnnnnnnnn | nnnnnnnnnn | 2760 |
| nnnnnnnnnn | nnnnnnnnnn | nnnnnnnnnn | nnnnnnnnnn | nnnnnnnnnn | nnnnnnnnnn | 2820 |
| nnnnnnnnnn | nnnnnnnnnn | nnnnnnnnnn | nnnnnnnnnn | nnnnnnnnnn | nnnnnnnnnn | 2880 |
| nnnnnnnnnn | nnnnnnnnnn | nnnnnnnnnn | nnnnnnnnnn | nnnnnnnnnn | nnnnnnnnnn | 2940 |
| nnnnnnnnnn | nnnnnnnnnn | nnnnnnnnnn | nnnnnnnnnn | nnnnnnnnnn | nnnnnnnnnn | 3000 |
| nnnnnnnnnn | nnnnnnnnnn | nnnnnnnnnn | nnnnnnnnnn | nnnnnnnnnn | nnnnnnnnnn | 3060 |
| nnnnnnnnnn | nnnnnnnnnn | nnnnnnnnnn | nnnnnnnnnn | nnnnnnnnnn | nnnnnnnnnn | 3120 |
| nnnnnnnnnn | nnnnnnnnnn | nnnnnnnnnn | nnnnnnnnnn | nnnnnnnnnn | nnnnnnnnnn | 3180 |
| nnnnnnnnnn | nnnnnnnnnn | nnnnnnnnnn | nnnnnnnnnn | nnnnnnnnnn | nnnnnnnnnn | 3240 |
| nnnnnnnnnn | nnnnnnnnnn | nnnnnnnnnn | nnnnnnnnnn | nnnnnnnnnn | nnnnnnnnnn | 3300 |
| nnnnnnnnnn | nnnnnnnnnn | nnnnnnnnnn | nnnnnnnnnn | nnnnnnnnnn | nnnnnnnnnn | 3360 |
| nnnnnnnnnn | nnnnnnnnnn | nnnnnnnnnn | nnnnnnnnnn | nnnnnnnnnn | nnnnnnnnnn | 3420 |
| nnnnnnnnnn | nnnnnnnnnn | nnnnnnnnnn | nnnnnnnnnn | nnnnnnnnnn | nnnnnnnnnn | 3480 |
| nnnnnnnnnn | nnnnnnnnnn | nnnnnnnnnn | nnnnnnnnnn | nnnnnnnnnn | nnnnnnnnnn | 3540 |
| nnnnnnnnnn | nnnnnnnnnn | nnnnnnnnnn | nnnnnnnnnn | nnnnnnnnnn | nnnnnnnnnn | 3600 |
| nnnnnnnnnn | nnnnnnnnnn | nnnnnnnnnn | nnnnnnnnnn | nnnnnnnnnn | nnnnnnnnnn | 3660 |
| nnnnnnnnnn | nnnnnnnnnn | nnnnnnnnnn | nnnnnnnnnn | nnnnnnnnnn | nnnnnnnnnn | 3720 |
| nnnnnnnnnn | nnnnnnnnnn | nnnnnnnnnn | nnnnnnnnnn | nnnnnnnnnn | nnnnnnnnnn | 3780 |
| nnnnnnnnnn | nnnnnnnnnn | nnnnnnnnnn | nnnnnnnnnn | nnnnnnnnnn | nnnnnnnnnn | 3840 |
| nnnnnnnnnn | nnnnnnnnnn | nnnnnnnnnn | nnnnnnnnnn | nnnnnnnnnn | nnnnnnnnnn | 3900 |
| nnnnnnnnnn | nnnnnnnnnn | nnnnnnnnnn | nnnnnnnnnn | nnnnnnnnnn | nnnnnnnnnn | 3960 |
| nnnnnnnnnn | nnnnnnnnnn | nnnnnnnnnn | nnnnnnnnnn | nnnnnnnnnn | nnnnnnnnnn | 4020 |
| nnnnnnnnnn | nnnnnnnnnn | nnnnnnnnnn | nnnnnnnnnn | nnnnnnnnnn | nnnnnnnnnn | 4080 |
| nnnnnnnnnn | nnnnnnnnnn | nnnnnnnnnn | nnnnnnnnnn | nnnnnnnnnn | nnnnnnnnnn | 4140 |
| nnnnnnnnnn | nnnnnnnnnn | nnnnnnnnnn | nnnnnnnnnn | nnnnnnnnnn | nnnnnnnnnn | 4200 |
| nnnnnnnnnn | nnnnnnnnnn | nnnnnnnnnn | nnnnnnnnnn | nnnnnnnnnn | nnnnnnnnnn | 4260 |
| nnnnnnnnnn | nnnnnnnnnn | nnnnnnnnnn | nnnnnnnnnn | nnnnnnnnnn | nnnnnnnnnn | 4320 |

```
nnnnnnnnnn nnnnnnnnnn nnnnnnnnnn nnnnnnnnnn nnnnnnnnnn nnnnnnnnnn    4380
nnnnnnnnnn nnnnnnnnnn nnnnnnnnnn nnnnnnnnnn nnnnnnnnnn nnnnnnnnnn    4440
nnnnnnnnnn nnnnnnnnnn nnnnnnnnnn nnnnnnnnnn nnnnnnnnnn nnnnnnnnnn    4500
nnnnnnnnnn nnnnnnnnnn nnnnnnnnnn nnnnnnnnnn nnnnnnnnnn nnnnnnnnnn    4560
nnnnnnnnnn nnnnnnnnnn nnnnnnnnnn nnnnnnnnnn nnnnnnnnnn nnnnnnnnnn    4620
nnnnnnnnnn nnnnnnnnnn nnnnnnnnnn nnnnnnnnnn nnnnnnnnnn nnnnnnnnnn    4680
nnnnnnnnnn nnnnnnnnnn nnnnnnnnnn nnnnnnnnnn nnnnnnnnnn nnnnnnnnnn    4740
nnnnnnnnnn nnnnnnnnnn nnnnnnnnnn nnnnnnnnnn nnnnnnnnnn nnnnnnnnnn    4800
nnnnnnnnnn nnnnnnnnnn nnnnnnnnnn nnnnnnnnnn nnnnnnnnnn nnnnnnnnnn    4860
nnnnnnnnnn nnnnnnnnnn nnnnnnnnnn nnnnnnnnnn nnnnnnnnnn nnnnnnnnnn    4920
nnnnnnnnnn nnnnnnnnnn nnnnnnnnnn nnnnnnnnnn nnnnnnnnnn nnnnnnnnnn    4980
nnnnnnnnnn nnnnnnnnnn nnnnnnnnnn nnnnnnnnnn nnnnnnnnnn nnnnnnnnnn    5040
nnnnnnnnnn nnnnnnnnnn nnnnnnnnnn nnnnnnnnnn nnnnnnnnnn nnnnnnnnnn    5100
nnnnnnnnnn nnnnnnnnnn nnnnnnnnnn nnnnnnnnnn nnnnnnnnnn nnnnnnnnnn    5160
nnnnnnnnnn nnnnnnnnnn nnnnnnnnnn nnnnnnnnnn nnnnnnnnnn nnnnnnnnnn    5220
nnnnnnnnnn nnnnnnnnnn nnnnnnnnnn nnnnnnnnnn nnnnnnnnnn nnnnnnnnnn    5280
nnnnnnnnnn nnnnnnnnnn nnnnnnnnnn nnnnnnnnnn nnnnnnnnnn nnnnnnnnnn    5340
nnnnnnnnnn nnnnnnnnnn nnnnnnnnnn nnnnnnnnnn nnnnnnnnnn nnnnnnnnnn    5400
nnnnnnnnnn nnnnnnnnnn nnnnnnnnnn nnnnnnnnnn nnnnnnnnnn nnnnnnnnnn    5460
nnnnnnnnnn nnnnnnnnnn nnnnnnnnnn nnnnnnnnnn nnnnnnnnnn nnnnnnnnnn    5520
nnnnnnnnnn nnnnnnnnnn nnnnnnnnnn nnnnnnnnnn nnnnnnnnnn nnnnnnnnnn    5580
nnnnnnnnnn nnnnnnnnnn nnnnnnnnnn nnnnnnnnnn nnnnnnnnnn nnnnnnnnnn    5640
nnnnnnnnnn nnnnnnnnnn nnnnnnnnnn nnnnnnnnnn nnnnnnnnnn nnnnnnnnnn    5700
nnnnnnnnnn nnnnnnnnnn nnnnnnnnnn nnnnnnnnnn nnnnnnnnnn nnnnnnnnnn    5760
nnnnnnnnnn nnnnnnnnnn nnnnnnnnnn nnnnnnnnnn nnnnnnnnnn nnnnnnnnnn    5820
nnnnnnnnnn nnnnnnnnnn nnnnnnnnnn nnnnnnnnnn nnnnnnnnnn nnnnnnnnnn    5880
nnnnnnnnnn nnnnnnnnnn nnnnnnnnnn nnnnnnnnnn nnnnnnnnnn nnnnnnnnnn    5940
nnnnnnnnnn nnnnnnnnnn nnnnnnnnnn nnnnnnnnnn nnnnnnnnnn nnnnnnnnnn    6000
nnnnnnnnnn nnnnnnnnnn nnnnnnnnnn nnnnnnnnnn nnnnnnnnnn nnnnnnnnnn    6060
nnnnnnnnnn nnnnnnnnnn nnnnnnnnnn nnnnnnnnnn nnnnnnnnnn nnnnnnnnnn    6120
nnnnnnnnnn nnnnnnnnnn nnnnnnnnnn nnnnnnnnnn nnnnnnnnnn nnnnnnnnnn    6180
nnnnnnnnnn nnnnnnnnnn nnnnnnnnnn nnnnnnnnnn nnnnnnnnnn nnnnnnnnnn    6240
nnnnnnnnnn nnnnnnnnnn nnnnnnnnnn nnnnnnnnnn nnnnnnnnnn nnnnnnnnnn    6300
nnnnnnnnnn nnnnnnnnnn nnnnnnnnnn nnnnnnnnnn nnnnnnnnnn nnnnnnnnnn    6360
nnnnnnnnnn nnnnnnnnnn nnnnnnnnnn nnnnnnnnnn nnnnnnnnnn nnnnnnnnnn    6420
nnnnnnnnnn nnnnnnnnnn nnnnnnnnnn nnnnnnnnnn nnnnnnnnnn nnnnnnnnnn    6480
nnnnnnnnnn nnnnnnnnnn nnnnnnnnnn nnnnnnnnnn nnnnnnnnnn nnnnnnnnnn    6540
nnnnnnnnnn nnnnnnnnnn nnnnnnnnnn nnnnnnnnnn nnnnnnnnnn nnnnnnnnnn    6600
nnnnnnnnnn nnnnnnnnnn nnnnnnnnnn nnnnnnnnnn nnnnnnnnnn nnnnnnnnnn    6660
nnnnnnnnnn nnnnnnnnnn nnnnnnnnnn nnnnnnnnnn nnnnnnnnnn nnnnnnnnnn    6720
```

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 6780 |
| nnnnnnnnnn | nnnnnnnnnn | nnnnnnnnnn | nnnnnnnnnn | nnnnnnnnnn | nnnnnnnnnn | 6840 |
| nnnnnnnnnn | nnnnnnnnnn | nnnnnnnnnn | nnnnnnnnnn | nnnnnnnnnn | nnnnnnnnnn | 6900 |
| nnnnnnnnnn | nnnnnnnnnn | nnnnnnnnnn | nnnnnnnnnn | nnnnnnnnnn | nnnnnnnnnn | 6960 |
| nnnnnnnnnn | nnnnnnnnnn | nnnnnnnnnn | nnnnnnnnnn | nnnnnnnnnn | nnnnnnnnnn | 7020 |
| nnnnnnnnnn | nnnnnnnnnn | nnnnnnnnnn | nnnnnnnnnn | nnnnnnnnnn | nnnnnnnnnn | 7080 |
| nnnnnnnnnn | nnnnnnnnnn | nnnnnnnnnn | nnnnnnnnnn | nnnnnnnnnn | nnnnnnnnnn | 7140 |
| nnnnnnnnnn | nnnnnnnnnn | nnnnnnnnnn | nnnnnnnnnn | nnnnnnnnnn | nnnnnnnnnn | 7200 |
| nnnnnnnnnn | nnnnnnnnnn | nnnnnnnnnn | nnnnnnnnnn | nnnnnnnnnn | nnnnnnnnnn | 7260 |
| nnnnnnnnnn | nnnnnnnnnn | nnnnnnnnnn | nnnnnnnnnn | nnnnnnnnnn | nnnnnnnnnn | 7320 |
| nnnnnnnnnn | nnnnnnnnnn | nnnnnnnnnn | nnnnnnnnnn | nnnnnnnnnn | nnnnnnnnnn | 7380 |
| nnnnnnnnnn | nnnnnnnnnn | nnnnnnnnnn | nnnnnnnnnn | nnnnnnnnnn | nnnnnnnnnn | 7440 |
| nnnnnnnnnn | nnnnnnnnnn | nnnnnnnnnn | nnnnnnnnnn | nnnnnnnnnn | nnnnnnnnnn | 7500 |
| nnnnnnnnnn | nnnnnnnnnn | nnnnnnnnnn | nnnnnnnnnn | nnnnnnnnnn | nnnnnnnnnn | 7560 |
| nnnnnnnnnn | nnnnnnnnnn | nnnnnnnnnn | nnnnnnnnnn | nnnnnnnnnn | nnnnnnnnnn | 7620 |
| nnnnnnnnnn | nnnnnnnnnn | nnnnnnnnnn | nnnnnnnnnn | nnnnnnnnnn | nnnnnnnnnn | 7680 |
| nnnnnnnnnn | nnnnnnnnnn | nnnnnnnnnn | nnnnnnnnnn | nnnnnnnnnn | nnnnnnnnnn | 7740 |
| nnnnnnnnnn | nnnnnnnnnn | nnnnnnnnnn | nnnnnnnnnn | nnnnnnnnnn | nnnnnnnnnn | 7800 |
| nnnnnnnnnn | nnnnnnnnnn | nnnnnnnnnn | nnnnnnnnnn | nnnnnnnnnn | nnnnnnnnnn | 7860 |
| nnnnnnnnnn | nnnnnnnnnn | nnnnnnnnnn | nnnnnnnnnn | nnnnnnnnnn | nnnnnnnnnn | 7920 |
| nnnnnnnnnn | nnnnnnnnnn | nnnnnnnnnn | nnnnnnnnnn | nnnnnnnnnn | nnnnnnnnnn | 7980 |
| nnnnnnnnnn | nnnnnnnnnn | nnnnnnnnnn | nnnnnnnnnn | nnnnnnnnnn | nnnnnnnnnn | 8040 |
| nnnnnnnnnn | nnnnnnnnnn | nnnnnnnnnn | nnnnnnnnnn | nnnnnnnnnn | nnnnnnnnnn | 8100 |
| nnnnnnnnnn | nnnnnnnnnn | nnnnnnnnnn | nnnnnnnnnn | nnnnnnnnnn | nnnnnnnnnn | 8160 |
| nnnnnnnnnn | nnnnnnnnnn | nnnnnnnnnn | nnnnnnnnnn | nnnnnnnnnn | nnnnnnnnnn | 8220 |
| nnnnnnnnnn | nnnnnnnnnn | nnnnnnnnnn | nnnnnnnnnn | nnnnnnnnnn | nnnnnnnnnn | 8280 |
| nnnnnnnnnn | nnnnnnnnnn | nnnnnnnnnn | nnnnnnnnnn | nnnnnnnnnn | nnnnnnnnnn | 8340 |
| nnnnnnnnnn | nnnnnnnnnn | nnnnnnnnnn | nnnnnnnnnn | nnnnnnnnnn | nnnnnnnnnn | 8400 |
| nnnnnnnnnn | nnnnnnnnnn | nnnnnnnnnn | nnnnnnnnnn | nnnnnnnnnn | nnnnnnnnnn | 8460 |
| nnnnnnnnnn | nnnnnnnnnn | nnnnnnnnnn | nnnnnnnnnn | nnnnnnnnnn | nnnnnnnnnn | 8520 |
| nnnnnnnnnn | nnnnnnnnnn | nnnnnnnnnn | nnnnnnnnnn | nnnnnnnnnn | nnnnnnnnnn | 8580 |
| nnnnnnnnnn | nnnnnnnnnn | nnnnnnnnnn | nnnnnnnnnn | nnnnnnnnnn | nnnnnnnnnn | 8640 |
| nnnnnnnnnn | nnnnnnnnnn | nnnnnnnnnn | nnnnnnnnnn | nnnnnnnnnn | nnnnnnnnnn | 8700 |
| nnnnnnnnnn | nnnnnnnnnn | nnnnnnnnnn | nnnnnnnnnn | nnnnnnnnnn | nnnnnnnnnn | 8760 |
| nnnnnnnnnn | nnnnnnnnnn | nnnnnnnnnn | nnnnnnnnnn | nnnnnnnnnn | nnnnnnnnnn | 8820 |
| nnnnnnnnnn | nnnnnnnnnn | nnnnnnnnnn | nnnnnnnnnn | nnnnnnnnnn | nnnnnnnnnn | 8880 |
| nnnnnnnnnn | nnnnnnnnnn | nnnnnnnnnn | nnnnnnnnnn | nnnnnnnnnn | nnnnnnnnnn | 8940 |
| nnnnnnnnnn | nnnnnnnnnn | nnnnnnnnnn | nnnnnnnnnn | nnnnnnnnnn | nnnnnnnnnn | 9000 |
| nnnnnnnnnn | nnnnnnnnnn | nnnnnnnnnn | nnnnnnnnnn | nnnnnnnnnn | nnnnnnnnnn | 9060 |

| | | |
|---|---|---|
| nnnnnnnnnn nnnnnnnnnn nnnnnnnnnn nnnnnnnnnn nnnnnnnnnn nnnnnnnnnn | 9120 | |
| nnnnnnnnnn nnnnnnnnnn nnnnnnnnnn nnnnnnnnnn nnnnnnnnnn nnnnnnnnnn | 9180 | |
| nnnnnnnnnn nnnnnnnnnn nnnnnnnnnn nnnnnnnnnn nnnnnnnnnn nnnnnnnnnn | 9240 | |
| nnnnnnnnnn nnnnnnnnnn nnnnnnnnnn nnnnnnnnnn nnnnnnnnnn nnnnnnnnnn | 9300 | |
| nnnnnnnnnn nnnnnnnnnn nnnnnnnnnn nnnnnnnnnn nnnnnnnnnn nnnnnnnnnn | 9360 | |
| nnnnnnnnnn nnnnnnnnnn nnnnnnnnnn nnnnnnnnnn nnnnnnnnnn nnnnnnnnnn | 9420 | |
| nnnnnnnnnn nnnnnnnnnn nnnnnnnnnn nnnnnnnnnn nnnnnnnnnn nnnnnnnnnn | 9480 | |
| nnnnnnnnnn nnnnnnnnnn nnnnnnnnnn nnnnnnnnnn nnnnnnnnnn nnnnnnnnnn | 9540 | |
| nnnnnnnnnn nnnnnnnnnn nnnnnnnnnn nnnnnnnnnn nnnnnnnnnn nnnnnnnnnn | 9600 | |
| nnnnnnnnnn nnnnnnnnnn nnnnnnnnnn nnnnnnnnnn nnnnnnnnnn nnnnnnnnnn | 9660 | |
| nnnnnnnnnn nnnnnnnnnn nnnnnnnnnn nnnnnnnnnn nnnnnnnnnn nnnnnnnnnn | 9720 | |
| nnnnnnnnnn nnnnnnnnnn nnnnnnnnnn nnnnnnnnnn nnnnnnnnnn nnnnnnnnnn | 9780 | |
| nnnnnnnnnn nnnnnnnnnn nnnnnnnnnn nnnnnnnnnn nnnnnnnnnn nnnnnnnnnn | 9840 | |
| nnnnnnnnnn nnnnnnnnnn nnnnnnnnnn nnnnnnnnnn nnnnnnnnnn nnnnnnnnnn | 9900 | |
| nnnnnnnnnn nnnnnnnnnn nnnnnnnnnn nnnnnnnnnn nnnnnnnnnn nnnnnnnnnn | 9960 | |
| nnnnnnnnnn nnnnnnnnnn nnnnnnnnnn nnnnnnnnnn nnnnnnnnnn nngtcggagc | 10020 | |

<210> SEQ ID NO 27
<211> LENGTH: 10020
<212> TYPE: DNA
<213> ORGANISM: Artificial Sequence
<220> FEATURE:
<223> OTHER INFORMATION: Description of Artificial Sequence: Synthetic
      bottom strand polynucleotide cloned fragment
<220> FEATURE:
<221> NAME/KEY: modified_base
<222> LOCATION: (13)..(10012)
<223> OTHER INFORMATION: a, c, t or g

<400> SEQUENCE: 27

| | | |
|---|---|---|
| ggccgctccg acnnnnnnnn nnnnnnnnnn nnnnnnnnnn nnnnnnnnnn nnnnnnnnnn | 60 | |
| nnnnnnnnnn nnnnnnnnnn nnnnnnnnnn nnnnnnnnnn nnnnnnnnnn nnnnnnnnnn | 120 | |
| nnnnnnnnnn nnnnnnnnnn nnnnnnnnnn nnnnnnnnnn nnnnnnnnnn nnnnnnnnnn | 180 | |
| nnnnnnnnnn nnnnnnnnnn nnnnnnnnnn nnnnnnnnnn nnnnnnnnnn nnnnnnnnnn | 240 | |
| nnnnnnnnnn nnnnnnnnnn nnnnnnnnnn nnnnnnnnnn nnnnnnnnnn nnnnnnnnnn | 300 | |
| nnnnnnnnnn nnnnnnnnnn nnnnnnnnnn nnnnnnnnnn nnnnnnnnnn nnnnnnnnnn | 360 | |
| nnnnnnnnnn nnnnnnnnnn nnnnnnnnnn nnnnnnnnnn nnnnnnnnnn nnnnnnnnnn | 420 | |
| nnnnnnnnnn nnnnnnnnnn nnnnnnnnnn nnnnnnnnnn nnnnnnnnnn nnnnnnnnnn | 480 | |
| nnnnnnnnnn nnnnnnnnnn nnnnnnnnnn nnnnnnnnnn nnnnnnnnnn nnnnnnnnnn | 540 | |
| nnnnnnnnnn nnnnnnnnnn nnnnnnnnnn nnnnnnnnnn nnnnnnnnnn nnnnnnnnnn | 600 | |
| nnnnnnnnnn nnnnnnnnnn nnnnnnnnnn nnnnnnnnnn nnnnnnnnnn nnnnnnnnnn | 660 | |
| nnnnnnnnnn nnnnnnnnnn nnnnnnnnnn nnnnnnnnnn nnnnnnnnnn nnnnnnnnnn | 720 | |
| nnnnnnnnnn nnnnnnnnnn nnnnnnnnnn nnnnnnnnnn nnnnnnnnnn nnnnnnnnnn | 780 | |
| nnnnnnnnnn nnnnnnnnnn nnnnnnnnnn nnnnnnnnnn nnnnnnnnnn nnnnnnnnnn | 840 | |
| nnnnnnnnnn nnnnnnnnnn nnnnnnnnnn nnnnnnnnnn nnnnnnnnnn nnnnnnnnnn | 900 | |
| nnnnnnnnnn nnnnnnnnnn nnnnnnnnnn nnnnnnnnnn nnnnnnnnnn nnnnnnnnnn | 960 | |

| | |
|---|---|
| nnnnnnnnnn nnnnnnnnnn nnnnnnnnnn nnnnnnnnnn nnnnnnnnnn nnnnnnnnnn | 1020 |
| nnnnnnnnnn nnnnnnnnnn nnnnnnnnnn nnnnnnnnnn nnnnnnnnnn nnnnnnnnnn | 1080 |
| nnnnnnnnnn nnnnnnnnnn nnnnnnnnnn nnnnnnnnnn nnnnnnnnnn nnnnnnnnnn | 1140 |
| nnnnnnnnnn nnnnnnnnnn nnnnnnnnnn nnnnnnnnnn nnnnnnnnnn nnnnnnnnnn | 1200 |
| nnnnnnnnnn nnnnnnnnnn nnnnnnnnnn nnnnnnnnnn nnnnnnnnnn nnnnnnnnnn | 1260 |
| nnnnnnnnnn nnnnnnnnnn nnnnnnnnnn nnnnnnnnnn nnnnnnnnnn nnnnnnnnnn | 1320 |
| nnnnnnnnnn nnnnnnnnnn nnnnnnnnnn nnnnnnnnnn nnnnnnnnnn nnnnnnnnnn | 1380 |
| nnnnnnnnnn nnnnnnnnnn nnnnnnnnnn nnnnnnnnnn nnnnnnnnnn nnnnnnnnnn | 1440 |
| nnnnnnnnnn nnnnnnnnnn nnnnnnnnnn nnnnnnnnnn nnnnnnnnnn nnnnnnnnnn | 1500 |
| nnnnnnnnnn nnnnnnnnnn nnnnnnnnnn nnnnnnnnnn nnnnnnnnnn nnnnnnnnnn | 1560 |
| nnnnnnnnnn nnnnnnnnnn nnnnnnnnnn nnnnnnnnnn nnnnnnnnnn nnnnnnnnnn | 1620 |
| nnnnnnnnnn nnnnnnnnnn nnnnnnnnnn nnnnnnnnnn nnnnnnnnnn nnnnnnnnnn | 1680 |
| nnnnnnnnnn nnnnnnnnnn nnnnnnnnnn nnnnnnnnnn nnnnnnnnnn nnnnnnnnnn | 1740 |
| nnnnnnnnnn nnnnnnnnnn nnnnnnnnnn nnnnnnnnnn nnnnnnnnnn nnnnnnnnnn | 1800 |
| nnnnnnnnnn nnnnnnnnnn nnnnnnnnnn nnnnnnnnnn nnnnnnnnnn nnnnnnnnnn | 1860 |
| nnnnnnnnnn nnnnnnnnnn nnnnnnnnnn nnnnnnnnnn nnnnnnnnnn nnnnnnnnnn | 1920 |
| nnnnnnnnnn nnnnnnnnnn nnnnnnnnnn nnnnnnnnnn nnnnnnnnnn nnnnnnnnnn | 1980 |
| nnnnnnnnnn nnnnnnnnnn nnnnnnnnnn nnnnnnnnnn nnnnnnnnnn nnnnnnnnnn | 2040 |
| nnnnnnnnnn nnnnnnnnnn nnnnnnnnnn nnnnnnnnnn nnnnnnnnnn nnnnnnnnnn | 2100 |
| nnnnnnnnnn nnnnnnnnnn nnnnnnnnnn nnnnnnnnnn nnnnnnnnnn nnnnnnnnnn | 2160 |
| nnnnnnnnnn nnnnnnnnnn nnnnnnnnnn nnnnnnnnnn nnnnnnnnnn nnnnnnnnnn | 2220 |
| nnnnnnnnnn nnnnnnnnnn nnnnnnnnnn nnnnnnnnnn nnnnnnnnnn nnnnnnnnnn | 2280 |
| nnnnnnnnnn nnnnnnnnnn nnnnnnnnnn nnnnnnnnnn nnnnnnnnnn nnnnnnnnnn | 2340 |
| nnnnnnnnnn nnnnnnnnnn nnnnnnnnnn nnnnnnnnnn nnnnnnnnnn nnnnnnnnnn | 2400 |
| nnnnnnnnnn nnnnnnnnnn nnnnnnnnnn nnnnnnnnnn nnnnnnnnnn nnnnnnnnnn | 2460 |
| nnnnnnnnnn nnnnnnnnnn nnnnnnnnnn nnnnnnnnnn nnnnnnnnnn nnnnnnnnnn | 2520 |
| nnnnnnnnnn nnnnnnnnnn nnnnnnnnnn nnnnnnnnnn nnnnnnnnnn nnnnnnnnnn | 2580 |
| nnnnnnnnnn nnnnnnnnnn nnnnnnnnnn nnnnnnnnnn nnnnnnnnnn nnnnnnnnnn | 2640 |
| nnnnnnnnnn nnnnnnnnnn nnnnnnnnnn nnnnnnnnnn nnnnnnnnnn nnnnnnnnnn | 2700 |
| nnnnnnnnnn nnnnnnnnnn nnnnnnnnnn nnnnnnnnnn nnnnnnnnnn nnnnnnnnnn | 2760 |
| nnnnnnnnnn nnnnnnnnnn nnnnnnnnnn nnnnnnnnnn nnnnnnnnnn nnnnnnnnnn | 2820 |
| nnnnnnnnnn nnnnnnnnnn nnnnnnnnnn nnnnnnnnnn nnnnnnnnnn nnnnnnnnnn | 2880 |
| nnnnnnnnnn nnnnnnnnnn nnnnnnnnnn nnnnnnnnnn nnnnnnnnnn nnnnnnnnnn | 2940 |
| nnnnnnnnnn nnnnnnnnnn nnnnnnnnnn nnnnnnnnnn nnnnnnnnnn nnnnnnnnnn | 3000 |
| nnnnnnnnnn nnnnnnnnnn nnnnnnnnnn nnnnnnnnnn nnnnnnnnnn nnnnnnnnnn | 3060 |
| nnnnnnnnnn nnnnnnnnnn nnnnnnnnnn nnnnnnnnnn nnnnnnnnnn nnnnnnnnnn | 3120 |
| nnnnnnnnnn nnnnnnnnnn nnnnnnnnnn nnnnnnnnnn nnnnnnnnnn nnnnnnnnnn | 3180 |
| nnnnnnnnnn nnnnnnnnnn nnnnnnnnnn nnnnnnnnnn nnnnnnnnnn nnnnnnnnnn | 3240 |
| nnnnnnnnnn nnnnnnnnnn nnnnnnnnnn nnnnnnnnnn nnnnnnnnnn nnnnnnnnnn | 3300 |
| nnnnnnnnnn nnnnnnnnnn nnnnnnnnnn nnnnnnnnnn nnnnnnnnnn nnnnnnnnnn | 3360 |

| | |
|---|---|
| nnnnnnnnnn nnnnnnnnnn nnnnnnnnnn nnnnnnnnnn nnnnnnnnnn nnnnnnnnnn | 3420 |
| nnnnnnnnnn nnnnnnnnnn nnnnnnnnnn nnnnnnnnnn nnnnnnnnnn nnnnnnnnnn | 3480 |
| nnnnnnnnnn nnnnnnnnnn nnnnnnnnnn nnnnnnnnnn nnnnnnnnnn nnnnnnnnnn | 3540 |
| nnnnnnnnnn nnnnnnnnnn nnnnnnnnnn nnnnnnnnnn nnnnnnnnnn nnnnnnnnnn | 3600 |
| nnnnnnnnnn nnnnnnnnnn nnnnnnnnnn nnnnnnnnnn nnnnnnnnnn nnnnnnnnnn | 3660 |
| nnnnnnnnnn nnnnnnnnnn nnnnnnnnnn nnnnnnnnnn nnnnnnnnnn nnnnnnnnnn | 3720 |
| nnnnnnnnnn nnnnnnnnnn nnnnnnnnnn nnnnnnnnnn nnnnnnnnnn nnnnnnnnnn | 3780 |
| nnnnnnnnnn nnnnnnnnnn nnnnnnnnnn nnnnnnnnnn nnnnnnnnnn nnnnnnnnnn | 3840 |
| nnnnnnnnnn nnnnnnnnnn nnnnnnnnnn nnnnnnnnnn nnnnnnnnnn nnnnnnnnnn | 3900 |
| nnnnnnnnnn nnnnnnnnnn nnnnnnnnnn nnnnnnnnnn nnnnnnnnnn nnnnnnnnnn | 3960 |
| nnnnnnnnnn nnnnnnnnnn nnnnnnnnnn nnnnnnnnnn nnnnnnnnnn nnnnnnnnnn | 4020 |
| nnnnnnnnnn nnnnnnnnnn nnnnnnnnnn nnnnnnnnnn nnnnnnnnnn nnnnnnnnnn | 4080 |
| nnnnnnnnnn nnnnnnnnnn nnnnnnnnnn nnnnnnnnnn nnnnnnnnnn nnnnnnnnnn | 4140 |
| nnnnnnnnnn nnnnnnnnnn nnnnnnnnnn nnnnnnnnnn nnnnnnnnnn nnnnnnnnnn | 4200 |
| nnnnnnnnnn nnnnnnnnnn nnnnnnnnnn nnnnnnnnnn nnnnnnnnnn nnnnnnnnnn | 4260 |
| nnnnnnnnnn nnnnnnnnnn nnnnnnnnnn nnnnnnnnnn nnnnnnnnnn nnnnnnnnnn | 4320 |
| nnnnnnnnnn nnnnnnnnnn nnnnnnnnnn nnnnnnnnnn nnnnnnnnnn nnnnnnnnnn | 4380 |
| nnnnnnnnnn nnnnnnnnnn nnnnnnnnnn nnnnnnnnnn nnnnnnnnnn nnnnnnnnnn | 4440 |
| nnnnnnnnnn nnnnnnnnnn nnnnnnnnnn nnnnnnnnnn nnnnnnnnnn nnnnnnnnnn | 4500 |
| nnnnnnnnnn nnnnnnnnnn nnnnnnnnnn nnnnnnnnnn nnnnnnnnnn nnnnnnnnnn | 4560 |
| nnnnnnnnnn nnnnnnnnnn nnnnnnnnnn nnnnnnnnnn nnnnnnnnnn nnnnnnnnnn | 4620 |
| nnnnnnnnnn nnnnnnnnnn nnnnnnnnnn nnnnnnnnnn nnnnnnnnnn nnnnnnnnnn | 4680 |
| nnnnnnnnnn nnnnnnnnnn nnnnnnnnnn nnnnnnnnnn nnnnnnnnnn nnnnnnnnnn | 4740 |
| nnnnnnnnnn nnnnnnnnnn nnnnnnnnnn nnnnnnnnnn nnnnnnnnnn nnnnnnnnnn | 4800 |
| nnnnnnnnnn nnnnnnnnnn nnnnnnnnnn nnnnnnnnnn nnnnnnnnnn nnnnnnnnnn | 4860 |
| nnnnnnnnnn nnnnnnnnnn nnnnnnnnnn nnnnnnnnnn nnnnnnnnnn nnnnnnnnnn | 4920 |
| nnnnnnnnnn nnnnnnnnnn nnnnnnnnnn nnnnnnnnnn nnnnnnnnnn nnnnnnnnnn | 4980 |
| nnnnnnnnnn nnnnnnnnnn nnnnnnnnnn nnnnnnnnnn nnnnnnnnnn nnnnnnnnnn | 5040 |
| nnnnnnnnnn nnnnnnnnnn nnnnnnnnnn nnnnnnnnnn nnnnnnnnnn nnnnnnnnnn | 5100 |
| nnnnnnnnnn nnnnnnnnnn nnnnnnnnnn nnnnnnnnnn nnnnnnnnnn nnnnnnnnnn | 5160 |
| nnnnnnnnnn nnnnnnnnnn nnnnnnnnnn nnnnnnnnnn nnnnnnnnnn nnnnnnnnnn | 5220 |
| nnnnnnnnnn nnnnnnnnnn nnnnnnnnnn nnnnnnnnnn nnnnnnnnnn nnnnnnnnnn | 5280 |
| nnnnnnnnnn nnnnnnnnnn nnnnnnnnnn nnnnnnnnnn nnnnnnnnnn nnnnnnnnnn | 5340 |
| nnnnnnnnnn nnnnnnnnnn nnnnnnnnnn nnnnnnnnnn nnnnnnnnnn nnnnnnnnnn | 5400 |
| nnnnnnnnnn nnnnnnnnnn nnnnnnnnnn nnnnnnnnnn nnnnnnnnnn nnnnnnnnnn | 5460 |
| nnnnnnnnnn nnnnnnnnnn nnnnnnnnnn nnnnnnnnnn nnnnnnnnnn nnnnnnnnnn | 5520 |
| nnnnnnnnnn nnnnnnnnnn nnnnnnnnnn nnnnnnnnnn nnnnnnnnnn nnnnnnnnnn | 5580 |
| nnnnnnnnnn nnnnnnnnnn nnnnnnnnnn nnnnnnnnnn nnnnnnnnnn nnnnnnnnnn | 5640 |
| nnnnnnnnnn nnnnnnnnnn nnnnnnnnnn nnnnnnnnnn nnnnnnnnnn nnnnnnnnnn | 5700 |

| | | | | | | |
|---|---|---|---|---|---|---|
| nnnnnnnnnn | nnnnnnnnnn | nnnnnnnnnn | nnnnnnnnnn | nnnnnnnnnn | nnnnnnnnnn | 5760 |
| nnnnnnnnnn | nnnnnnnnnn | nnnnnnnnnn | nnnnnnnnnn | nnnnnnnnnn | nnnnnnnnnn | 5820 |
| nnnnnnnnnn | nnnnnnnnnn | nnnnnnnnnn | nnnnnnnnnn | nnnnnnnnnn | nnnnnnnnnn | 5880 |
| nnnnnnnnnn | nnnnnnnnnn | nnnnnnnnnn | nnnnnnnnnn | nnnnnnnnnn | nnnnnnnnnn | 5940 |
| nnnnnnnnnn | nnnnnnnnnn | nnnnnnnnnn | nnnnnnnnnn | nnnnnnnnnn | nnnnnnnnnn | 6000 |
| nnnnnnnnnn | nnnnnnnnnn | nnnnnnnnnn | nnnnnnnnnn | nnnnnnnnnn | nnnnnnnnnn | 6060 |
| nnnnnnnnnn | nnnnnnnnnn | nnnnnnnnnn | nnnnnnnnnn | nnnnnnnnnn | nnnnnnnnnn | 6120 |
| nnnnnnnnnn | nnnnnnnnnn | nnnnnnnnnn | nnnnnnnnnn | nnnnnnnnnn | nnnnnnnnnn | 6180 |
| nnnnnnnnnn | nnnnnnnnnn | nnnnnnnnnn | nnnnnnnnnn | nnnnnnnnnn | nnnnnnnnnn | 6240 |
| nnnnnnnnnn | nnnnnnnnnn | nnnnnnnnnn | nnnnnnnnnn | nnnnnnnnnn | nnnnnnnnnn | 6300 |
| nnnnnnnnnn | nnnnnnnnnn | nnnnnnnnnn | nnnnnnnnnn | nnnnnnnnnn | nnnnnnnnnn | 6360 |
| nnnnnnnnnn | nnnnnnnnnn | nnnnnnnnnn | nnnnnnnnnn | nnnnnnnnnn | nnnnnnnnnn | 6420 |
| nnnnnnnnnn | nnnnnnnnnn | nnnnnnnnnn | nnnnnnnnnn | nnnnnnnnnn | nnnnnnnnnn | 6480 |
| nnnnnnnnnn | nnnnnnnnnn | nnnnnnnnnn | nnnnnnnnnn | nnnnnnnnnn | nnnnnnnnnn | 6540 |
| nnnnnnnnnn | nnnnnnnnnn | nnnnnnnnnn | nnnnnnnnnn | nnnnnnnnnn | nnnnnnnnnn | 6600 |
| nnnnnnnnnn | nnnnnnnnnn | nnnnnnnnnn | nnnnnnnnnn | nnnnnnnnnn | nnnnnnnnnn | 6660 |
| nnnnnnnnnn | nnnnnnnnnn | nnnnnnnnnn | nnnnnnnnnn | nnnnnnnnnn | nnnnnnnnnn | 6720 |
| nnnnnnnnnn | nnnnnnnnnn | nnnnnnnnnn | nnnnnnnnnn | nnnnnnnnnn | nnnnnnnnnn | 6780 |
| nnnnnnnnnn | nnnnnnnnnn | nnnnnnnnnn | nnnnnnnnnn | nnnnnnnnnn | nnnnnnnnnn | 6840 |
| nnnnnnnnnn | nnnnnnnnnn | nnnnnnnnnn | nnnnnnnnnn | nnnnnnnnnn | nnnnnnnnnn | 6900 |
| nnnnnnnnnn | nnnnnnnnnn | nnnnnnnnnn | nnnnnnnnnn | nnnnnnnnnn | nnnnnnnnnn | 6960 |
| nnnnnnnnnn | nnnnnnnnnn | nnnnnnnnnn | nnnnnnnnnn | nnnnnnnnnn | nnnnnnnnnn | 7020 |
| nnnnnnnnnn | nnnnnnnnnn | nnnnnnnnnn | nnnnnnnnnn | nnnnnnnnnn | nnnnnnnnnn | 7080 |
| nnnnnnnnnn | nnnnnnnnnn | nnnnnnnnnn | nnnnnnnnnn | nnnnnnnnnn | nnnnnnnnnn | 7140 |
| nnnnnnnnnn | nnnnnnnnnn | nnnnnnnnnn | nnnnnnnnnn | nnnnnnnnnn | nnnnnnnnnn | 7200 |
| nnnnnnnnnn | nnnnnnnnnn | nnnnnnnnnn | nnnnnnnnnn | nnnnnnnnnn | nnnnnnnnnn | 7260 |
| nnnnnnnnnn | nnnnnnnnnn | nnnnnnnnnn | nnnnnnnnnn | nnnnnnnnnn | nnnnnnnnnn | 7320 |
| nnnnnnnnnn | nnnnnnnnnn | nnnnnnnnnn | nnnnnnnnnn | nnnnnnnnnn | nnnnnnnnnn | 7380 |
| nnnnnnnnnn | nnnnnnnnnn | nnnnnnnnnn | nnnnnnnnnn | nnnnnnnnnn | nnnnnnnnnn | 7440 |
| nnnnnnnnnn | nnnnnnnnnn | nnnnnnnnnn | nnnnnnnnnn | nnnnnnnnnn | nnnnnnnnnn | 7500 |
| nnnnnnnnnn | nnnnnnnnnn | nnnnnnnnnn | nnnnnnnnnn | nnnnnnnnnn | nnnnnnnnnn | 7560 |
| nnnnnnnnnn | nnnnnnnnnn | nnnnnnnnnn | nnnnnnnnnn | nnnnnnnnnn | nnnnnnnnnn | 7620 |
| nnnnnnnnnn | nnnnnnnnnn | nnnnnnnnnn | nnnnnnnnnn | nnnnnnnnnn | nnnnnnnnnn | 7680 |
| nnnnnnnnnn | nnnnnnnnnn | nnnnnnnnnn | nnnnnnnnnn | nnnnnnnnnn | nnnnnnnnnn | 7740 |
| nnnnnnnnnn | nnnnnnnnnn | nnnnnnnnnn | nnnnnnnnnn | nnnnnnnnnn | nnnnnnnnnn | 7800 |
| nnnnnnnnnn | nnnnnnnnnn | nnnnnnnnnn | nnnnnnnnnn | nnnnnnnnnn | nnnnnnnnnn | 7860 |
| nnnnnnnnnn | nnnnnnnnnn | nnnnnnnnnn | nnnnnnnnnn | nnnnnnnnnn | nnnnnnnnnn | 7920 |
| nnnnnnnnnn | nnnnnnnnnn | nnnnnnnnnn | nnnnnnnnnn | nnnnnnnnnn | nnnnnnnnnn | 7980 |
| nnnnnnnnnn | nnnnnnnnnn | nnnnnnnnnn | nnnnnnnnnn | nnnnnnnnnn | nnnnnnnnnn | 8040 |
| nnnnnnnnnn | nnnnnnnnnn | nnnnnnnnnn | nnnnnnnnnn | nnnnnnnnnn | nnnnnnnnnn | 8100 |

```
nnnnnnnnnn nnnnnnnnnn nnnnnnnnnn nnnnnnnnnn nnnnnnnnnn nnnnnnnnnn      8160
nnnnnnnnnn nnnnnnnnnn nnnnnnnnnn nnnnnnnnnn nnnnnnnnnn nnnnnnnnnn      8220
nnnnnnnnnn nnnnnnnnnn nnnnnnnnnn nnnnnnnnnn nnnnnnnnnn nnnnnnnnnn      8280
nnnnnnnnnn nnnnnnnnnn nnnnnnnnnn nnnnnnnnnn nnnnnnnnnn nnnnnnnnnn      8340
nnnnnnnnnn nnnnnnnnnn nnnnnnnnnn nnnnnnnnnn nnnnnnnnnn nnnnnnnnnn      8400
nnnnnnnnnn nnnnnnnnnn nnnnnnnnnn nnnnnnnnnn nnnnnnnnnn nnnnnnnnnn      8460
nnnnnnnnnn nnnnnnnnnn nnnnnnnnnn nnnnnnnnnn nnnnnnnnnn nnnnnnnnnn      8520
nnnnnnnnnn nnnnnnnnnn nnnnnnnnnn nnnnnnnnnn nnnnnnnnnn nnnnnnnnnn      8580
nnnnnnnnnn nnnnnnnnnn nnnnnnnnnn nnnnnnnnnn nnnnnnnnnn nnnnnnnnnn      8640
nnnnnnnnnn nnnnnnnnnn nnnnnnnnnn nnnnnnnnnn nnnnnnnnnn nnnnnnnnnn      8700
nnnnnnnnnn nnnnnnnnnn nnnnnnnnnn nnnnnnnnnn nnnnnnnnnn nnnnnnnnnn      8760
nnnnnnnnnn nnnnnnnnnn nnnnnnnnnn nnnnnnnnnn nnnnnnnnnn nnnnnnnnnn      8820
nnnnnnnnnn nnnnnnnnnn nnnnnnnnnn nnnnnnnnnn nnnnnnnnnn nnnnnnnnnn      8880
nnnnnnnnnn nnnnnnnnnn nnnnnnnnnn nnnnnnnnnn nnnnnnnnnn nnnnnnnnnn      8940
nnnnnnnnnn nnnnnnnnnn nnnnnnnnnn nnnnnnnnnn nnnnnnnnnn nnnnnnnnnn      9000
nnnnnnnnnn nnnnnnnnnn nnnnnnnnnn nnnnnnnnnn nnnnnnnnnn nnnnnnnnnn      9060
nnnnnnnnnn nnnnnnnnnn nnnnnnnnnn nnnnnnnnnn nnnnnnnnnn nnnnnnnnnn      9120
nnnnnnnnnn nnnnnnnnnn nnnnnnnnnn nnnnnnnnnn nnnnnnnnnn nnnnnnnnnn      9180
nnnnnnnnnn nnnnnnnnnn nnnnnnnnnn nnnnnnnnnn nnnnnnnnnn nnnnnnnnnn      9240
nnnnnnnnnn nnnnnnnnnn nnnnnnnnnn nnnnnnnnnn nnnnnnnnnn nnnnnnnnnn      9300
nnnnnnnnnn nnnnnnnnnn nnnnnnnnnn nnnnnnnnnn nnnnnnnnnn nnnnnnnnnn      9360
nnnnnnnnnn nnnnnnnnnn nnnnnnnnnn nnnnnnnnnn nnnnnnnnnn nnnnnnnnnn      9420
nnnnnnnnnn nnnnnnnnnn nnnnnnnnnn nnnnnnnnnn nnnnnnnnnn nnnnnnnnnn      9480
nnnnnnnnnn nnnnnnnnnn nnnnnnnnnn nnnnnnnnnn nnnnnnnnnn nnnnnnnnnn      9540
nnnnnnnnnn nnnnnnnnnn nnnnnnnnnn nnnnnnnnnn nnnnnnnnnn nnnnnnnnnn      9600
nnnnnnnnnn nnnnnnnnnn nnnnnnnnnn nnnnnnnnnn nnnnnnnnnn nnnnnnnnnn      9660
nnnnnnnnnn nnnnnnnnnn nnnnnnnnnn nnnnnnnnnn nnnnnnnnnn nnnnnnnnnn      9720
nnnnnnnnnn nnnnnnnnnn nnnnnnnnnn nnnnnnnnnn nnnnnnnnnn nnnnnnnnnn      9780
nnnnnnnnnn nnnnnnnnnn nnnnnnnnnn nnnnnnnnnn nnnnnnnnnn nnnnnnnnnn      9840
nnnnnnnnnn nnnnnnnnnn nnnnnnnnnn nnnnnnnnnn nnnnnnnnnn nnnnnnnnnn      9900
nnnnnnnnnn nnnnnnnnnn nnnnnnnnnn nnnnnnnnnn nnnnnnnnnn nnnnnnnnnn      9960
nnnnnnnnnn nnnnnnnnnn nnnnnnnnnn nnnnnnnnnn nnnnnnnnnn nngtcggagc     10020
```

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      paired oligonucleotide tag
<220> FEATURE:
<221> NAME/KEY: modified_base
<222> LOCATION: (1)..(1)
<223> OTHER INFORMATION: a, c, t or g
<220> FEATURE:
<221> NAME/KEY: modified_base

```
<222> LOCATION: (22)..(22)
<223> OTHER INFORMATION: a, c, t or g

<400> SEQUENCE: 28
ngtcggagcg gccgctccga cn                                         22

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      vector insert oligonucleotide

<400> SEQUENCE: 29
tgcatccatg gatttggtgt actccaaatc catggtacat                      40

<210> SEQ ID NO 30
<211> LENGTH: 40
<212> TYPE: DNA
<213> ORGANISM: Artificial Sequence
<220> FEATURE:
<223> OTHER INFORMATION: Description of Artificial Sequence: Synthetic
      vector insert oligonucleotide

<400> SEQUENCE: 30
tgcatccatg gatttggtgt actccaaatc catggtacat                      40

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide linker
<220> FEATURE:
<221> NAME/KEY: modified_base
<222> LOCATION: (19)..(19)
<223> OTHER INFORMATION: a, c, t or g

<400> SEQUENCE: 31
tgcatccatg gatccgacng tcggatccat ggtacat                         37

<210> SEQ ID NO 32
<211> LENGTH: 37
<212> TYPE: DNA
<213> ORGANISM: Artificial Sequence
<220> FEATURE:
<223> OTHER INFORMATION: Description of Artificial Sequence: Synthetic
      cloned oligonucleotide tag
<220> FEATURE:
<221> NAME/KEY: modified_base
<222> LOCATION: (19)..(19)
<223> OTHER INFORMATION: a, c, t or g

<400> SEQUENCE: 32
tgcatccatg gatccgacng tcggatccat ggtacat                         37

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      paired oligonucleotide tag
<220> FEATURE:
<221> NAME/KEY: modified_base
<222> LOCATION: (1)..(1)
<223> OTHER INFORMATION: a, c, t or g
```

```
<220> FEATURE:
<221> NAME/KEY: modified_base
<222> LOCATION: (22)..(22)
<223> OTHER INFORMATION: a, c, t or g

<400> SEQUENCE: 33
ngtcggagcg gccgctccga cn                                              22
```